US012616697B2

(12) United States Patent
Sehnert et al.

(10) Patent No.: US 12,616,697 B2
(45) Date of Patent: May 5, 2026

(54) METHODS OF TREATMENT WITH MYOSIN MODULATOR

(71) Applicant: MyoKardia, Inc., Brisbane, CA (US)

(72) Inventors: Amy Sehnert, Brisbane, CA (US); Jay M. Edelberg, Brisbane, CA (US)

(73) Assignee: MyoKardia, Inc., Brisbane, CA (US)

( * ) Notice: Subject to any disclaimer, the term of this patent is extended or adjusted under 35 U.S.C. 154(b) by 516 days.

(21) Appl. No.: 18/042,632

(22) PCT Filed: Aug. 26, 2021

(86) PCT No.: PCT/US2021/047711
§ 371 (c)(1),
(2) Date: Feb. 23, 2023

(87) PCT Pub. No.: WO2022/047004
PCT Pub. Date: Mar. 3, 2022

(65) Prior Publication Data

US 2024/0299390 A1 Sep. 12, 2024

Related U.S. Application Data

(60) Provisional application No. 63/072,094, filed on Aug. 28, 2020.

(51) Int. Cl.
*A61K 31/513* (2006.01)
*A61P 9/00* (2006.01)

(52) U.S. Cl.
CPC .............. *A61K 31/513* (2013.01); *A61P 9/00* (2018.01)

(58) Field of Classification Search
CPC ................................ A61K 31/513; A61P 9/00
See application file for complete search history.

(56) References Cited

U.S. PATENT DOCUMENTS

| | | | |
|---|---|---|---|
| 2014/0378464 | A1 | 12/2014 | Oslob et al. |
| 2014/0378491 | A1 | 12/2014 | Oslob et al. |
| 2016/0176868 | A1 | 6/2016 | Oslob et al. |
| 2020/0054636 | A1 | 2/2020 | Semigran et al. |
| 2020/0165247 | A1 | 5/2020 | Grillo et al. |

FOREIGN PATENT DOCUMENTS

| | | | | |
|---|---|---|---|---|
| CN | 110698415 | A * | 1/2020 | ................ A61P 9/10 |
| WO | 2014205223 | A1 | 12/2014 | |
| WO | WO-2019028360 | A1 * | 2/2019 | ........... A61K 31/513 |
| WO | 2019144041 | A1 | 7/2019 | |
| WO | 2020005887 | A1 | 1/2020 | |
| WO | 2020005888 | A1 | 1/2020 | |
| WO | 2020047447 | A1 | 3/2020 | |
| WO | 2020092208 | A1 | 5/2020 | |
| WO | 2020/151605 | A1 | 7/2020 | |
| WO | 2020165247 | A1 | 8/2020 | |
| WO | 2020/257609 | A1 | 12/2020 | |
| WO | 2021/092598 | A1 | 5/2021 | |

OTHER PUBLICATIONS

English Translation for CN 110698415A Hu et al. (2020).*
Supplemental European Search Report regarding Application No. EP 21 86 2716 dated Jul. 25, 2024.
Awinda Peter O et al, "Mavacamten Decreases Maximal Force and Ca2+—Sensitivity of Contraction in Myocardial Strips from a Mouse Model for Mypertrophic Cardiomyopathy", Biophysical Journal, Elsevier, Amsterdam, NL, vol. 118, No. 3, Feb. 7, 2020.
Ho Carolyn Y. et al: "Evaluation of Mavacamten in Symptomatic Patients with Nonobstructive Hypertrophic Cardiomyopathy", Journal of the American College of Cardiology, vol. 75, No. 21, Jun. 1, 2020, pp. 2649-2660.
Written Opinion of International Searching Authority for PCT/US2021/47711 dated Dec. 8, 2021.

* cited by examiner

*Primary Examiner* — Kevin E Weddington
(74) *Attorney, Agent, or Firm* — Honigman LLP; Andrew S. Chipouras; Jonathan P. O'Brien

(57) ABSTRACT

Methods of treatment comprising administering a therapeutically effective amount of a myosin modulator or a pharmaceutically acceptable salt thereof to a subject in need thereof and diagnostic methods useful in connection with those treatments are disclosed herein. Treatments performed in the absence of beta blocker therapy or with reduced beta blocker therapy are also disclosed.

52 Claims, 23 Drawing Sheets p<0.01 for change from baseline.

*p<0.05 for change from baseline.

EOS = end of study; EOT = end of treatment; NYHA = New York Heart Association (functional classification); QD = once daily; SRT = septal reduction therapy; TTE = transthoracic echocardiogram

METHODS OF TREATMENT WITH MYOSIN MODULATOR

CROSS-REFERENCE TO RELATED APPLICATION

This application is a 35 U.S.C. § 371 United States National Phase Application of PCT Application No. PCT/US2021/047711, filed Aug. 26, 2021 which claims priority from U.S. Provisional Patent Application 63/072,094, filed Aug. 28, 2020. The disclosures of those priority applications are incorporated by reference herein in their entirety.

TECHNICAL FIELD

The present disclosure relates to methods of treatment comprising administering a therapeutically effective amount of a myosin modulator or a pharmaceutically acceptable salt thereof to a subject in need thereof and diagnostic methods useful in connection with those treatments. The disclosure also relates to treatment performed in the absence of beta blocker therapy or with reduced beta blocker therapy.

BACKGROUND

Hypertrophic cardiomyopathy (HCM) is a chronic, progressive disease in which excessive contraction of the heart muscle and reduced left ventricle filling capacity can lead to the development of debilitating symptoms and cardiac dysfunction. HCM is estimated to affect one in every 500 people. The most frequent cause of HCM is mutations in the proteins of the cardiac sarcomere. In approximately two-thirds of HCM subjects, the path followed by blood exiting the heart, known as the left ventricular outflow tract (LVOT), becomes obstructed by the enlarged and diseased muscle, restricting the flow of blood from the heart to the rest of the body (obstructive HCM). In other subjects, the thickened heart muscle does not block the LVOT, and their disease is driven by diastolic impairment due to the enlarged and stiffened heart muscle (non-obstructive HCM). In either obstructive or non-obstructive HCM subjects, exertion can result in fatigue or shortness of breath, interfering with a subject's ability to participate in activities of daily living. HCM has also been associated with increased risks of atrial fibrillation, stroke, heart failure and sudden cardiac death.

Mavacamten is a novel, oral, allosteric modulator of cardiac myosin being developed for the treatment of hypertrophic cardiomyopathy (HCM). This therapy is intended to reduce cardiac muscle contractility by inhibiting the excessive myosin-actin cross-bridge formation that underlies the excessive contractility, left ventricular hypertrophy and reduced compliance characteristics of HCM. Mavacamten is currently being evaluated in multiple clinical trials for the treatment of obstructive and non-obstructive HCM. A pivotal Phase 3 clinical trial, known as EXPLORER-HCM, is being conducted in subjects with symptomatic, obstructive HCM and Additionally, a Phase 2 clinical trial known as MAVERICK-HCM is being conducted in subjects with symptomatic, non-obstructive HCM (nHCM); and two long term follow-up studies are also ongoing, the PIONEER open-label extension study of obstructive HCM subjects from Phase 2 PIONEER trial and the MAVA-LTE, an extension study for subjects who have completed either EXPLORER-HCM or MAVERICK-HCM. Mavacamten is the first myosin inhibitor to enter into clinical trials.

Due to observations unfolding in the clinical trials with mavacamten and with mavacamten and other myosin inhibitors in the pre-clinical setting, new insights into how myosin inhibitors can be used beneficially to impact the disease state of HCM and other diseases will be provided in this application.

SUMMARY

Provided herein is a method of treating a patient having cardiac hypercontractility, impaired cardiac relaxation and/or left ventricular hypertrophy, wherein the patient is undergoing β blocker therapy, the method comprising:

- administering to the patient a therapeutically effective amount of a myosin inhibitor during a first treatment phase during which the patient also receives β blocker therapy; and
- continuing to administer to the patient a therapeutically effective amount of a myosin inhibitor during a second treatment phase during which the patient either (a) does not receive β blocker therapy, or (b) receives a reduced amount of β blocker therapy.

In some embodiments, the patient does not receive β blocker therapy during the second treatment phase.

In some embodiments, the patient receives a reduced amount of β blocker therapy during the second treatment phase. In some embodiments, the reduced amount of β blocker therapy comprises a smaller dose of a β blocker. In some embodiments, the reduced amount of β blocker therapy comprises a less frequent dose of a β blocker.

In some embodiments, the method comprises transitioning from the first treatment phase to the second treatment phase when the patient achieves a therapeutically effective steady state of the myosin inhibitor.

In some embodiments, the steady state is achieved when the patient achieves a dose amount with no significant change in efficacy. In some embodiments, the steady state is achieved in the time period of about 4 to 5 times the half life of the myosin inhibitor following administration of the myosin inhibitor. In some embodiments, the steady state is achieved in the time period of about 4.5 times the half life of the myosin inhibitor following administration of the myosin inhibitor.

In some embodiments, the patient achieves the steady state when the patient achieves a dose amount wherein the patient's Valsalva or post-exercise LVOT gradient remains below 30 mmHg. In some embodiments, the patient achieves the steady state when the patient achieves a dose amount wherein the patient's Valsalva or post-exercise LVOT gradient remains below 30 mmHg and ejection fraction remains above 50%.

In some embodiments, the first treatment phase is about 4 weeks to about 28 weeks. In some embodiments, the first treatment phase is about 24 weeks.

In some embodiments, the method comprises transitioning from the first treatment phase to the second treatment phase when the patient achieves a Valsalva or post-exercise LVOT gradient below 30 mmHg. In some embodiments, the method comprises transitioning from the first treatment phase to the second treatment phase when the patient achieves a Valsalva or post-exercise LVOT gradient below 30 mmHg and an ejection fraction is above 50%.

In some embodiments, the myosin inhibitor is mavacamten or a pharmaceutically acceptable salt thereof, and the method comprises transitioning from the first treatment phase to the second treatment phase when the patient achieves a trough blood plasma concentration of mavacamten of between 350 and 700 ng/mL.

In some embodiments, the first treatment phase is about 4 weeks to about 28 weeks. In some embodiments, the first treatment phase is about 4-6 weeks, wherein the steady state dose is about 5 mg per day of mavacamten. In some embodiments, the first treatment phase is about 14 weeks.

In some embodiments, the method comprises transitioning from the first treatment phase to the second treatment phase when the patient experiences a side effect due to R blocker therapy. In some embodiments, the side effect is fatigue, orthostatic hypertension, erectile dysfunction, or any combination thereof.

In some embodiments, the method comprises transitioning from the first treatment phase to the second treatment phase when a clinician deems necessary to discontinue or reduce the amount of β blocker therapy.

In some embodiments, the myosin inhibitor is mavacamten or a pharmaceutically acceptable salt thereof.

In some embodiments, the patient has hypertrophic cardiomyopathy (HCM). In some embodiments, the patient has obstructive hypertrophic cardiomyopathy (oHCM). In some embodiments, the patient has non-obstructive hypertrophic cardiomyopathy (nHCM). In some embodiments, the patient has heart failure with preserved ejection fraction (HFpEF).

In some embodiments, the patient is not suffering from one or more of, or is not suffering from any of: coronary artery disease (CAD), chest pain, angina, super ventricular arrhythmia, atrial fibrillation, congestive heart failure, left ventricular failure, stress cardiomyopathy, cardiac hypertension, ventricular tachycardia (VT), valvular disease, aortic stenosis, and coronary heart disease. In some embodiments, the patient is not suffering from atrial fibrillation. In some embodiments, the patient is not suffering from coronary artery disease (CAD).

In some embodiments, the β blocker therapy comprises administration of one or more β blockers selected from the group consisting of acebutolol, atenolol, betaxolol, bisoprolol, metoprolol, nadolol, nebivolol, propranolol, and sotalol.

In some embodiments, the peak exercise capacity of the patient is increased and/or maximized. In some embodiments, the patient achieves an improvement in $pVO_2$ of at least about 2.2 mL/kg/min. In some embodiments, the patient achieves (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class.

In some embodiments, the patient has an ejection fraction >55% prior to beginning the first treatment phase. In some embodiments, the patient has an E/e'>14 prior to beginning the first treatment phase. In some embodiments, the patient has a left ventricular wall thickness ≥15 mm or ≥13 mm with family history of HCM prior to beginning the first treatment phase.

In some embodiments, the patient with cardiac hypercontractility has ejection fraction of >55% and evidence of oHCM, HCM and/or heart failure symptoms prior to beginning the first treatment phase.

Also provided herein is a method of treating a patient having cardiac hypercontractility, impaired cardiac relaxation and/or left ventricular hypertrophy, wherein the patient is undergoing β blocker therapy, the method comprising:

- discontinuing the β blocker therapy or reducing the amount of β blocker therapy; and
- administering to the patient a therapeutically effective amount of a myosin inhibitor.

In some embodiments, the method comprises discontinuing the β blocker therapy.

In some embodiments, the method comprises reducing the amount of β blocker therapy. In some embodiments, reducing the amount of β blocker therapy comprises reducing the dose of a β blocker. In some embodiments, reducing the amount of β blocker therapy comprises reducing the frequency of dosing of a β blocker.

In some embodiments, the myosin inhibitor is mavacamten or a pharmaceutically acceptable salt thereof.

In some embodiments, administering to the patient a therapeutically effective amount of a myosin inhibitor comprises administering a starting dose of 5 mg of mavacamten per day. In some embodiments, the starting dose of 5 mg of mavacamten per day is adjusted or maintained based on the Valsalva or post-exercise LVOT gradient of the patient. In some embodiments, the starting dose of mavacamten is reduced to 2.5 mg if the Valsalva or post-exercise LVOT gradient of the patient is less than 30 mmHg. In some embodiments, the starting dose of mavacamten is reduced to 2.5 mg if the Valsalva or post-exercise LVOT gradient of the patient is less than 30 mmHg after 8 weeks of administering 5 mg of mavacamten per day. In some embodiments, the starting dose of mavacamten is increased to 10 mg if the Valsalva or post-exercise LVOT gradient of the patient is greater than or equal to 30 mmHg. In some embodiments, the starting dose of mavacamten is increased to 10 mg if the Valsalva or post-exercise LVOT gradient of the patient is greater than or equal to 30 mmHg after 8 weeks of administering 5 mg of mavacamten per day.

In some embodiments, the patient has hypertrophic cardiomyopathy (HCM). In some embodiments, the patient has obstructive hypertrophic cardiomyopathy (oHCM). In some embodiments, the patient has non-obstructive hypertrophic cardiomyopathy (nHCM). In some embodiments, the patient has heart failure with preserved ejection fraction (HFpEF).

In some embodiments, the patient is not suffering from one or more of, or is not suffering from any of: coronary artery disease (CAD), chest pain, angina, super ventricular arrhythmia, atrial fibrillation, congestive heart failure, left ventricular failure, stress cardiomyopathy, cardiac hypertension, ventricular tachycardia (VT), valvular disease, aortic stenosis, and coronary heart disease. In some embodiments, the patient is not suffering from atrial fibrillation. In some embodiments, the patient is not suffering from coronary artery disease (CAD).

In some embodiments, the β blocker therapy comprises administration of one or more β blockers selected from the group consisting of acebutolol, atenolol, betaxolol, bisoprolol, metoprolol, nadolol, nebivolol, propranolol, and sotalol.

In some embodiments, the peak exercise capacity of the patient is increased and/or maximized. In some embodiments, the patient achieves an improvement in $pVO_2$ of at least about 2.2 mL/kg/min. In some embodiments, the patient achieves (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class.

In some embodiments, the patient has an ejection fraction >55% prior to administration of the myosin inhibitor. In some embodiments, the patient has an E/e'>14 prior to administration of the myosin inhibitor. In some embodiments, the patient has a left ventricular wall thickness ≥15 mm or ≥13 mm with family history of HCM prior to administration of the myosin inhibitor.

In some embodiments, the patient with cardiac hypercontractility has ejection fraction of >55% and evidence of oHCM, HCM and/or heart failure symptoms prior to beginning the first treatment phase.

Also provided herein is a method of treating a patient having cardiac hypercontractility, impaired cardiac relaxation and/or left ventricular hypertrophy, wherein the patient is not undergoing β blocker therapy, the method comprising administering to the patient a therapeutically effective amount of a myosin inhibitor.

In some embodiments, the patient has never received β blocker therapy.

In some embodiments, the patient has previously received β blocker therapy but has not received β blocker therapy for at least 14 days prior to administration of the myosin inhibitor. In some embodiments, the patient has previously received β blocker therapy but has not received β blocker therapy for at least 30, at least 60, or at least 90 days prior to administration of the myosin inhibitor.

In some embodiments, the patient is an athlete or has an active lifestyle.

In some embodiments, the myosin inhibitor is mavacamten or a pharmaceutically acceptable salt thereof.

In some embodiments, the patient has hypertrophic cardiomyopathy (HCM). In some embodiments, the patient has obstructive hypertrophic cardiomyopathy (oHCM). In some embodiments, the patient has non-obstructive hypertrophic cardiomyopathy (nHCM). In some embodiments, the patient has heart failure with preserved ejection fraction (HFpEF).

In some embodiments, the patient is not suffering from one or more of, or is not suffering from any of coronary artery disease (CAD), chest pain, angina, super ventricular arrhythmia, atrial fibrillation, congestive heart failure, left ventricular failure, stress cardiomyopathy, cardiac hypertension, ventricular tachycardia (VT), valvular disease, aortic stenosis, and coronary heart disease. In some embodiments, the patient is not suffering from atrial fibrillation. In some embodiments, the patient is not suffering from coronary artery disease (CAD).

In some embodiments, the β blocker therapy comprises administration of one or more β blockers selected from the group consisting of acebutolol, atenolol, betaxolol, bisoprolol, metoprolol, nadolol, nebivolol, propranolol, and sotalol.

In some embodiments, the peak exercise capacity of the patient is increased and/or maximized. In some embodiments, the patient achieves an improvement in $pVO_2$ of at least about 2.2 mL/kg/min. In some embodiments, the patient achieves (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class.

In some embodiments, the patient has an ejection fraction >55% prior to administration of the myosin inhibitor. In some embodiments, the patient has an E/e'>14 prior to administration of the myosin inhibitor. In some embodiments, the patient has a left ventricular wall thickness ≥15 mm or ≥13 mm with family history of HCM prior to administration of the myosin inhibitor.

In some embodiments, the patient with cardiac hypercontractility has ejection fraction of >55% and evidence of oHCM, HCM and/or heart failure symptoms prior to beginning the first treatment phase.

In some embodiments, the present disclosure provides a method for treating a disease in a subject comprising administering to the subject in need thereof a therapeutically effective amount of a myosin modulator, wherein the subject has (1) an elevated level of a cardiac troponin and/or (2) an elevated level of BNP or proBNP. In a further embodiment, such subject has normal contractility or systolic hypercontractility. In some embodiments, such subject has a left ventricle ejection fraction (LVEF)≥52% or ≥50%.

In some embodiments, the subject to be treated with a myosin inhibitor has (1) an elevated level of a cardiac troponin and/or (2) an elevated level of BNP or proBNP, wherein such subject has normal contractility or systolic hypercontractility and (A) diastolic dysfunction or elevated filling pressure and/or (B) left ventricle hypertrophy or left atrial enlargement.

In some embodiments, such subject has a left ventricle ejection fraction (LVEF)≥52% or ≥50%. In some embodiments, the subject has either (1) a diastolic dysfunction, (2) elevated left ventricular filling pressure, or (3) left ventricular hypertrophy and/or left atrial size enlargement.

In some embodiments, the myosin modulator is a myosin inhibitor. In some embodiments, the myosin inhibitor is a myosin inhibitor specifically identified in this application. In some embodiments, a myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has an elevated level of cardiac troponin I (cTnI) or cardiac troponin T (cTnT). In some embodiments, the cardiac troponin is cTnI. In some embodiments, the cardiac troponin is cTnT. In some embodiments, the cardiac troponin is high sensitivity cTnI (hs-cTnI). In some embodiments, the cardiac troponin is high sensitivity cTnT (hs-cTnT). In some embodiments, the myosin inhibitor is mavacamten or a pharmaceutically acceptable salt thereof In some embodiments, the present disclosure provides a method for treating a disease in a subject, wherein the subject is suffering from a symptom of a cardiovascular disease.

In some embodiments, the present disclosure provides a method for treating a disease in a subject, wherein the subject is suffering from a symptom selected from shortness of breath, dizziness, chest pain, syncope, or a limit on an activity of daily living. In some embodiments, the limit on an activity of daily living is selected from the group consisting of a limit on personal care, mobility, or eating.

In some embodiments, the present disclosure provides a method for treating a disease in a subject comprising administering to the subject in need thereof a therapeutically effective amount of a myosin modulator or inhibitor, wherein the subject has an elevated pro-BNP or BNP level. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has (1) an elevated level of cardiac troponin I (cTnI) or cardiac troponin T (cTnT) and (2) an elevated pro-BNP level. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has an elevated E/e'. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has an elevated level of cardiac troponin and an elevated E/e'. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has an elevated level of cardiac troponin I (cTnI) and/or cardiac troponin T (cTnT), and/or an elevated pro-BNP level, and/or an elevated E/e'. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has a normal or hypercontractile left ventricle ejection fraction (LVEF). In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject has (1) an elevated level of cardiac troponin I (cTnI) or cardiac troponin T (cTnT), and/or (2) an elevated pro-BNP level, and/or (3) an elevated E/e', and/or (4) a normal or hypercontractile left ventricle ejection fraction (LVEF). In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject is suffering from diastolic dysfunction, left ventricular hypertrophy (LVH), angina, ischemia, hypertrophic cardiomyopathy (HCM), restrictive cardiomyopathy (RCM), or heart failure with preserved ejection fraction (HFpEF); or wherein the subject is suffering from valvular aortic stenosis, mixed LV systolic and diastolic dysfunction, idiopathic RV hypertrophy, chronic kidney disease, aortic insufficiency, tetralogy of Fallot, mitral stenosis, or acute coronary syndromes. In some embodiments, the myosin inhibitor is mavacamten or a pharmaceutically acceptable salt thereof.

In some embodiments, angina is microvascular angina. In some embodiments, the LVH is malignant LVH.

In some embodiments, the present disclosure provides a method for treating a disease in a subject comprising administering to the subject in need thereof a therapeutically effective amount of a myosin modulator or inhibitor, wherein the subject is diagnosed with an HCM. In some embodiments, HCM is obstructive HCM. In some embodiments, the HCM is non-obstructive HCM. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject is diagnosed with HFpEF. In some embodiments, the myosin inhibitor is mavacamten or a pharmaceutically acceptable salt thereof.

In some embodiments, the present disclosure provides a method for treating a disease in a subject comprising administering to the subject in need thereof a therapeutically effective amount of a myosin modulator or inhibitor, wherein the subject is suffering from a disease comprising oHCM, nHCM, HFpEF, left ventricular hypertrophy (LVH), or angina, comprising the steps of:

- recommending the subject be tested for elevated cardiac troponin levels; and
- administering to the subject a therapeutically effective amount of a myosin modulator or inhibitor if the subject has elevated cardiac troponin levels. In some embodiments, the myosin inhibitor is mavacamten or a pharmaceutically acceptable salt thereof.

In some embodiments, cardiac troponin measured is cTnI, cTnT, hs-cTnI or hs-cTnT.

In some embodiments, the method further comprises the step of recommending the subject be tested for elevated NT-proBNP or BNP levels and then administering the myosin modulator or inhibitor if elevated cardiac troponin levels and elevated NT-proBNP or BNP levels are observed.

In some embodiments, the method further comprises the step of recommending the subject be evaluated for elevated E/e' and then administering the myosin modulator or inhibitor if elevated cardiac troponin levels and elevated E/e' are observed.

In some embodiments, the elevated E/e' is greater than 10. In some embodiments, the elevated E/e' is greater than 13. In some embodiments, the elevated E/e' is greater than 14.

In some embodiments, the method further comprises the step of recommending the subject be tested for elevated NT-proBNP or BNP levels and then administering the modulator or myosin inhibitor if (1) elevated NT-proBNP or BNP levels and (2) elevated E/e' are observed.

In some embodiments, the method further comprises the step of recommending the subject be tested for elevated cardiac troponin levels (i.e., cTnI or cTnT), and/or elevated NT-proBNP or BNP levels, and/or elevated E/e' and then administering the myosin modulator or inhibitor if elevated cardiac troponin, elevated NT-proBNP or BNP levels, and/or elevated E/e' are observed.

In some embodiments, the disease in the subject is diagnosed in accordance with the New York Heart Association (NYHA) classification. In some embodiments, the treatment comprises the step of assessing a NYHA classification score of the subject before and after administration of the therapeutically effective amount of a myosin modulator or inhibitor, wherein a decreased NYHA score after administration of the myosin modulator or inhibitor indicates a reduction in the extent of the disease in the subject.

In some embodiments, the treatment comprises the step of administering a myosin modulator or inhibitor until the subject has moved from a Class III to Class II, or Class II to Class I NYHA classification. In some embodiments, the myosin inhibitor is mavacamten or a pharmaceutically acceptable salt thereof.

In some embodiments, the NYHA classification score of the subject after administration of the therapeutically effective amount of a myosin modulator or inhibitor decreases from Class III to Class II, or from Class II to Class I.

In some embodiments, the disease in the subject is diagnosed in accordance with the Kansas City Cardiomyopathy Questionnaire (KCCQ) score.

In some embodiments, the treatment comprises the step of: determining a KCCQ score of the subject before and after administration of the therapeutically effective amount of a myosin modulator or inhibitor, wherein an increased KCCQ score after administration of the myosin modulator or inhibitor indicates a reduction in the extent of the disease in the subject.

In some embodiments, the subject is assessed peak oxygen consumption ($VO_2$) during exercise before and after administration of the therapeutically effective amount of a myosin modulator or inhibitor, wherein an increase in peak oxygen consumption in the subject after administration of the myosin modulator or inhibitor indicates a reduction in the extent of HCM or the at least one symptomatic component or condition thereof in the subject. In some embodiments, the subject is assessed for $VE/VCO_2$ or $VE/VCO_2$ slope during exercise before and after administration of the therapeutically effective amount of a myosin modulator or inhibitor. In some embodiments, the myosin inhibitor is mavacamten or a pharmaceutically acceptable salt thereof.

In some embodiments, after administration of the therapeutically effective amount of a myosin modulator or inhibitor, the subject experiences an improvement in $pVO_2$. In some embodiments, the subject experiences an improvement in NYHA Class. In some embodiments, the subject experiences (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class. In some embodiments, the subject experiences an improvement in $VE/VCO_2$ or $VE/VCO_2$ slope.

In some embodiments, the subject experiences a reduction in the risk of a major cardiovascular event. In some embodiments, the major cardiovascular event is selected from the group consisting of death, hospitalization for worsening of the disease, and myocardial infarction. In some embodiments, the subject experiences a statistically significant reduction in their level(s) of cardiac troponin and/or NT-proBNP or BNP In some embodiments, the patients have been diagnosed as having HCM and is eligible for surgical intervention or percutaneous ablation for treating the disease. In some embodiments, HCM is obstructive HCM. In some embodiments HCM is non-obstructive HCM.

In some embodiments, the patients have been diagnosed as having HFpEF.

In some embodiments, the subject to be treated is a child, an adolescent or an adult. In some embodiments, the adolescent is age 12-17. In some embodiments, the child is age 5-11.

In some embodiments, the present disclosure provides a method of reducing mortality in a subject suffering from a symptom due to a cardiovascular disease, comprising administering to the subject a therapeutically effective starting amount of a myosin modulator or inhibitor to achieve a stable desired clinical state, followed by administering a reduced dosage regimen of the myosin modulator or inhibitor to maintain or improve the desired clinical state.

In some embodiments, the symptom due to a cardiovascular disease is shortness of breath, dizziness, chest pain, syncope, fatigue, or limits on activities of daily living. In some embodiments, wherein the limit on an activity of daily living is selected from the group consisting of a limit on personal care, mobility, or eating. In some embodiments, the cardiovascular disease is selected from the group consisting of oHCM, nHCM, HFpEF, LVH, or angina. In some embodiments, the myosin inhibitor is mavacamten or a pharmaceutically acceptable salt thereof.

In some embodiments, the major cardiovascular event is selected from the group consisting of death, hospitalization for worsening of the disease, and myocardial infarction.

In some embodiments, the reduced daily dosage regimen is about 3 times, 4 times, or 5 times less than the amount of mavacamten needed to maintain a blood plasma level of mavacamten in the subject. In some embodiments, wherein the blood plasma level of mavacamten is between 200 to 750 ng/mL.

In some embodiments, the reduced dosage regimen is less than 5 mg per day, 4 mg or less per day, 3 mg or less per day, 2 mg or less per day, or 1 mg or less per day. In some embodiments, the starting therapeutically effective amount of mavacamten is from about 5 mg to about 15 mg, and the reduced dosage regimen is less than 5 mg per day mg of mavacamten per day.

In some embodiments, the reduced dosage regimen is administered to the subject chronically.

In some embodiments, the present disclosure provides a method of treating a subject after septal reduction therapy (SRT), comprising administering to the subject a reduced dosage regimen of the myosin modulator or inhibitor to maintain a stable desired clinical state after septal reduction therapy. In some embodiments, the myosin inhibitor is mavacamten or a pharmaceutically acceptable salt thereof.

In some embodiments, the reduced dosage regimen is a daily amount of mavacamten to achieve between 50-350 ng/ml plasma concentration or less than 5 mg per day, 1 4 mg or less per day, 3 mg or less per day, 2.5 mg or less per day, or 1 mg or less per day.

In some embodiments, the present disclosure provides a method of preventing HCM or LVH in a subject at risk of developing HCM or LVH, comprising and the step of administering to the at risk subject in need thereof a myosin modulator or inhibitor, wherein the subject has an elevated cardiac troponin level. In some embodiments, the at risk subject further has an elevated pro-BNP level. In some embodiments, the myosin inhibitor is mavacamten or a pharmaceutically acceptable salt thereof.

In some embodiments, the present disclosure provides a method of preventing HCM or LVH in a subject at risk of developing HCM or LVH, comprising and the step of administering to the subject in need thereof a low dose of a myosin modulator or inhibitor to completely or partially prevent development of HCM or LVH. In some embodiments, the myosin modulator or inhibitor is administered chronically. In some embodiments, the myosin inhibitor is mavacamten or a pharmaceutically acceptable salt thereof. In some embodiments, the subject to be treated is a child, an adolescent or an adult. In some embodiments, the subject has a symptom of a HCM or LVH comprising shortness of breath, dizziness, chest pain, syncope, fatigue and limits on activities of daily living.

In some embodiments, the limit on an activity of daily living is selected from the group consisting of a limit on personal care, mobility, or eating. In some embodiments, the low dose of the myosin modulator or inhibitor is an amount that is 3 to 5 times less than the amount needed for such myosin inhibitor to reduce the LVOT gradient in an oHCM patient. In some embodiments, the myosin inhibitor is mavacamten or a pharmaceutically acceptable salt thereof.

In some embodiments, the low dose of mavacamten is less than 5 mg per day or is a mount to maintain the blood plasma concentration of mavacamten between 50 to 350 ng/mL. In some embodiments, the low dose of mavacamten is 1 mg, 2 mg, 2.5 mg, or 3 mg per day. In some embodiments, the dosage regimen of a myosin modulator or inhibitor is administered to the subject at an early stage of development of HCM or LVH.

In some embodiments, the present disclosure provides a method of reducing an adverse event in a subject related to reduced cardiac output following a treatment comprising a myosin modulator or inhibitor, comprising the step of administering to the subject a therapeutic dose of a beta adrenergic agonist. In some embodiments, the myosin inhibitor is mavacamten or a pharmaceutically acceptable salt thereof.

In some embodiments, the beta adrenergic agonist is dobutamine or levosimendan. In some embodiments, the therapeutic dose of the beta adrenergic agonist is from about 5 μg/kg/min to about 10 μg/kg/min dobutamine infusion. In some embodiments, the therapeutic dose of the beta adrenergic agonist is infusion of from about 0.2 to about 0.4 μmol/kg of levosimendan over a period of about 30 minutes.

In some embodiments, the method further comprises the additional step of administering to the subject an intravenous volume supplementation and/or an arterial vasoconstrictor agent. In some embodiments, the arterial vasoconstrictor agent is an adrenergic agonist.

In some embodiments, the method further comprises monitoring the blood plasma concentration of mavacamten in the subject and determining that the subject has received a supratherapeutic dose of mavacamten based on the measured blood plasma concentration. In some embodiments, the method further comprise monitoring LVEF and/or monitoring NT-proBNP and determining that the subject has (or has likely) received a supratherapeutic dose of mavacamten based on the measured LVEF and/or NT-proBNP. In some embodiments, the supratherapeutic dose of mavacamten is a dose of mavacamten that causes a blood plasma concentration of mavacamten of greater than about 1000 ng/mL in the subject.

In some embodiments, the present disclosure provides a method of reducing mortality in a subject having oHCM and an interventricular septal (IVS) wall thickness>15 mm, comprising administering to the subject a therapeutically effective amount of mavacamten to reduce the interventricular septal (IVS) wall thickness to ≤15 mm, and maintain the IVS wall thickness at ≤15 mm.

In some embodiments, the present disclosure provides a method of reducing mortality in a subject having oHCM and an interventricular septal (IVS) wall thickness>15 mm, comprising administering to the subject a therapeutically effective amount of mavacamten to reduce the interventricular septal (IVS) wall thickness to ≤15 mm, and maintain the IVS wall thickness at ≤15 mm.

In some embodiments, the present disclosure provides a method of treating oHCM comprising the step of administering between 2-15 mg QD of mavacamten to a subject suffering from oHCM and having an interventricular septal (IVS) wall thickness of ≥15 mm until the IVS wall thickness of the subject is reduced to ≤15 mm.

In some embodiments, the present disclosure provides a method of for treating a subject with mavacamten for more than 28 weeks or more than 48 weeks. (i.e., can include longer term dosing).

In some embodiments, the present disclosure provide a method for treating a disease in a subject comprising administering to the subject in need thereof a therapeutically effective amount of a myosin modulator or inhibitor, wherein the subject has an elevated level of cardiac troponin and/or an elevated E/e', wherein the cardiac troponin is cardiac troponin I (cTnI) or cardiac troponin T (cTnT). In some embodiments, the subject further has an elevated NT-proBNP or BNP level. In some embodiments, the subject further has an elevated E/e'.

In some embodiments, the subject has a normal or hypercontractile left ventricle ejection fraction (LVEF). In some embodiments, normal LVEF is between 52-74%, or in some embodiments 50-74%.

In some embodiments, the subject is suffering from diastolic dysfunction, left ventricular hypertrophy (LVH), malignant LVH, angina, ischemia, hypertrophic cardiomyopathy (HCM), restrictive cardiomyopathy (RCM), or heart failure with preserved ejection fraction (HFpEF).

In some embodiments, the subject is suffering from valvular aortic stenosis, mixed LV systolic and diastolic dysfunction, idiopathic RV hypertrophy, chronic kidney disease, aortic insufficiency, tetralogy of Fallot, mitral stenosis, or acute coronary syndromes.

In some embodiments, the myosin modulator is a myosin inhibitor. In further embodiments, the myosin inhibitor is mavacamten or a pharmaceutically acceptable salt thereof.

In some embodiments, the subject experiences a reduction in the risk of a major cardiovascular event, wherein the major cardiovascular event is selected from the group consisting of death, hospitalization for worsening of the disease, and myocardial infarction.

In some embodiments, the subject experiences a statistically significant reduction in their level(s) of cardiac troponin and/or NT-proBNP or BNP.

In some embodiments, the disclosure provides a method for treating a disease in a subject comprising administering to the subject in need thereof a therapeutically effective amount of a myosin modulator or inhibitor, wherein the subject is suffering from a disease comprising oHCM, nHCM, HFpEF, diastolic dysfunction, left ventricular hypertrophy (LVH), malignant LVH, ischemia, or angina, comprising the steps of: recommending the subject be tested for elevated cardiac troponin levels and/or elevated E/e'; and administering to the subject a therapeutically effective amount of a myosin modulator or inhibitor if the subject has elevated cardiac troponin levels and/or elevated E/e'.

In some embodiments, the cardiac troponin measured is cTnI or cTnT. In some embodiments, the method further comprises the step of recommending the subject be tested for elevated E/e' and then administering the myosin modulator or inhibitor if elevated cardiac troponin levels and elevated E/e' are observed.

In some embodiments, the method further comprises the step of recommending the subject be evaluated for elevated NT-proBNP or BNP and then administering the myosin modulator or inhibitor if elevated cardiac troponin levels, elevated NT-proBNP or BNP levels, and elevated E/e' are observed.

In some embodiments, the method further comprises assessing peak oxygen consumption $pVO_2$ and/or $VE/VCO_2$ or $VE/VCO_2$ slope in the subject during exercise before and after administration of the therapeutically effective amount of a myosin modulator or inhibitor. In some embodiments, the peak oxygen consumption (pVO2) in the subject increases. In some embodiments, the $VE/VCO_2$ or $VE/VCO_2$ slope in the subject improves. In some embodiments, the disease is HFpEF, obstructive HCM, non-obstructive HCM.

In some embodiments, the subject experiences a reduction in the risk of a major cardiovascular event, e.g., wherein the major cardiovascular event is selected from the group consisting of death, hospitalization for worsening of the disease, and myocardial infarction. In some embodiments, the subject experiences a statistically significant reduction in their level(s) of cardiac troponin and/or NT-proBNP or BNP.

In some embodiments, the present disclosure provides after administration of the therapeutically effective amount of a myosin modulator or inhibitor, the subject experiences an improvement in $pVO_2$ and optionally an improvement in NYHA Class, for example: (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class.

In some embodiments, the present disclosure provides a method of administering mavacamten or a pharmaceutically acceptable salt thereof to a subject suffering from HFpEF, comprising: measuring a first NT-proBNP or BNP level in the subject; administering a first dose of mavacamten or a pharmaceutically acceptable salt thereof to the subject during a first treatment period; measuring a second NT-proBNP or BNP level in the subject; if the second NT-proBNP or BNP level is not at least 15-75% less than the first NT-proBNP or BNP level, then administering a second dose of mavacamten or a pharmaceutically acceptable salt thereof that is greater than the first dose during a second treatment period; and if the second NT-proBNP or BNP level is at least 15-75% less than the first NT-proBNP or BNP level, then administering the first dose of mavacamten or a pharmaceutically acceptable salt thereof during a second treatment period.

In some embodiments, the method further comprises: if the second NT-proBNP or BNP level is not at least 40-60% less than the first NT-proBNP or BNP level, then administering the second dose of mavacamten or a pharmaceutically acceptable salt thereof that is greater than the first dose during the second treatment period; and if the second NT-proBNP or BNP level is at least 40-60% less than the first NT-proBNP or BNP level, then administering the first dose of mavacamten or a pharmaceutically acceptable salt thereof during the second treatment period; or if the second NT-proBNP or BNP level is not at least 50% less than the first NT-proBNP or BNP level, then administering the second dose of mavacamten or a pharmaceutically acceptable salt thereof that is greater than the first dose during the second treatment period;

and if the second NT-proBNP or BNP level is at least 50% less than the first NT-proBNP or BNP level, then administering the first dose of mavacamten or a pharmaceutically acceptable salt thereof during the second treatment period. In some embodiments, the first NT-proBNP or BNP level is an elevated level.

In some embodiments, the method further comprises measuring a first LVEF of the subject, and measuring a second LVEF of the subject after the first LVEF and after the start of the first treatment period. In some embodiments, the method further comprises measuring the second LVEF at the end of, after, or within four weeks before the end of, the first treatment period.

In some embodiments, if the second NT-proBNP or BNP level is not at least 15-75% less than the first NT-proBNP or BNP level and the second LVEF is not at least 10-20% less than the first LVEF, then administering the second dose of mavacamten or a pharmaceutically acceptable salt thereof that is greater than the first dose during the second treatment period; and if the second NT-proBNP or BNP level is at least 15-75% less than the first NT-proBNP or BNP level or the second LVEF is at least 10-20% less than the second LVEF, then administering the first dose of mavacamten or a pharmaceutically acceptable salt thereof during the second treatment period; or if the second NT-proBNP or BNP level is not at least 40-60% less than the first NT-proBNP or BNP level and the second LVEF is not at least 10-20% less than the first LVEF, then administering the second dose of mavacamten or a pharmaceutically acceptable salt thereof that is greater than the first dose during the second treatment period; and if the second NT-proBNP or BNP level is at least 40-60% less than the first NT-proBNP or BNP level or the second LVEF is at least 10-20% less than the second LVEF, then administering the first dose of mavacamten or a pharmaceutically acceptable salt thereof during the second treatment period, or if the second NT-proBNP or BNP level is not at least 50% less than the first NT-proBNP or BNP level and the second LVEF is not at least 15% less than the first LVEF, then administering the second dose of mavacamten or a pharmaceutically acceptable salt thereof that is greater than the first dose during the second treatment period; and if the second NT-proBNP or BNP level is at least 50% less than the first NT-proBNP or BNP level or the second LVEF is at least 15% less than the second LVEF, then administering the first dose of mavacamten or a pharmaceutically acceptable salt thereof during the second treatment period.

In some embodiments, the first NT-proBNP or BNP level is measured before the first treatment period. In some embodiments, the first NT-proBNP or BNP level is measured immediately before, or within two weeks before, the first treatment period. In some embodiments, the second NT-proBNP or BNP level is measured during the first treatment period. In some embodiments, the second NT-proBNP or BNP level is measured at the end of, or within four weeks of the end of, the first treatment period.

In some embodiments, the present disclosure provides a method of administering mavacamten or a pharmaceutically acceptable salt thereof to a subject suffering from with HFpEF, comprising:

measuring a first cardiac troponin level in the subject;

administering a first dose of mavacamten or a pharmaceutically acceptable salt thereof to the subject during a first treatment period;

measuring a second cardiac troponin level in the subject;

if the second cardiac troponin level is not at least 10-50% less than the first cardiac troponin level, then administering a second dose of mavacamten or a pharmaceutically acceptable salt thereof that is greater than the first dose during a second treatment period; and if the second cardiac troponin level is at least 10-50% less than the first cardiac troponin level, then administering the first dose of mavacamten or a pharmaceutically acceptable salt thereof during a second treatment period.

In some embodiments, the method further comprises:

if the second cardiac troponin level is not at least 20-40% less than the first cardiac troponin level, then administering the second dose of mavacamten or a pharmaceutically acceptable salt thereof that is greater than the first dose during the second treatment period; and if the second cardiac troponin level is at least 20-40% less than the first cardiac troponin level, then administering the first dose of mavacamten or a pharmaceutically acceptable salt thereof during the second treatment period.

In some embodiments, the method further comprises:

if the second cardiac troponin level is not at least 30% less than the first cardiac troponin level, then administering the second dose of mavacamten or a pharmaceutically acceptable salt thereof that is greater than the first dose during the second treatment period; and if the second cardiac troponin level is at least 30% less than the first cardiac troponin level, then administering the first dose of mavacamten or a pharmaceutically acceptable salt thereof during the second treatment period.

In some embodiments, the method further comprises measuring a first LVEF of the subject, and measuring a second LVEF of the subject after the first LVEF and after the start of the first treatment period. In some embodiments, the method further comprises measuring the second LVEF at the end of, after, or within two weeks before the end of, the first treatment period.

In some embodiments, if the second cardiac troponin level is not at least 10-50% less than the first cardiac troponin level and the second LVEF is not at least 10-20% less than the first LVEF, then administering the second dose of mavacamten or a pharmaceutically acceptable salt thereof that is greater than the first dose during the second treatment period; and if the second cardiac troponin level is at least 10-50% less than the first cardiac troponin level or the second LVEF is at least 10-20% less than the second LVEF, then administering the first dose of mavacamten or a pharmaceutically acceptable salt thereof during the second treatment period, or if the second cardiac troponin level is not at least 20-40% less than the first cardiac troponin level and the second LVEF is not at least 10-20% less than the first LVEF, then administering the second dose of mavacamten or a pharmaceutically acceptable salt thereof that is greater than the first dose during the second treatment period; and if the second cardiac troponin level is at least 20-40% less than the first cardiac troponin level or the second LVEF is at least 10-20% less than the second LVEF, then administering the first dose of mavacamten or a pharmaceutically acceptable salt thereof during the second treatment period, or if the second cardiac troponin level is not at least 30% less than the first cardiac troponin level and the second LVEF is not at least 15% less than the first LVEF, then administering the second dose of mavacamten or a pharmaceutically acceptable salt thereof that is greater than the first dose during the second treatment period; and if the second cardiac troponin level is at least 30% less than the first cardiac troponin level or the second LVEF is at least 15% less than the second LVEF, then administering the first dose of mavacamten or a pharmaceutically acceptable salt thereof during the second treatment period.

In some embodiments, the method further comprises measuring a first NT-proBNP or BNP level of the subject, and measuring a second NT-proBNP or BNP level of the subject after the first NT-proBNP or BNP level and after the start of the first treatment period. In some embodiments, measuring the second NT-proBNP or BNP level at the end of, after, or within four weeks before the end of, the first treatment period.

In some embodiments, the method further comprises: if the second cardiac troponin level is not at least 10-50% less than the first cardiac troponin level and the second NT-proBNP or BNP level is not more than 20-60% greater than the first NT-proBNP or BNP level, then administering the second dose of mavacamten or a pharmaceutically acceptable salt thereof that is greater than the first dose during the second treatment period; and wherein if the second cardiac troponin level is at least 10-50% less than the first cardiac troponin level or the second NT-proBNP or BNP level is more than 20-60% greater than the first NT-proBNP or BNP level, then administering the first dose of mavacamten or a pharmaceutically acceptable salt thereof during the second treatment period, or if the second cardiac troponin level is not at least 20-40% less than the first cardiac troponin level and the second NT-proBNP or BNP level is not more than 40-55% greater than the first NT-proBNP or BNP level, then administering the second dose of mavacamten or a pharmaceutically acceptable salt thereof that is greater than the first dose during the second treatment period; and if the second cardiac troponin level is at least 20-40% less than the first cardiac troponin level or the second NT-proBNP or BNP level is more than 40-55% greater than the first NT-proBNP or BNP level, then administering the first dose of mavacamten or a pharmaceutically acceptable salt thereof during the second treatment period, or if the second cardiac troponin level is not at least 30% less than the first cardiac troponin level and the second NT-proBNP or BNP level is not more than 50% greater than the first NT-proBNP or BNP level, then administering the second dose of mavacamten or a pharmaceutically acceptable salt thereof that is greater than the first dose during the second treatment period; and if the second cardiac troponin level is at least 30% less than the first cardiac troponin level or the second NT-proBNP or BNP level is more than 50% greater than the first NT-proBNP or BNP level, then administering the first dose of mavacamten or a pharmaceutically acceptable salt thereof during the second treatment period.

In some embodiments, the first cardiac troponin level is measured before the first treatment period. In some embodiments, the first cardiac troponin level is measured immediately before, or within two weeks before, the first treatment period. In some embodiments, the second cardiac troponin level is measured during the first treatment period. In some embodiments, the second cardiac troponin level is measured at the end of, or within four weeks of the end of, the first treatment period.

In some embodiments, the first dose is from about 1 mg to about 5 mg. In some embodiments, the first dose is about 2.5 mg. In some embodiments, the second dose is from about 2.5 mg to about 10 mg. In some embodiments, the second dose is about 5 mg. In some embodiments, the second dose is about 1.5 times to about 3 times the first dose. In some embodiments, the second dose is about double the first dose.

In some embodiments, the first dose is administered daily during the first treatment period. In some embodiments, the first treatment period is at least two weeks, at least four weeks, at least six weeks, at least eight weeks, at least ten weeks, at least twelve weeks, 4-20 weeks, 10-16 weeks, or about 14 weeks. In some embodiments, the second dose is administered daily during the second treatment period. In some embodiments, the second treatment period is at least two weeks, at least four weeks, at least six weeks, at least eight weeks, at least ten weeks, or at least twelve weeks.

In some embodiments, the subject has prior objective evidence of heart failure as shown by one or more of:

previous hospitalization for heart failure with radiographic evidence of pulmonary congestion;

elevated left ventricular end-diastolic pressure or pulmonary capillary wedge pressure at rest or with exercise;

elevated level of NT-proBNP or BNP; and
echocardiographic evidence of medial E/e' ratio ≥15 or left atrial enlargement together with chronic treatment with a loop diuretic.

In some embodiments, the cardiac troponin is cardiac troponin I (cTnI) or cardiac troponin T (cTnT), high sensitivity cTnI (hs-cTnI). In some embodiments, the elevated troponin level is above the upper limit of normal (ULN). In some embodiments, the ULN is about 0.014 ng/mL for cTnT. In some embodiments, the ULN is about 47 pg/mL for cTnI.

In some embodiments, an elevated E/e' is greater than 10. In some embodiments, an E/e' is the average E/e'. In some embodiments, an elevated E/e' is greater than 13. In some embodiments, an elevated E/e' is greater than 14.

In some embodiments, an elevated BNP is greater than 35 pg/mL. In some embodiments, an elevated NT-proBNP is greater than 125 pg/mL. In some embodiments, an elevated NT-proBNP is greater than 250 pg/mL. In some embodiments, an elevated NT-proBNP is greater than 300 pg/mL. In some embodiments, an elevated T-proBNP is greater than 450 pg/mL. In some embodiments, the subject is 74 years old or younger with NT-proBNP greater than 125 pg/mL. In some embodiments, the subject is 75 years old or older with NT-proBNP greater than 125 pg/mL.

In some embodiments, the subject is suffering from diastolic dysfunction, elevated filling pressure, elevated left ventricular filling pressure, left atrial enlargement, preserved systolic function, or systolic hyper-contractility.

In some embodiments, the subject is suffering from left ventricular hypertrophy (LVH), malignant LVH, angina, ischemia, hypertrophic cardiomyopathy (HCM), or restrictive cardiomyopathy (RCM).

In some embodiments, the subject is suffering from heart failure with preserved ejection fraction (HFpEF).

In some embodiments, the subject is suffering from shortness of breath, fatigue, palpitations (atrial fibrillation), chest pain and discomfort, dizziness, syncope, palpitations, limits on activities of daily living, or edema.

In some embodiments, the subject is suffering from myocardial diastolic dysfunction, elevated LV filing pressure, left ventricular wall hypertrophy, left atrial enlargement, normal or hypercontractility, myocardial injury and fibrosis, or abnormal myocardial energetics.

In some embodiments, the subject is suffering from reduced exercise tolerance, fatigue, tiredness, increased time to recover after exercise, ankle swelling In some embodiments, the subject has a normal or hypercontractile left ventricle ejection fraction (LVEF). In some embodiments, the normal LVEF is between 50-74% or 52-74%.

In some embodiments, the myosin inhibitor is mavacamten or a pharmaceutically acceptable salt thereof.

In some embodiments, the subject experiences a reduction in the risk of a major cardiovascular event, e.g., wherein the major cardiovascular event is selected from the group consisting of death, hospitalization for worsening of the disease, and myocardial infarction.

In some embodiments, the present disclosure provides a method for treating a disease in a subject, comprising administering to the subject in need thereof a therapeutically effective amount of a myosin inhibitor, wherein the subject has a LVEF of greater than 52, and one or more of an elevated level of cardiac troponin, an elevated NT-proBNP or BNP, and elevated E/e'.

In some embodiments, the subject has preserved systolic function or normal or systolic hyper-contractility. In some embodiments, treating the disease with the myosin modulator or inhibitor results in the subject experiencing a reduction in global longitudinal strain. In some embodiments, the subject has diastolic dysfunction.

In some embodiments, treating the disease with the myosin modulator or inhibitor results in the subject experiencing a reduction in left ventricle filling pressures. In some embodiments, the reduction is characterized by an improvement in the average E/e'. In some embodiments, the subject has left ventricle hypertrophy or left atrium size enlargement. In some embodiments, the subject has mild left ventricle hypertrophy.

In some embodiments, treating the disease with the myosin modulator or inhibitor results in the subject experiencing a reduction left ventricular mass, left ventricular wall thickness, interventricular septal thickness, or left ventricular septal thickness. In some embodiments, myosin inhibitor is mavacamten or a pharmaceutically acceptable salt thereof. In some embodiments, the therapeutically effective amount is from about 2.5 mg to about 15 mg. In some embodiments, the therapeutically effective amount is from about 2.5 mg to about 5 mg per day. In some embodiments, the therapeutically effective amount is from about 5 mg to about 7.5 mg per day. In some embodiments, the therapeutically effective amount is from about 7.5 mg to about 15 mg per day.

In some embodiments, the subject has a LVEF of greater than 50%, and one or more of an elevated level of cardiac troponin, an elevated NT-proBNP or BNP, and elevated E/e', wherein the cardiac troponin is cardiac troponin T (cTnT), and/or cardiac cTnI and/or or high sensitivity cTnI (hs-cTnI), wherein elevated E/e' is greater than 10 or 13, or wherein E/e' is the average E/e', wherein BNP is greater than 35 pg/mL, wherein the NT-proBNP is greater than 125 pg/mL or wherein NT-proBNP is greater than 200 or 300 pg/mL.

In some embodiments, the present disclosure provide a method for measuring the cardiac diseases by echocardiogram (ECHO), magnetic resonance imaging (MRI), computed tomography (CT) scan, or cardia catheter.

Also disclosed herein is a method of treating a subject suffering from oHCM comprising administering a myosin modulator to the subject, wherein the subject is eligible for septal reduction therapy (SRT).

In some embodiments, the treatment comprises administering a therapeutically effective amount of the myosin modulator to the subject.

In some embodiments, the treatment lessens the likelihood that the subject will undergo a SRT. In some embodiments, the treatment lessens the short-term likelihood that the subject will undergo SRT. In some embodiments, the treatment eliminates the need for the subject to undergo a SRT.

In some embodiments, the treatment results in a reduction in interventricular septal (IVS) wall thickness. In some embodiments, the treatment results in a reduction in IVS wall thickness of at least 1 mm, at least 2 mm, at least 3 mm, at least 4 mm, or at least 5 mm. In some embodiments, the treatment reduces the interventricular septal (IVS) wall thickness relative to the IVS thickness prior to receiving the treatment. In some embodiments, prior to the administration of the myosin modulator, the subject had an interventricular septal (IVS) wall thickness to 13 mm and has a family history of HCM. In some embodiments, prior to the administration of the myosin modulator, the subject had a interventricular septal (IVS) wall thickness to 15 mm.

In some embodiments, prior to the treatment, the subject has severe dyspnea or chest pain.

In some embodiments, prior to the treatment, the subject is diagnosed with NYHA Class III or IV, or NYHA Class II with exertional symptoms. In some embodiments, the exertional symptoms are exertion-induced syncope or pre-syncope.

In some embodiments, prior to the treatment, the subject has a dynamic LVOT gradient at rest or with provocation of ≥50 mmHg associated with septal hypertrophy. In some embodiments, provocation is determined during a Valsalva maneuver or exercise.

In some embodiments, prior to the treatment, the subject has a LVEF≥60%.

In some embodiments, the treatment results in an improvement in the NYHA Class. In some embodiments, NYHA Class III to Class II, or NYHA Class II to Class I. In some embodiments, the treatment results in an improvement in the KCCQ.

In some embodiments, the myosin modulator is a myosin inhibitor.

In some embodiments, the myosin inhibitor is mavacamten or a pharmaceutically acceptable salt thereof.

In some embodiments, the therapeutically effective amount of mavacamten or a pharmaceutically acceptable salt thereof is from about 2.5 mg to about 15 mg. In some embodiments, the therapeutically effective amount is from about 5 mg to about 7.5 mg per day, or about 7.5 mg to about 15 mg per day. In some embodiments, the therapeutically effective amount is about 5 mg per day. In some embodiments, the therapeutically effective amount is administered once a day for 16 or more weeks. In some embodiments, the therapeutically effective amount is administered once a day for 32 or more weeks. In some embodiments, the therapeutically effective amount is administered once a day for 96 or more weeks. In some embodiments, the therapeutically effective amount of mavacamten or a pharmaceutically acceptable salt thereof is 5 mg per day for 16 or more weeks.

In some embodiments, the subject is optionally evaluated for a dose adjustment at week 4, week 8, week 12, or week 16. In some embodiments, the therapeutically effective amount of mavacamten or a pharmaceutically acceptable salt thereof is 5 mg per day for 32 or more weeks. In some embodiments, the subject is optionally evaluated for a dose adjustment at week 4, week 8, week 12, or week 16, week 20, week 24, week 28, or week 32.

In some embodiments, the therapeutically effective amount of mavacamten or a pharmaceutically acceptable salt thereof is 5 mg per day for 96 or more weeks. In some embodiments, the subject is optionally evaluated for a dose adjustment at week 4, week 8, week 12, or week 16, week 20, week 24, week 28, or week 32, week 44, week 56, week 68, week 80, week 92, week 104, week 116, or week 128.

In some embodiments, each dose adjustment comprises reducing the dose to 2.5 mg or 1 mg per day. In some embodiments, each dose adjustment comprises increasing the dose to 7.5 mg or 15 mg per day.

In some embodiments, the evaluation for the dose adjustment comprises the assessments of one or more of any of: vital signs, body weight, NYHA functional classes, adverse events, concomitant medications, physical examination, KCCQ, resting Valsalva, transthoracic echocardiography, transthoracic echocardiogram, postexercise, Accelerometer, Holter monitor application, Single 12-lead ECG, PK sample, blood chemistry and coagulation, cardiac biomarkers, or exploratory biomarkers.

In some embodiments, the evaluation comprises assessments of one or more cardiac biomarkers. In some embodiments, the one or more cardiac biomarkers comprise NT-proBNP or BNP. In some embodiments, the one or more cardiac biomarkers comprise cardiac troponin. In some embodiments, the cardiac troponin is cardiac troponin I (cTnI) or high sensitivity cTnI (hs-cTnI). In some embodiments, the cardiac troponin is cardiac troponin T (cTnT) or high sensitivity cTnT (hs-cTnT).

In some embodiments, the vital signs comprises temperature, heart rate (HR), respiratory rate, or blood pressure.

In some embodiments, the evaluation comprises analysis of LVOT gradient, left ventricular ejection fraction (LVEF), left ventricular (LV) filling pressures, or left atrium size in the subject.

In some embodiments, the evaluation comprises assessments of changes from the baseline to week 16 in the subject who is treated with mavacamten compared with the subject who is treated with placebo. In some embodiments, the evaluation comprises assessments of changes from baseline to week 16 compared with changes from baseline to week 32 in the subject who is treated with mavacamten. In some embodiments, the evaluation comprises assessments of changes from the baseline to week 32 in the subject who is treated with mavacamten compared with the subject who is treated with placebo from week 1 to week 16 and then is treated with mavacamten from week 17 to week 32.

In some embodiments, the evaluation is to assess changes in NYHA functional classes, in KCCQ-23 scores, in NT-proBNP or BNP, in cardiac troponins, or LVOT gradient in the subject. In some embodiments, the cardiac troponin is cardiac troponin I (cTnI) or high sensitivity cTnI (hs-cTnI). In some embodiments, the cardiac troponin is cardiac troponin T (cTnT), or high sensitivity cTnT (hs-cTnT).

In some embodiments, the evaluation comprises analysis of LVOT gradient and/or LVEF. In some embodiments, the method comprises increasing the dose of mavacamten if the LVOT gradient in the subject is greater than 30 mmHg and the LVEF in the subject is greater than or equal to 50%.

In some embodiments, the subject is reevaluated at week 16, week 32, week 80, and/or week 128 for SRT eligibility. In some embodiments, the evaluation shows the method of any one of claims 1-33 lessens the need of a SRT for the subject. In some embodiments, the evaluation shows the method of any one of claims 1-33 eliminates the need of a SRT for the subject.

In some embodiments, the subject is refractory to standard of care treatment for oHCM. "Refractory" refers to the subject's disease, in this case oHCM, not responding to treatment. In one embodiment, a subject is refractory if the subject, after treatment, remains symptomatic (e.g., NYHA class III or IV) and has an LVOT gradient greater than or equal to 50 mmHg. "Standard of care" treatment refers to the treatment for the disease, in this case oHCM, that is generally used and accepted by medical professionals in the field of medicine. In one embodiment, the standard of care for oHCM comprises administration of a beta blocker, a calcium channel blocker, disopyramide or any combination thereof. In some embodiments, the subject is refractory to treatment of oHCM with a beta blocker, a calcium channel blocker, disopyramide or any combination thereof. In some embodiments, prior to treatment with a myosin inhibitor, or mavacamten or a pharmaceutically acceptable salt thereof, the subject reached their maximum tolerated medical treatment with standard of care oHCM therapy and remained symptomatic NYHA class III or IV with an LVOT gradient greater than or equal to 50 mmHg. In some embodiments, prior to treatment with a myosin inhibitor, or mavacamten or a pharmaceutically acceptable salt thereof, the subject reached their maximum tolerated medical treatment with a beta blocker, a calcium channel blocker, and/or disopyramide and remained symptomatic NYHA class III or IV with an LVOT gradient greater than or equal to 50 mmHg.

In some embodiments, the subject receives adjunctive therapy comprising standard of care treatment for oHCM during the course of treatment with the myosin inhibitor, or mavacamten or pharmaceutically acceptable salt thereof. In some embodiments, the subject receives adjunctive therapy comprising a beta blocker, a calcium channel blocker, disopyramide, or any combination thereof during the course of treatment with the myosin inhibitor, or mavacamten or pharmaceutically acceptable salt thereof.

In some embodiments, the subject having oHCM who is to be treated to lessen the likelihood of SRT is classified as NYHA class IV. In some embodiments, the oHCM is symptomatic oHCM. In some embodiments, the subject having HCM who is to be treated to lessen the likelihood of SRT satisfies the inclusion criteria and exclusion criteria of Example 6.

In some embodiments, provided herein is a method of treating or alleviating shortness of breath in a patient diagnosed with symptomatic, obstructive HCM, the method comprising administering to the patient a therapeutically effective amount of mavacamten or a pharmaceutically acceptable salt thereof once per day for greater than twenty-one weeks.

In some embodiments, shortness of breath is measured by a patient-reported questionnaire.

In some embodiments, the questionnaire comprises two or more questions regarding shortness of breath symptoms of the patient.

In some embodiments, the questionnaire is HCMSQ-SoB.

In some embodiments, the therapeutically effective amount is from about 2.5 mg to about 15 mg per day.

In some embodiments, mavacamten is administered for at least thirty weeks.

In some embodiments, the patient has an LVEF>50%.

In some embodiments, the therapeutically effective amount results in a trough blood plasma concentration of mavacamten in the patient of from about 350 to about 700 ng/mL.

In some embodiments, the therapeutically effective amount results in a post exercise LVOT gradient in the patient of less than about 50 mmHg or less than about 30 mmHg.

In some embodiments, provided herein is a method of increasing the quality of life of a patient diagnosed with symptomatic, obstructive HCM, the method comprising administering to the patient a therapeutically effective amount of mavacamten or a pharmaceutically acceptable salt thereof for at least thirty weeks, wherein the improvement in the quality of life of the patient is measured by an improvement of at least six points in the patient's KCCQ score relative to before treatment with mavacamten or a pharmaceutically acceptable salt thereof.

In some embodiments, the KCCQ score is based on using any one or all of KCCQ-CSS, KCCQ-OSS, or KCCQ-TSS.

In some embodiments, improvement in quality of life is additionally measured by an improvement in shortness of breath.

In some embodiments, improvement in shortness of breath is determined by a questionnaire comprising two or more questions.

In some embodiments, improvement in shortness of breath is determined by HCMSQ-SoB score.

In some embodiments, the patient achieves an improvement of six points in KCCQ score.

In some embodiments, the therapeutically effective amount is from about 2.5 mg to about 15 mg per day.

In some embodiments, the patient has an LVEF>50%.

In some embodiments, the therapeutically effective amount results in a trough blood plasma concentration of mavacamten in the patient of from about 350 to about 700 ng/mL.

In some embodiments, the therapeutically effective amount results in a post exercise LVOT gradient in the patient of less than about 30 mmHg or less than about 50 mmHg.

In some embodiments, provided herein is a method of treating symptomatic obstructive HCM in a patient in need thereof comprising:

- administering to the patient mavacamten or a pharmaceutically acceptable salt thereof at a starting dose of from about 2.5 to about 5 mg per day; and
- titrating the starting dose to a second dose of from about 2.5 to about 15 mg per day;
- wherein the patient achieves one or more of the following:
  - an improvement of at least 1.5 mL/kg/min in peak oxygen consumption (pVO2) and a reduction of one or more class in NYHA Functional Classification;
  - an improvement of 3.0 mL/kg/min or more in pVO2 with no worsening in NYHA Functional Class;
  - a improvement in post-exercise LVOT peak LVOT gradient;
  - at least 1 class improvement in NYHA functional class;
  - a improvement in pVO2;
  - a improvement in KCCQ score;
  - a improvement in HCMSQ score;
  - a post-exercise LVOT peak LVOT gradient<50 mmHg;
  - a post-exercise LVOT peak LVOT gradient<30 mmHg;
  - a improvement in NT-proBNP levels; and
  - a improvement in hs-cTnI levels;

In some embodiments, the patient achieves one or more of the following:

- an improvement in EuroQol five dimensions 5-level questionnaire score;
- an improvement in the Work Productivity and Activity Impairment questionnaire score;
- an improvement in the Patient Global Impression of Change and Patient Global Impression of Severity scores;
- an improvement in daily step count and other accelerometer parameters;

In some embodiments, comprising titrating the starting dose to achieve a trough blood plasma concentration of mavacamten in the patient of from about 350 to about 700 ng/mL.

In some embodiments, comprising titrating the starting dose to achieve a trough blood plasma concentration of mavacamten in the patient of from about 350 to about 700 ng/mL and a Valsalva LVOT gradient in the patient of less than about 30 mmHg.

In some embodiments, the starting dose is 2.5 or 5 mg per day.

In some embodiments, the second dose is 2.5, 5, 10, or 15 mg per day.

In some embodiments, mavacamten is administered daily for at least about 30 weeks.

In some embodiments, the patient to be treated has (a) an oHCM classified as NYHA II or NYHA III, (b) an LVOT peak gradient>50 mmHG as assessed by echocardiography at rest, after Valsalva maneuver, or post-exercise, and (c) an LVEF>55%.

In some embodiments, the patient satisfies the inclusion and/or exclusion criteria listed in Table 7.0 of Example 7.

In some embodiments, titrating the starting dose to a second dose of from about 2.5 to about 15 mg per day comprises titrating the starting dose to a second dose of 2.5 mg per day if Valsalva LVOT gradient in the patient is less than 20 mmHg.

In some embodiments, provided herein is a method of treating symptomatic obstructive HCM in a patient in need thereof comprising:

- administering to the patient mavacamten or a pharmaceutically acceptable salt thereof at a starting dose of from about 2.5 to about 5 mg per day;
- titrating the starting dose to a second dose of from about 2.5 to about 15 mg per day to achieve a Valsalva LVOT gradient in the patient of less than about 30 mmHg;
- wherein the patient achieves one or more of the following:
  - an improvement of at least 1.5 mL/kg/min in peak oxygen consumption (pVO2) and a reduction of one or more class in NYHA Functional Classification;
  - an improvement of 3.0 mL/kg/min or more in pVO2 with no worsening in NYHA Functional Class;
  - an improvement in post-exercise LVOT peak LVOT gradient;
  - at least 1 class improvement in NYHA functional class;
  - an improvement in pVO2;
  - an improvement in KCCQ score;
  - an improvement in HCMSQ score;
  - a post-exercise LVOT peak LVOT gradient<50 mmHg;
  - a post-exercise LVOT peak LVOT gradient<30 mmHg;
  - an improvement in NT-proBNP levels;
  - an improvement in hs-cTnI levels;

In some embodiments, the patient achieves one or more of the following:

- an improvement in EuroQol five dimensions 5-level questionnaire score;
- an improvement in the Work Productivity and Activity Impairment questionnaire score;
- an improvement in the Patient Global Impression of Change and Patient Global Impression of Severity scores;
- an improvement in daily step count and other accelerometer parameters;

In some embodiments, comprising titrating the starting dose to achieve a Valsalva LVOT gradient in the patient of less than about 30 mmHg and a trough blood plasma concentration of mavacamten in the patient of from about 350 to about 700 ng/mL.

In some embodiments, the starting dose is 2.5 or 5 mg per day.

In some embodiments, the second dose is 2.5, 5, 10 or 15 mg per day.

In some embodiments, mavacamten is administered daily for at least about 30 weeks.

In some embodiments, the patient to be treated satisfies the inclusion criteria in Table 7.0 of Example 7.

In some embodiments, the patient to be treated satisfies the exclusion criteria in Table 7.0 of Example 7.

In some embodiments, titrating the starting dose to a second dose of from about 2.5 to about 15 mg per day comprises titrating the starting dose to a second dose of 2.5 mg per day if Valsalva LVOT gradient in the patient is less than 20 mmHg.

In some embodiments, provide herein is a method of treating HCM in a patient in need thereof comprising the steps of:

(a) administering to the patient a therapeutically effective amount of mavacamten or a pharmaceutically acceptable salt thereof once per day;

(b) temporarily discontinuing administration of mavacamten or a pharmaceutically acceptable salt thereof when the ejection fraction in the patient drops below a threshold ejection fraction; and (c) resuming administration to the patient of a therapeutically effective amount of mavacamten or a pharmaceutically acceptable salt thereof once per day.

In some embodiments, the threshold ejection fraction is 50%, 52%, or 55%. In some embodiments, the threshold ejection fraction is 50%.

In some embodiments, step (b) of the method further comprises temporarily discontinuing administration of mavacamten or pharmaceutically acceptable salt thereof for a period of from about 1 to about 8 weeks when the ejection fraction in the patient drops below the threshold ejection fraction.

In some embodiments, step (c) of the method further comprises resuming administration of a therapeutically effective amount of mavacamten or a pharmaceutically acceptable salt thereof to the patient once per day for at least about 4 weeks.

In some embodiments, the therapeutically effective amount is from about 2.5 mg to about 15 mg per day.

In some embodiments, the therapeutically effective amount results in a trough blood plasma concentration of mavacamten in the patient of from about 350 to about 700 ng/mL.

In some embodiments, the therapeutically effective amount results in a Valsalva LVOT gradient in the patient of less than about 30 mmHg.

In some embodiments, subsequent to resuming administration according to step (c), the patient achieves one or more of the following:

- an improvement of at least 1.5 mL/kg/min in peak oxygen consumption (pVO2) and a reduction of one or more class in NYHA Functional Classification;
- an improvement of 3.0 mL/kg/min or more in pVO2 with no worsening in NYHA Functional Class;
- an improvement in post-exercise LVOT peak LVOT gradient;
- at least 1 class improvement in NYHA functional class;
- an improvement in pVO2;
- an improvement in KCCQ score;
- an improvement in HCMSQ score;
- a post-exercise LVOT peak LVOT gradient<50 mmHg;
- a post-exercise LVOT peak LVOT gradient<30 mmHg;
- an improvement in NT-proBNP levels;
- an improvement in hs-cTnI levels;

In some embodiments, the patient achieves one or more of the following:

- an improvement in EuroQol five dimensions 5-level questionnaire score;
- an improvement in the Work Productivity and Activity Impairment questionnaire score;
- an improvement in the Patient Global Impression of Change and Patient Global Impression of Severity scores;
- an improvement in daily step count and other accelerometer parameters;

In some embodiments, the patient achieves an improvement in post-exercise LVOT peak LVOT gradient and at least 1 class improvement in NYHA functional class.

In some embodiments, the patient achieves a post-exercise LVOT peak LVOT gradient of <50 mmHg and at least 1 class improvement in NYHA functional class In some embodiments, the patient achieves a post-exercise LVOT peak LVOT gradient of <30 mmHg and at least 1 class improvement in NYHA functional class.

DETAILED DESCRIPTION

Definitions

Figure 1A:
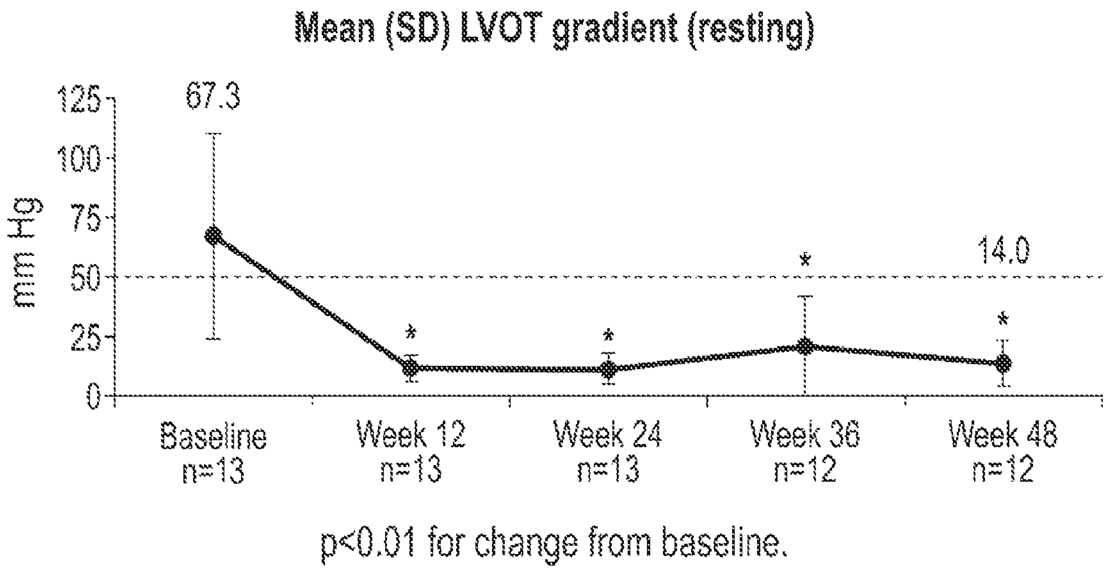
FIG. 1A is a plot of Mean LVOT gradient (resting) for the subjects in Example 1.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The following documents are incorporated by reference in their entirety:

The American Society of Echocardiography, Recommendations for Cardiac Chamber Quantification in Adults: A Quick Reference Guide from the ASE Workflow and Lab Management Task Force, July 2018

Lang et al., Recommendations for Cardiac Chamber Quantification by Echocardiography in Adults: An Update from the American Society of Echocardiography and the European Association of Cardiovascular Imaging, Journal of the American Society of Echocardiography, January 2015

Nagueh et al., Recommendations for the Evaluation of Left Ventricular Diastolic Function by Echocardiography: An Update from the American Society of Echocardiography and the European Association of Cardiovascular Imaging, Journal of the American Society of Echocardiography, 2016; 29:277-314

Caballero et al., Echocardiographic reference ranges for normal cardiac Doppler data: results form the NORRE Study, European Heart Journal—Cardiovascular Imaging (2015) 16, 1031-1041

Jozine M. ter Maaten et al., Connectin heart failure with preserved ejection fraction and renal dysfunction: the role of endothelial dysfunction and inflammation, European Journal of Heart Failure (2016) 18, 588-598

ATS/ACCP Statement on Cardiopulmonary Exercise Testing, American Thoracic Society/American College of Chest Physicians, Nov. 1, 2001

Zaid et al., Pre- and Post-Operative Diastolic Dysfunction in Patients with Valvular Heart Disease, Journal of the American College of Cardiology, 2013, 62(21), 1922-1930

Gupta et al., Racial differences in circulating natriuretic peptide levels: the atherosclerosis risk in communities study, Journal of the American Heart Association, 2015; 4:e001831

Eugene Braunwald, Cardiomyopathies: An Overview, Circ Res. 2017; 121:711-721

Towbin and Jefferies, Cardiomyopathies Due to Left Ventricular Noncompaction, Mitochondrial and Storage Diseases and Inborn Errors of Metabolism, Circ Res. 2017; 121:838-854

Cirino and Ho, Hypertrophic Cardiomyopathy Overview. 2008. In: Adam et al., eds., GeneReviews®, Seattle (WA): University of Washington, Seattle; 1993-2020.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The terms "a" or "an," as used in herein means one or more.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value. In some embodiments, "about" means the specified value.

As used herein, "treatment" or "treating," or "palliating" or "ameliorating" or "reducing" are used interchangeably herein. These terms refer to an approach for obtaining beneficial or desired results including but not limited to a therapeutic benefit. By therapeutic benefit means eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. Treatment includes causing the clinical symptoms of the disease to slow in development by administration of a composition; suppressing the disease, that is, causing a reduction in the clinical symptoms of the disease; inhibiting the disease, that is, arresting the development of clinical symptoms by administration of a composition after the initial appearance of symptoms; and/or relieving the disease, that is, causing the regression of clinical symptoms by administration of a composition after their initial appearance. For example, certain methods described herein treat hypertrophic cardiomyopathy (HCM) by decreasing or reducing the occurrence, or progression of HCM; or treat HCM by decreasing a symptom of HCM. Symptoms of, or test results indicating HCM would be known or may be determined by a person of ordinary skill in the art and may include, but are not limited to, shortness of breath (especially during exercise), chest pain (especially during exercise), fainting (especially during or just after exercise), sensation of rapid, fluttering or pounding heartbeats, atrial and ventricular arrhythmias, heart murmur, hypertrophied and non-dilated left ventricle, thickened heart muscle, thickened left ventricular wall, elevated pressure gradient across left ventricular outflow tract (LVOT), and elevated post-exercise LVOT gradient.

"Patient" or "subject" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, cats, monkeys, goat, sheep, cows, deer, and other non-mammalian animals. In some embodiments, a patient, subject or subject in need thereof is a human.

As used herein, "administration" of a disclosed compound encompasses the delivery to a subject of a compound as described herein, or a prodrug or other pharmaceutically acceptable derivative thereof, using any suitable formulation or route of administration, e.g., as described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). Efficacy can also be expressed as "-fold" increase or decrease. For example, a therapeutically effective amount can have at least a 1.2-fold, 1.5-fold, 2-fold, 5-fold, or more effect over a control.

"Elevated level of troponin" or "elevated troponin level" refers to a concentration of a cardiac troponin (cTn) complex protein in a blood sample that exceeds the $99^{th}$ percentile of a healthy reference population concentration. The upper limit of normal (ULN) is typically most precisely determined by the individual assay or detection approach. Cardiac troponins form a trimeric complex (T:I:C) bound to the thin filament. According to this invention, the cardiac troponin complex or its variations in protein constituents comprising the complex to be measured in a blood sample is preferred through the detection of cardiac troponin I (cTnI) or cardiac troponin T (cTnT). In one embodiment, the blood sample is a plasma or a serum sample. In one embodiment, the elevated troponin level is detected by immunoassay.

In another embodiment, the elevated cTnI concentration is above 0.01 ng/ml, above 0.03 ng/ml or is above 0.4 ng/ml. In another embodiment, the immunoassay has a Limit of Quantification (LoQ) of < or =10 pg/ml. LoQ refers to the lowest amount of analyte in a sample that can be accurately quantified with bias≤10% and imprecision≤10% CV. In another embodiment, the immunoassay has a limit of detection (LOD)≤0.010 ng/ml with a precision of 10% coefficient of variation (CV). In another embodiment, elevated troponin level is above the upper limit of normal (ULN), wherein the ULN is 0.014 ng/mL for cTnT or 47 pg/mL for cTnI. In another embodiment, the lower limit of quantification (LLOQ) for cTnT is 0.003 ng/ml and the LLOQ for cTnI is 2.5 pg/ml. In one embodiment, "high sensitivity" for a cTnT or cTnI assay refers to a lower limit of quantification (LLOQ) for cTnT of 0.003 ng/ml and a LLOQ for cTnI of 2.5 pg/ml, respectively.

Brain natriuretic peptide (BNP) is a natriuretic hormone initially identified in the brain but released primarily from the heart, particularly the ventricles. Cleavage of the 108 amino acid prohormone proBNP produces biologically active 32 amino acid BNP as well as biologically inert 76 amino acid N-terminal pro-BNP (NT-proBNP). The biologically active BNP, proBNP and NT-proBNP can each be measured in the blood. BNP is released in response to myocyte stretching caused by ventricular volume expansion or pressure overload "Elevated proBNP level", "elevated NT-proBNP level", "elevated level of pro-BNP," and "elevated level of NT-ProBNP" are interchangeable and refer to a concentration of a NT-proB-Type Natriuretic Peptide (NT-proBNP) in a blood sample that is, >125 pg/ml. In some embodiments, elevated proBNP level is >300 pg/ml. In some embodiments, elevated proBNP level is >200 pg/ml. In some embodiments, the elevated NT-proBNP is >750 pg/mL for a subject who has atrial fibrillation or flutter.

"Elevated adjusted NT-proBNP level," "elevated adjusted NT-proBNP," or "elevated adjusted level of pro-BNP" refers to a concentration of NT-proBNP in a blood sample that is higher than normal. In some embodiments, the upper limit of normal (ULN) for any particular assay is provided in its product specification. In some embodiments, such ULN is 125 pg/ml. The ULN can vary based on patient characteristics, such as race, body-mass index (BMI), age and gender. For example, African-Americans may have a lower ULN than 125 pg/ml. Studies indicate that there may be an inverse relationship between BMI and NT-proBNP levels. The ULN for NT-proBNP for older adults tends to increase with age. Other studies indicate that the NT-proBNP levels in healthy females under 80 years old may be higher than healthy males of the same age. In some studies, patients with atrial fibrillation have higher NT-proBNP levels (e.g., >750). In some embodiments, the elevated NT-proBNP level is an elevated adjusted NT-proBNP level.

"Elevated BNP Level" or "elevated BNP" refers to a concentration of brain natriuretic peptide in a blood sample that is higher than normal. In some embodiments, elevated BNP is higher than the upper limit of normal as provided by a given assay. The upper limit of normal (ULN) is typically most precisely determined by the individual assay or detection approach. In some embodiments, the elevated BNP level is >100 pg/ml.

E/e' refers to the ratio between early mitral inflow velocity and mitral annular early diastolic velocity (E/e'). E/e' is an echocardiogram (ECHO) surrogate measure of elevated left ventricular filling pressure. E/e' can be measured and calculated as the medial or septal E/e' ratio, the lateral E/e' ratio, or as the average E/e' ratio. In some embodiments, E/e' is $E/e'_{average}$. Elevated E/e' refers to a ratio value that is higher than the upper limit of normal. In one embodiment, the elevated E/e' is >14. In one embodiment, the elevated E/e' is $E/e'_{average}$>14. In another embodiment, elevated E/e' is $E/e'_{septal}$>15. In another embodiment, elevated E/e' is $E/e'_{lateral}$>13, or in another embodiment >12.

"Desired clinical state" refers to a better clinical state measured by any one or combination of the measures selected from the group consisting of: normal LVEF (52-74%), normal LVOT (resting gradient, Valsalva gradient or post-exercise gradient of <30 mmHg), normal Interventricular Septal Thickness (IVS) (6-10 mm), normal LV Posterior Wall Thickness (6-10 mm), normal left ventricular mass or mass index, normal LAVI (16-34 mL/$m^2$), normal Lateral E/e' (<8), normal NT-proBNP (<125 pg/ml); normal KCCQ Overall Symptom Score; and normal cTnI levels (below elevated troponin levels).

"Stable" refers to the determination by a physician that the disease is neither decreasing nor increasing in extent or severity over a period of time.

A "subject at risk of developing HCM or LVH" is an individual that may be asymptomatic or have a NYHA I classification. Such at risk individual additionally has any one or combination of the following: elevated troponin level, a predisposition to develop HCM or LVH, a symptom of a HCM or LVH, or clinical suspicion of early LV hypertrophy or HCM. In one embodiment, the patient is at risk of developing nHCM.

"Predisposition to develop HCM or LVH" refers to the predisposition to develop HCM or LVH in an subject either due to (a) a genetic predisposition wherein the subject has a mutation associated with HCM or LVH or (b) a familial predisposition wherein the subject's family has a history of developing HCM or LVH but a genetic linkage for the HCM or LVH is not known. There are eight cardiac sarcomere genes that most commonly cause HCM (MYH7, MYBPC3, TNNT2, TNNI3, TPM1, ACTC, MLC2 and MLC3), and two glycogen metabolism genes (named PRKAG2 and LAMP2) cause a condition that mimics HCM, also causing LVH. By analyzing five genes, MYH7, MYBPC3, TNNT2, TNNI3, and TPM1, a mutation can be found in 50-60% of individuals who are thought to have HCM. By looking at three additional genes: ACTC, MLC2 and MLC3, a mutation can be detected in an additional 5-10% of subjects with HCM. Altogether, current genetic testing for HCM can detect a mutation in about 55-70% of people with a suspected diagnosis of HCM.

"Lessen the likelihood that a subject will undergo septal reduction therapy (SRT)," or the like, refers to a clinically significant decrease in the likelihood that a subject with undergo SRT when the subject undergoes treatment as compared to lack of treatment (e.g., placebo). In some embodiments, the decrease in likelihood that the subject will undergo septal reduction therapy is a decrease of at least 5%, at least 10%, at least 15%, at least 20%, at least 25%, at least 30%, at least 40%, at least 50%, or at least 75%. In one embodiment, lessening the likelihood that a subject will undergo SRT refers to (1) a reduction in the desire of a patient to proceed with SRT, and/or (2) a resultant change in SRT guideline eligibility such that the patient is no longer eligible to receive SRT.

"Lessen the short-term likelihood that a subject will undergo septal reduction therapy (SRT)," or the like, refers to a clinically significant decrease in the likelihood that a subject with undergo SRT within one year of the start of treatment when the subject undergoes treatment as compared to lack of treatment (e.g., placebo). In some embodiments, the decrease in likelihood that the subject will undergo septal reduction therapy within one year of the start of treatment is a decrease of at least 5%, at least 10%, at least 15%, at least 20%, at least 25%, at least 30%, at least 40%, at least 50%, or at least 75%. In some embodiments, the short-term likelihood is evaluated after 16 weeks of treatment. In some embodiments, the short-term likelihood is evaluated after 32 weeks of treatment. In some embodiments, the lessened likelihood that a subject will undergo SRT is maintained across the time period from 16 weeks to 32 weeks.

As used herein, "smaller dose of a β blocker" refers to a smaller amount of a β blocker drug given to an individual in a single administration, with or without a corresponding reduction in frequency of dosing. For example, if the individual was previously receiving 10 mg once per day of a β blocker, some examples of a smaller dose of a β blocker would be 1, 3, 5, 7 or 9 mg once per day; some other examples of a smaller dose of a β blocker would be 1, 3, 5, 7, or 9 mg once every other day.

As used herein, "less frequent dose of a β blocker" refers to less frequent administration of a β blocker drug given to an individual, with or without a corresponding reduction in the amount of β blocker drug given in a single administration. For example, if the individual was previously receiving 10 mg once per day of a β blocker, some examples of a less frequent dose of a β blocker would be 10 mg once every other day or 10 mg once per week; some other examples of a less frequent dose of a β blocker would be 5 mg once every other day or 5 mg once per week.

As used herein, "undergoing β blocker therapy" refers to an individual that has been receiving one or more β blockers prior to beginning treatment with a myosin modulator or myosin inhibitor (e.g., mavacamten). An individual undergoing β blocker therapy may continue with the same β blocker therapy upon beginning treatment with a myosin modulator or myosin inhibitor. The individual may alternatively continue with β blocker therapy, but which is modified (e.g., smaller dose or less frequent dosing) upon beginning treatment with a myosin modulator or myosin inhibitor. Also, as another alternative, the individual may discontinue β blocker therapy upon beginning treatment with a myosin modulator or myosin inhibitor.

Myosin Inhibitors

In some embodiments, a myosin inhibitor is a compound of formula (I):

(I)

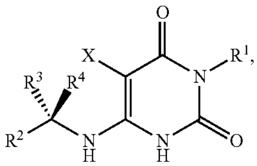

or pharmaceutically acceptable salt thereof, wherein $R^1$ is $C_{1-8}$ alkyl, $C_{3-8}$ cycloalkyl, or a phenyl, wherein $R^1$ is optionally substituted with one or two halo;

$R^2$ is phenyl optionally substituted with one or two halo;

$R^3$ is $C_{1-8}$ alkyl or $C_{3-8}$ cycloalkyl, wherein each $R^3$ is optionally substituted with halo, hydroxyl or $C_{1-2}$ alkoxy;

$R^4$ is H; and

X is H.

In some embodiments, a myosin inhibitor of formula (I) or a pharmaceutically acceptable salt thereof is selected from group (I) consisting of:

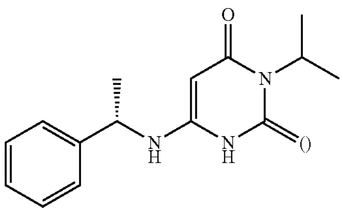
,
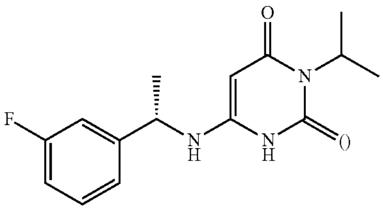
,
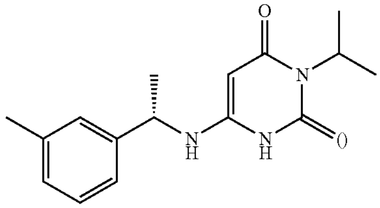
,
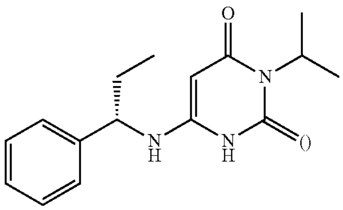
,
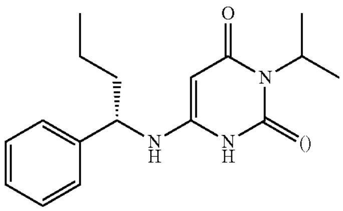
,
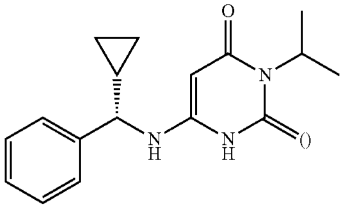
,
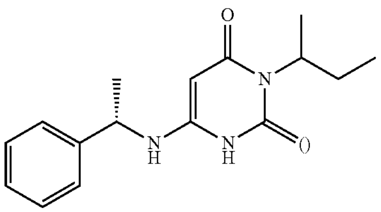
,
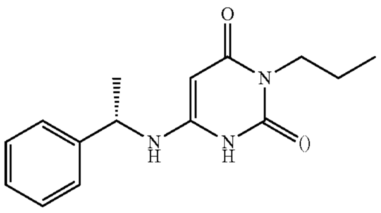
, -continued

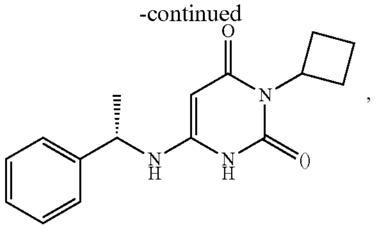

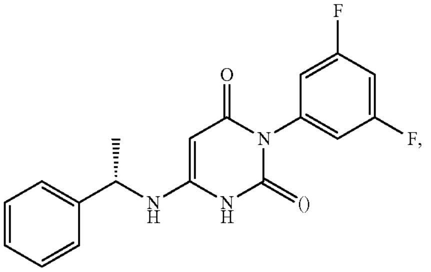

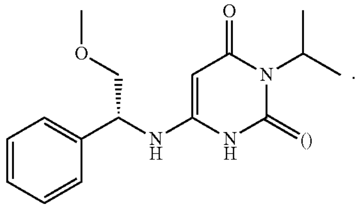

In some embodiments, a myosin inhibitor of formula (I) is mavacamten or a pharmaceutically acceptable salt thereof having the following structure:

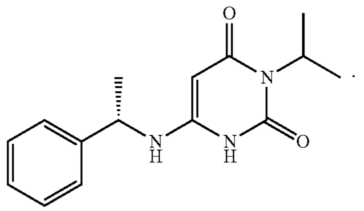

mavacamten

Mavacamten is also known as MYK-461. Its chemical name is (S)-3-Isopropyl-6-((1-phenylethyl)amino)pyrimidine-2, 4(1H,3H)-dione or 6-[[(1S)-1-phenylethyl]amino]-3-propan-2-yl-1H-pyrimidine-2,4-dione.

In some embodiments, a myosin inhibitor of formula (I) is MYK-581 or a pharmaceutically acceptable salt thereof having the following structure.

MYK-581

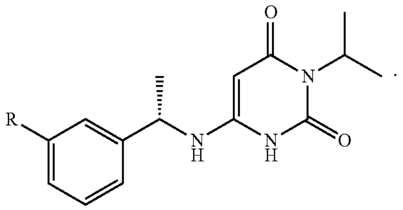

MYK-581's chemical name is (S)-6-((1-(3-fluorophenyl)ethyl)amino)-3-isopropylpyrimidine-2,4(1H,3H)-dione.

Myosin inhibitors of formula (I), including the compounds of group (I), mavacamten, or MYK-581, or a pharmaceutically acceptable salt thereof, can be obtained according to the production methods described in U.S. Pat. No. 9,181,200, which is incorporated herein by reference in its entirety and for all purposes.

In some embodiments, a myosin inhibitor is a compound of formula (II):

(II)

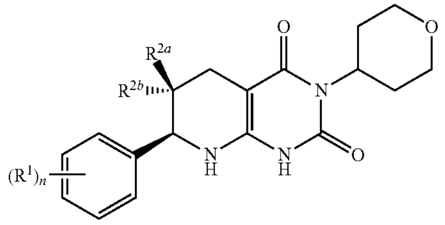

or pharmaceutically acceptable salt thereof, wherein $R^1$ is fluoro, chloro, $C_{1-4}$ alkyl, $C_{1-4}$ haloalkyl, $C_{1-4}$ alkoxy, $C_{1-4}$ haloalkoxy, or $C_{2-4}$ alkynyl, wherein at least one $R^1$ is fluoro; and one of $R^{2a}$ and $R^{2b}$ is fluoro and the other of $R^{2a}$ and $R^{2b}$ is H.

In some embodiments, a myosin inhibitor of formula (II) or a pharmaceutically acceptable salt thereof is selected from group (II) consisting of:

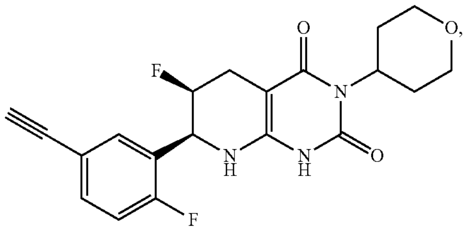

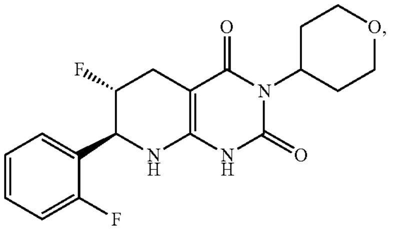

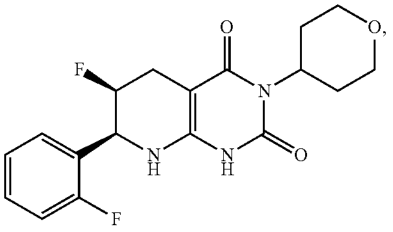

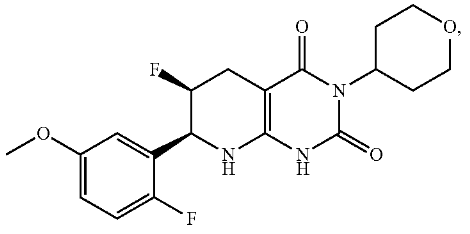

-continued

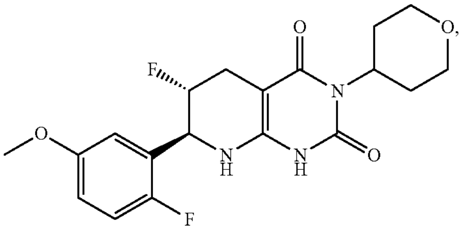

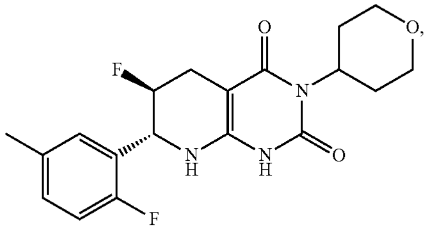

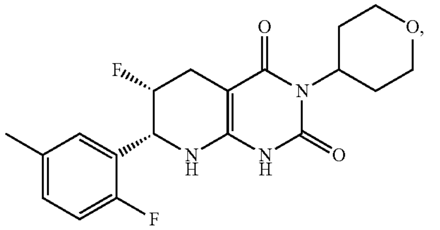

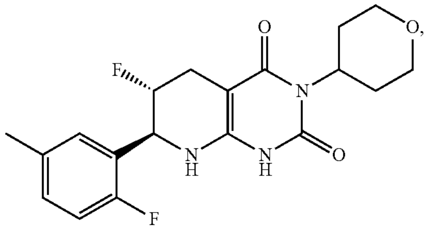

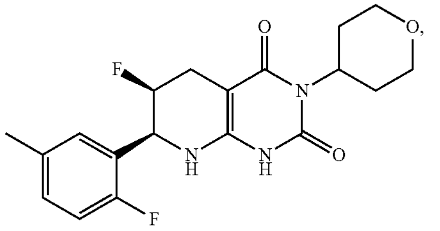

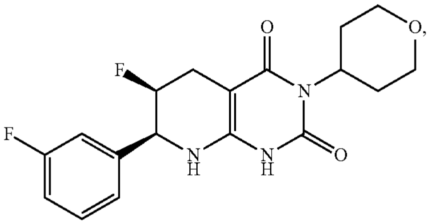

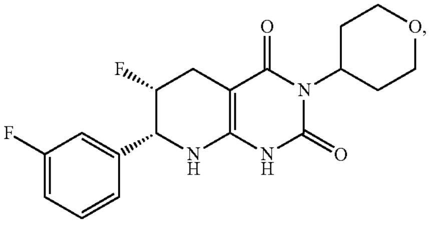

-continued

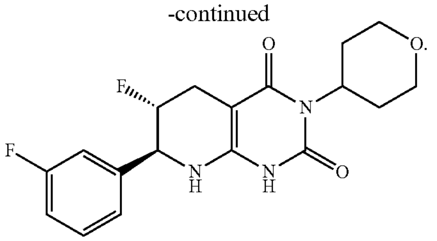

Myosin inhibitors of formula (II), including the compounds of group (II), or a pharmaceutically acceptable salt thereof, can be obtained according to the production methods described in International Application Number PCT/US2019/058297, filed on Oct. 29, 2019, which is incorporated herein by reference in its entirety and for all purposes.

In some embodiments, a myosin inhibitor is a compound of formula (III):

(III)

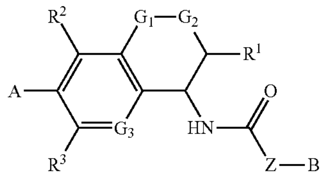

or pharmaceutically acceptable salt thereof, wherein $G_1$ is —$CR^4R^5$— or —O—;

$G_2$ is a bond or —$CR^6R^7$—;

$G_3$ is —$CR^8$— or —N—;

$R^1$, $R^3$, $R^4$, $R^5$, $R^6$, $R^7$, and $R^8$ are each independently H, $C_1$-$C_6$ alkyl, halo, or hydroxyl;

$R^2$ is H, $C_2$-$C_6$ alkyl, halo, or hydroxyl;

Z is a bond, $C_1$-$C_6$ alkyl, —O—, —N($R^9$)—, —$R^XO$—, —$OR^Y$, or —$R^ZS$—;

$R^9$ is H, $C_1$-$C_6$ alkyl, or cycloalkyl;

A is selected from the group consisting of substituted $C_2$ alkynyl, unsubstituted $C_2$ alkynyl, substituted phenyl, unsubstituted phenyl, and 5- or 6-membered heteroaryl comprising at least one annular N atom, wherein the 5- or 6-membered heteroaryl is unsubstituted or substituted with one or more $R^{10}$ substituents:

each $R^{10}$ is independently substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocycloalkyl, or —C(O)$OR^a$;

B is selected from the group consisting of H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents;

each $R^{11}$ is independently selected from the group consisting of substituted or unsubstituted heterocycloalkyl, substituted or unsubstituted heteroaryl, substituted or unsubstituted cycloalkyl, substituted or unsubstituted aryl, unsubstituted $C_1$-$C_6$ alkyl, $C_1$-$C_6$ alkyl substituted with one or more $R^{12}$ substituents, substituted or unsubstituted $C_2$-$C_6$ alkenyl, substituted or unsubstituted $C_2$-$C_6$ alkynyl, halo, —$OR^b$, —C(O)$R^c$, —C(O)$OR^d$, oxo, and —$NR^eR^f$;

each $R^{12}$ is independently selected from the group consisting of halo, —$OR^b$, —C(O)$R^g$, —C(O)$OR^h$, and —C(O)$NR^iR^j$;

each $R^a$, $R^b$, $R^c$, $R^d$, $R^e$, $R^f$, $R^g$, $R^h$, $R^i$, and $R^j$ is independently H or $C_1$-$C_6$ alkyl; and $R^X$, $R^Y$, and $R^Z$ are each $C_1$-$C_6$ alkyl.

In some embodiments, a myosin inhibitor of formula (III) or a pharmaceutically acceptable salt thereof is selected from group (III) consisting of:

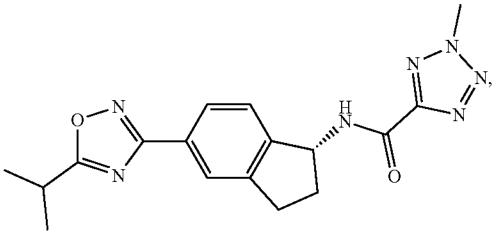
,

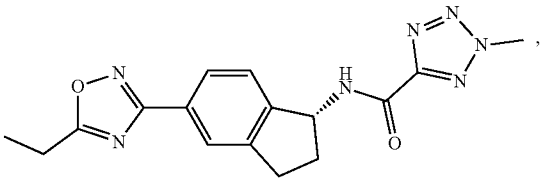
,

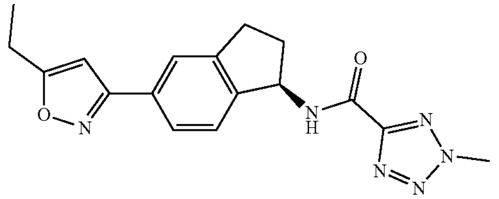
,

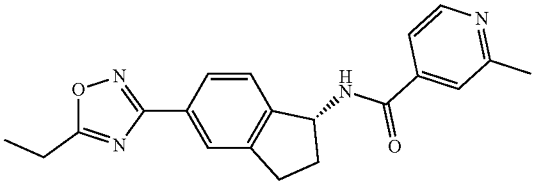
,

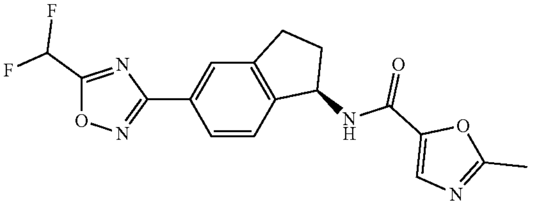
,

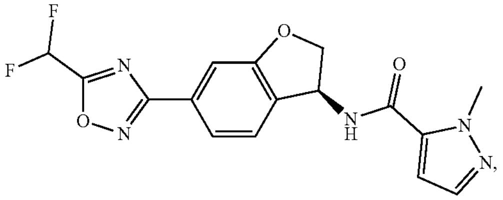
,

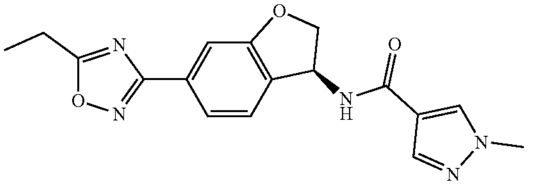
,

-continued

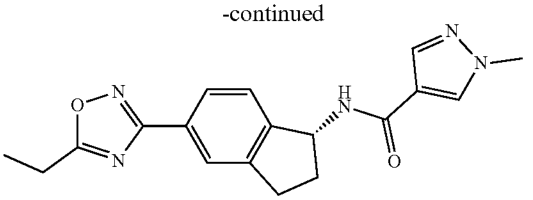
,

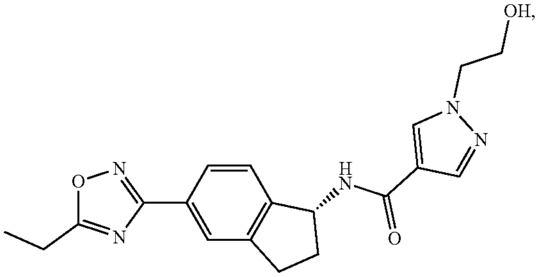
,

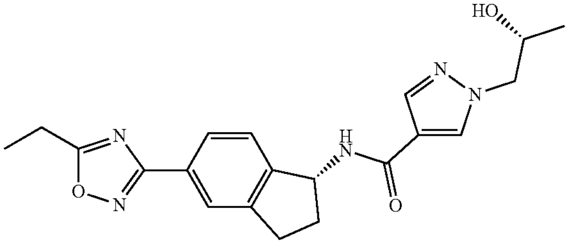
.

Myosin inhibitors of formula (III), including the compounds of group (III), or a pharmaceutically acceptable salt thereof, can be obtained according to the production methods described in International Publication Number WO 2019/144041, published on Jul. 25, 2019, which is incorporated herein by reference in its entirety and for all purposes.

In some embodiments, myosin inhibitors include the compounds disclosed in PCT patent applications, published as WO2020/005887, WO2020/005888, WO2020/047447, which is incorporated herein by reference in its entirety and for all purposes.

In some embodiments, a compound of formulas (I), (II), (III), and/or a compound of groups (I), (II), (III), and/or mavacamten, and/or MYK-581, is administered orally.

In some embodiments, a compound of formulas (I), (II), (III), and/or a compound of groups (I), (II), (III), and/or mavacamten, and/or MYK-581, is administered in a unit dosage.

In some embodiments, mavacamten and/or MYK-581 is administered at a daily dosage amount of 1 mg, 2 mg, 2.5 mg, 5 mg, 7.5 mg, 10 mg, or 15 mg.

In some embodiments, mavacamten and/or MYK-581 is administered daily for 4 weeks, 8 week, 12 weeks, 18 weeks, 24 weeks, 30 weeks, 36 weeks, 48 weeks, or 56 weeks at a daily dosage amount of 1 mg, 2 mg, 2.5 mg, 5 mg, 7.5 mg, 10 mg, or 15 mg.

In some embodiments, mavacamten and/or MYK-581 is administered daily at a starting treatment dosage of 2.5 mg per day and optionally increased to 5 mg per day if certain conditions are met.

In some embodiments, mavacamten and/or MYK-581 is chronically administered daily at least one year, two year, three year, more than five year, or as long as determined by a physician, at a daily dosage amount of 1 mg, 2 mg, 2.5 mg, 5 mg, 7.5 mg, 10 mg, or 15 mg as a maintenance therapy.

In some embodiments, daily dosage in a maintenance therapy comprising mavacamten is less than 7.5 mg.

In some embodiments, daily dosage in a maintenance therapy comprising mavacamten is less than 5 mg.

In some embodiments, daily dosage in a maintenance therapy comprising mavacamten is between 2 mg and 2.5 mg.

The term "maintenance therapy" refers to a therapeutic regimen that is designed to help a primary treatment succeed. For example, maintenance therapy may be given to people who have completely or partially restored cardiac functions after the primary treatment in an effort to prevent, delay, or reduce the likelihood of disease recurrence or progression. Maintenance therapy can be provided for any length of time, including extended time periods up to the life-span of the subject. Maintenance therapy can be provided after primary treatment or in conjunction with additional therapies. Dosages used for maintenance therapy can vary and can include low-intensity dosages as compared to dosages used for primary treatment.

The term "primary therapy" refers to the starting treatment given to a subject based upon the diagnosis of the cardiac dysfunction in the subject.

In some embodiments, the therapeutically effective amount of the starting treatment of mavacamten and/or MYK-581 is about 5 mg, 7.5 mg, 10 mg, or 15 mg.

In some embodiments, the therapeutically effective amount of mavacamten and/or MYK-581 at daily dosage of 5 mg, 7.5 mg, 10 mg, or 15 mg is sufficient to lower a post-exercise or resting LVOT gradient to less than 30 mmHg (e.g., about 29, 28, 27, 26, 25, 24, 23, 22, 21, 20, 19, 18, 17, 16, 15, 14, 13, 12, 11, 10, 9, 8, 7, 6, 5 mmHg). Post-exercise (stress) gradient LVOT can be measured by any methods known in the art.

In some embodiments, the therapeutically effective amount of mavacamten, and/or MYK-581 at a daily dosage amount of 5 mg, 7.5 mg, 10 mg, or 15 mg is sufficient to improve, stabilize or delay worsening in accordance with New York Heart Association (NYHA) functional classification of subjects.

The NYHA functional classification grades the severity of heart failure symptoms as one of four functional classes. The NYHA functional classification is widely used in clinical practice and in research because it provides a standard description of severity that can be used to assess response to treatment and to guide management. The NYHA functional classification based on severity of symptoms and physical activity are:

- Class I: No limitation of physical activity. Ordinary physical activity does not cause undue breathlessness, fatigue, or palpitations
- Class II: Slight limitation of physical activity. Comfortable at rest, but ordinary physical activity results in undue breathlessness, fatigue, or palpitations.
- Class III: Marked limitation of physical activity. Comfortable at rest, but less than ordinary physical activity results in undue breathlessness, fatigue, or palpitations.
- Class IV: Unable to carry on any physical activity without discomfort. Symptoms at rest can be present. If any physical activity is undertaken, discomfort is increased.

In some embodiments, the NYHA functional classification, after administration of a compound of formulas (I), (II), (III), and/or a compound of groups (I), (II), (III), and/or mavacamten, and/or MYK-581, is reduced from class IV to class III, from class IV to class II, or from class IV to class I. In some embodiments, the NYHA functional classification is reduced from class III to class II. In some embodiments, the NYHA functional classification is reduced from class III to class I. In some embodiments, the NYHA functional classification is reduced from class II to class I.

In some embodiments, the therapeutically effective amount of a compound of formulas (I), (II), (III), and/or a compound of groups (I), (II), (III), and/or mavacamten, and/or MYK-581 improves, stabilizes or delays worsening in New York Heart Association (NYHA) functional classification of subjects.

In some embodiments, the therapeutically effective amount of a compound of formulas (I), (II), (III), and/or a compound of groups (I), (II), (III), and/or mavacamten, and/or MYK-581 improves peak $VO_2$.

In some embodiments, the therapeutically effective amount of a compound of formulas (I), (II), (III), and/or a compound of groups (I), (II), (III), and/or mavacamten, and/or MYK-581 improves $VE/VCO_2$ or $VE/VCO_2$ slope. In some embodiments, the subject has a $VE/VCO_2$ of 34 or above. In some embodiments, the improvement comprises reduction of $VE/VCO_2$ to 34 or below.

In some embodiments, the therapeutically effective amount of a compound of formulas (I), (II), (III), and/or a compound of groups (I), (II), (III), and/or mavacamten, and/or MYK-581 reduces (e.g., by a statistically significant amount or percentage) the level of NT-proBNP or BNP in a subject.

In some embodiments, the therapeutically effective amount of a compound of formulas (I), (II), (III), and/or a compound of groups (I), (II), (III), and/or mavacamten, and/or MYK-581 reduces (e.g., by a statistically significant amount or percentage) the level of cardiac troponin (e.g., cTnI, cTnT, hs-cTnI, or hs-cTnT) in a subject.

In some embodiments, the method of treating a subject with a myosin modulator (e.g., mavacamten), as described herein, results in an improvement in one or more clinical endpoints, e.g., one or more functional endpoints or one or more outcome endpoints. In some embodiments, the improved clinical endpoint is a symptom selected from the group consisting of shortness of breath (e.g., as measured by a change in dyspnea index), fatigue (e.g., as measured by a change in peak $VO_2$ or NYHA class), palpitations (e.g., as measured by a change in atrial fibrillation), chest discomfort, edema, and premature mortality, or any combination thereof. In some embodiments, the improved clinical endpoint is a functional endpoint selected from the group consisting of peak $VO_2$, $VE/VCO_2$, $VE/VCO_2$ slope, six-minute walk test, KCCQ subscores, Canadian Cardiovascular Society chest pain score, and Seattle angina score, or any combination thereof. In some embodiments, the improved clinical endpoint is an outcome endpoint selected from the group consisting of reduction in mortality, reduction in hospitalization or rehospitalization, reduction in major adverse cardiovascular events (MACE), reduction in atrial fibrillation, and reduction in atrial fibrillation embolic phenomenon, or any combination thereof. In some embodiments, the improvement is a change (e.g., increase or decrease) from baseline, either in percentage or in amount. In other embodiments, the improvement is achievement of an absolute threshold.

In some embodiments, the therapeutically effective amount of a compound of formulas (I), (II), (III), and/or a compound of groups (I), (II), (III), and/or mavacamten, and/or MYK-581 improves, stabilizes or delays worsening in accordance with Kansas City Cardiomyopathy Questionnaire (KCCQ) score.

In some embodiments, the therapeutically effective amount of a compound of formulas (I), (II), (III), and/or a compound of groups (I), (II), (III), and/or mavacamten, and/or MYK-581 improves LV wall hypertrophy, e.g., by increasing volume, i.e., increasing LVEDV.

KCCQ is a 23-item self-administered instrument developed to independently measure the subject's perception of their health status, heart failure impacts their quality of life (QOL) within a 2-week recall period. In the KCCQ, an overall summary score can be derived from the physical function, symptom (frequency and severity), social function, and quality of life domains. Scores are transformed to a range of 0-100, in which higher scores reflect better health status.

In some embodiments, the therapeutically effective amount of a compound of formula (II) or group (II) is at a daily dosage that sufficiently reduces LVOT gradient less than 30 mm/Hg. A reduced dosage regimen or low dose can be 2-5 times fold less than the daily dosage.

In some embodiments, the therapeutically effective amount of a compound of formula (III) or group (III) is at a daily dosage that sufficiently reduces LVOT gradient less than 30 mm/Hg. A reduced dosage regimen can be 2-5 times fold less than the daily dosage.

Some of the symptoms and signs that HCM subjects have include, but are not limited to, shortness of breath (especially during exercise), chest pain (especially during exercise), fainting (especially during or just after exercise), sensation of rapid, fluttering or pounding heartbeats, and heart murmur.

Individuals with HCM can be subdivided based on the presence or absence of left ventricular outflow tract obstruction (LVOT). The presence of LVOT obstruction, i.e. obstructive HCM (oHCM) is associated with more severe symptoms and greater risk of heart failure and cardiovascular death. Limited data support medical treatments (beta blockers, calcium channel blockers, disopyramide) in this subject subset, and persistently symptomatic subjects may be referred for invasive septal reduction therapy.

Individuals without outflow tract obstruction at rest or upon provocation, i.e. non-obstructive HCM (nHCM) account for approximately one-third of HCM subjects under care. Subjects without LVOT obstruction commonly report dyspnea and/or angina and may progress to advanced heart failure. The underlying pathophysiology in nHCM subjects is a hypercontractile, stiff ventricle leading to impaired diastolic function and elevated filling pressures.

Non-obstructive HCM (nHCM) is often clinically characterized by less than a 30 mmHg pressure gradient across the LVOT in an individual at rest, during or immediately after Valsalva maneuver, or post-exercise.

In some embodiments, an individual with nHCM has an LVOT pressure gradient of less than 25 mmHg, or less than 20 mmHg.

In some embodiments, the pressure gradient across the LVOT is measured at rest. In some embodiments, the pressure gradient across the LVOT in the individual is measured during or immediately after a Valsalva maneuver is performed. In some embodiments, the pressure gradient across the LVOT in the individual is measured post-exercise.

As of today, no U.S. Food and Drug Administration (FDA)-approved medical therapies exist for subjects with symptomatic nHCM, and no interventional options are available, short of cardiac transplant. Therefore, there is a need for new therapies for subjects with nHCM.

In some embodiments, the present disclosure provides a method of administering mavacamten or a pharmaceutically acceptable salt thereof to a subject suffering from nHCM.

In some embodiments, the method comprises administering an initial dose of mavacamten or a pharmaceutically acceptable salt thereof. The initial dose may be from about 1 mg to about 10 mg, e.g., about 5 mg.

In some embodiments the initial dose is titrated to a higher dose. For example, the initial dose may be administered for an initial treatment period of at least four weeks, at least six weeks, at least eight weeks, 6-14 weeks, 8-12 weeks, or about 10 weeks, followed by up-titration to a higher dose.

In some embodiments, the initial dose administered to the subject suffering from nHCM is up-titrated to a higher dose based on measuring the NT-proBNP or BNP level, or change in NT-proBNP or BNP level in the subject.

In some embodiments, the initial dose is up-titrated to a higher dose if NT-proBNP has not decreased by at least 20-60% (e.g., at least 30-50%, or at least 40%) during treatment with the first dose during the initial treatment period.

In some embodiments, the initial dose is up-titrated to a higher dose if NT-proBNP has not decreased by at least 20-60% (e.g., at least 30-50%, or at least 40%) during treatment with the first dose during the initial treatment period, and NT-proBNP is greater than 125-400 pg/mL, e.g., greater than 300 pg/mL. In some embodiments, the NT-proBNP or BNP level is measured after 6-10 weeks (e.g., about 8 weeks) of administration of the initial dose.

In some embodiments, if NT-proBNP has decreased by 40% or more, then treatment is continued at the initial dose, with no up-titration. In some embodiments the higher dose is from about 2.5 mg to about 20 mg (e.g., about 5 mg to about 15 mg, or about 10 mg).

In some embodiments, the higher dose or the continued initial dose is administered to the subject suffering from nHCM during a second treatment period. In some embodiments, the dose of the second treatment period is up-titrated to a higher dose based on measuring the NT-proBNP or BNP level, or change in NT-proBNP or BNP level in the subject. In some embodiments, the dose of the second treatment period is up-titrated to a higher dose if NT-proBNP has not decreased by at least 20-60% (e.g., at least 30-50%, or at least 40%) during treatment during the initial and second treatment periods, and NT-proBNP is greater than 125-400 pg/mL, e.g., greater than 300 pg/mL.

In some embodiments, the dose of the second treatment period is up-titrated to a higher dose if NT-proBNP is greater than 400-600 pg/mL (e.g., greater than 500 pg/mL) after treatment during the initial and second treatment periods, and NYHA is class 3.

In some embodiments, the method of administering mavacamten or a pharmaceutically acceptable salt thereof to a subject suffering from nHCM may comprise down-titration of the initial dose if LVEF decreases during treatment, for examples if LVEF is less than 80-90% (e.g. less than 85%) of baseline or LVEF is less than 55%. In some embodiments, the method may comprise down-titration of the initial dose if NT-proBNP or BNP increases during treatment, for example if the increase is greater than 20-40% (e.g., greater than 30%).

Diastolic dysfunction is present or an important feature of a series of diseases including, but not limited to, hypertrophic cardiomyopathy (HCM), heart failure with preserved ejection fraction (HFpEF), left ventricular hypertrophy (LVH)—including both disorders of active relaxation and disorders of chamber stiffness (diabetic HFpEF). Diastolic dysfunction may be diagnosed using one or more techniques and measurements, including: invasive procedures, such as catheter procedures, E/e', left atrial size, and BNP or NT-proBNP.

Ejection fraction is an indicator of normal or hypercontractile systolic function, i.e., ejection fraction is greater than about 52% or 50% in subjects with normal or hypercontractile systolic function.

LVH, which is characterized by wall thickness, may be diagnosed using one or more techniques and measurements, including: echocardiogram, cardiac MRI, noninvasive imaging techniques (e.g., tissue Doppler imaging) and E/e'.

Subjects in need of treatment for diastolic dysfunction include subjects from a patient population characterized by nHCM, LVH, or HFpEF. Subjects in need of treatment for diastolic dysfunction include subjects who exhibit left ventricle stiffness as measured by echocardiography or left ventricle stiffness as measured by cardiac magnetic resonance.

In some embodiments, the subject in need thereof is from a HFpEF patient population. In some embodiments, the subject from a HFpEF patient population is diagnosed with HCM. In some embodiments, the subject from a HFpEF patient population is not diagnosed with HCM.

In some embodiments, the subject having HFpEF has an ejection fraction of ≥50% and has evidence of abnormal diastolic function. Abnormal diastolic function includes impaired left ventricle relaxation, filling, diastolic distensibility, or stiffness. These traits can be measured using echocardiography. In some embodiments, subjects are considered to have abnormal diastolic function when at least one of the following echocardiography values are met septal e'<7 cm/sec; lateral e'<10 cm/sec, average E/e' ratio>14; LA volume index>34 $mL/m^2$; peak TR velocity>2.8 m/sec. In some embodiments, subjects are considered to have abnormal diastolic function when at least three of the above listed values are met.

In some embodiments, the subject in need thereof is from an HCM patient population. In some embodiments, the subject from an HCM patient population is diagnosed with HFpEF. In some embodiments, the subject from an HCM patient population is not diagnosed with HFpEF.

In some embodiments, the subject in need thereof exhibits left ventricle stiffness as measured by echocardiography. A subject is considered to have left ventricle stiffness as measured by echocardiography when at least one of the following characteristics are met: mitral E/A ratio>0.8; septal e'<7 cm/sec; lateral e'<10 cm/sec, average E/e'≥14; LA volume index>34 mL/m2; peak TR velocity>2.8 m/sec. In some embodiments, subjects are considered to have left ventricle stiffness when at least three of the above listed values are met.

Further determining factors for diagnosing diastolic dysfunction using echocardiography are described in *J Am Soc Echocardiogr.* 29(4):277-314 (2016), the contents of which are incorporated herein for all purposes.

In some embodiments, the subject in need thereof exhibits left ventricle stiffness as measured by cardiac magnetic resonance. Cardiac magnetic resonance is used to determine peak filling rate, time to peak filling, and peak diastolic strain rate. Accordingly, in some embodiments, a subject has left ventricle stiffness as measured by cardiac magnetic resonance when at least one of the following characteristics are met: abnormal peak filing rate, time to peak filling, or peak diastolic strain rate.

In some embodiments, the subject in need thereof are suffering from diastolic dysfunction, left ventricular hypertrophy, left ventricular outflow tract obstruction, increased left ventricular wall thickness (or mass index), increased interventricular septal (IVS) wall thickness, poor or reduced cardiac elasticity, poor or reduced diastolic left ventricular relaxation, abnormal high left atrial pressure, reduced E/e' ratio, diminished exercise capacity or tolerance, diminished peak oxygen consumption ($VO_2$), increased left ventricular diastolic pressure, or any combination thereof.

In some embodiments, the subject in need thereof are suffering from hypertrophic cardiomyopathy (HCM) characterized by at least one biomarker selected from elevated level of NT-proB-Type Natriuretic Peptide (NT-proBNP), elevated level of cardiac troponin I. In another embodiment, the HCM subject in need thereof has a predisposition to developing HCM.

In some embodiments, the subject in need thereof are suffering from chest pain, dyspnea, angina, syncope or dizziness.

In some embodiments, the total daily dose is adjusted according to individual subject requirements. For example, the total daily dose may be adjusted after 4-16 weeks (e.g. after 4, 5, 6, 7, 8, 8, 10, 11, 12, 13, 14, 15, 16 weeks, or any number of days in between) of initiating therapy with a compound of formulas (I), (II), (III), and/or a compound of groups (I), (II), (III), and/or mavacamten, and/or MYK-581 depending on the response profile of the subject. In some embodiments, the total daily dose is decreased when the subject's New York Heart Association (NYHA) functional classification is reduced.

In some embodiments, the total daily dose of mavacamten is increased when the subject's New York Heart Association (NYHA) functional classification is not reduced or worsens.

In some embodiments, the individual subjects requirements used to adjust the total daily dose are the subject's resting left ventricular ejection fraction and resting left ventricular outflow tract (LVOT) peak gradient. As a non-limiting example, in some embodiments, the total daily dose of mavacamten is 5 mg, and said dose is increased when the subject's resting left ventricular ejection fraction (LVEF) is ≥55% and resting left ventricular outflow tract (LVOT) peak gradient is ≥30 mm Hg.

In some embodiments, the total daily dose of mavacamten is increased to 7.5 mg when the subject's resting left ventricular ejection fraction (LVEF) is ≥55% and resting left ventricular outflow tract (LVOT) peak gradient is from >30 mm Hg to <50 mm Hg.

In some embodiments, the total daily dose of mavacamten is increased to 10 mg when the subject's resting left ventricular ejection fraction (LVEF) is ≥55% and resting left ventricular outflow tract (LVOT) peak gradient is ≥50 mm Hg.

In some embodiments, the therapeutically effective amount of a compound of formulas (I), (II), (III), and/or a compound of groups (I), (II), (III), and/or mavacamten, and/or MYK-581 can be adjusted according to the left ventricular ejection fraction (LVEF) level of the subject.

In some embodiments, the method provided herein also includes measuring the left ventricular ejection fraction (LVEF) in the subject prior to the administration of a compound of formulas (I), (II), (III), and/or a compound of groups (I), (II), (III), and/or mavacamten, and/or MYK-581, thereby providing a first LVEF value (baseline).

In some embodiments, the method provided herein also includes measuring the LVEF in the subject sometimes (e.g., 1, 2, 3, 4, 5, 6, 7, 8, 9, 10, 11, 12, 13, 14, 15, 16, 17, 18, 19, 20, 21, 22, 23, 24, 25, 26, 27, or 28 days) after the imitation of a compound of formulas (I), (II), (III), and/or a compound of groups (I), (II), (III), and/or mavacamten, and/or MYK-581, thereby providing a second LVEF value, and calculating a percentage of change of the second LVEF value compared to the first LVEF value. Accordingly, in some embodiments, total daily dosage is adjusted according to the percentage of change of LVEF. Optimally, the LVEF is maintained in the normal range.

In some embodiments, the second LVEF is measured 4 weeks after the administration of a compound of formulas (I), (II), (III), and/or a compound of groups (I), (II), (III), and/or mavacamten, and/or MYK-581.

In some embodiments, the therapeutically effective amount of a compound of formula (I), (II), or (III), and/or a compound of group (I), (II), or (III), and/or mavacamten, and/or MYK-581 can be adjusted according to the cardiac troponin I level of the subject. The cardiac troponin I level can be measured by any of the methods known to one skilled in the art or following the procedure descriptions in a clinically validated assay, such as Abbott's ARCHITECT Stat Troponin-I 2K41 assay or in Siemens' Advia Centur® High Sensitivity Troponin I (TNIH) assay. The cardiac troponin T level can be measured by any of the methods known to one skilled in the art or following the procedures description in Roche's Elecsys Troponin T hs Assay. BNP levels can be measured by any one of the methods known to one skilled in the art or following the procedures description of the ADVIA Centaur XPT/XP/CP Immunoassay System.

In some embodiments, the therapeutically effective amount of a compound of formula (I), (II), or (III), and/or a compound of group (I), (II), or (III), and/or mavacamten, and/or MYK-581 can be adjusted according to NT-proBNP or BNP level of the subject. The NT-ProBNP level of the subject can be measured by any of the methods known to one skilled in the art or following the procedures description in Roche's Elecsys proBNPII Immunoassay.

In some embodiments, a compound of formula (I), (II), or (III), and/or a compound of group (I), (II), or (III), and/or mavacamten, and/or MYK-581 are administered in a subject suffering from hypertrophic cardiomyopathy (HCM) characterized by at least one biomarker or combination thereof selected from an elevated level of B-type natriuretic peptide (BNP), an elevated level of NT-proB-Type Natriuretic Peptide (NT-proBNP), and an elevated level of cardiac troponin I. In yet another embodiment, the subject additionally has a predisposition to develop HCM.

In some embodiments, the therapeutically effective amount can be adjusted according to the plasma concentration of a compound of formulas (I), (II), (III), and/or a compound of groups (I), (II), (III), and/or mavacamten, and/or MYK-581.

In some embodiments, the method also includes measuring the plasma concentration of a compound of formulas (I), (II), (III), and/or a compound of groups (I), (II), (III), and/or mavacamten, and/or MYK-581 at least 1, 2, 3, 4, 5, 6, 7, 8, 9, 10, 11, 12, 13, 14, 15, 16, 17, 18, 19, 20, 21, 22, 23, 24, 25, 26, 27, or 28 days after administration of the compound.

In some embodiments, the therapeutically effective amount can be adjusted based on 'trough' measurements. 'Trough' measurements (either concentration or any pharmacodynamic measurement) refers to measurements taken just prior to the next dose. For example, for once daily (QD) dosing these occur every ~24 hours just prior to the subject taking their next dosage (typically a tablet or capsule). For pharmacokinetic reasons, these measurements are used as a way to standardize assessments and minimize variability. When an individual "achieves and maintains" a certain blood plasma concentration of the compound, the individual's trough measurement does not go below the referenced minimum level or above the referenced maximum level.

Pharmaceutical Composition

The pharmaceutical compositions for the administration of a compound of formulas (I), (II), (III), and/or a compound of groups (I), (II), (III), and/or mavacamten, and/or MYK-581 or a pharmaceutically acceptable salt thereof may conveniently be presented in unit dosage form and may be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active agent is generally included in an amount sufficient to produce the desired effect upon myocardial contractility (i.e. to decrease the often supranormal systolic contractility in HCM) and to improve left ventricular relaxation in diastole. Such improved relaxation can alleviate symptoms in hypertrophic cardiomyopathy and other etiologies of diastolic dysfunction. It can also ameliorate the effects of diastolic dysfunction causing impairment of coronary blood flow, improving the latter as an adjunctive agent in angina pectoris and ischemic heart disease. It can also confer benefits on adverse left ventricular remodeling in HCM and other causes of left ventricular hypertrophy due to chronic volume or pressure overload from, e.g., valvular heart disease or systemic hypertension.

The pharmaceutical compositions containing a compound of formulas (I), (II), (III), and/or a compound of groups (I), (II), (III), and/or mavacamten, and/or MYK-581 or a pharmaceutically acceptable salt thereof, may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

In some embodiments, a compound of formulas (I), (II), (III), and/or a compound of groups (I), (II), (III), and/or mavacamten, and/or MYK-581 can be used in the form of pharmaceutically acceptable salt. Examples of the pharmaceutically acceptable salt include salts with inorganic bases, salts with organic bases, salts with inorganic acids, salts with organic acids, and salts with basic or acidic amino acids.

Pharmaceutical Dosage Forms

The present disclosure includes novel pharmaceutical dosage forms of mavacamten or a pharmaceutically acceptable salt thereof. The dosage forms described herein are suitable for oral administration to a subject. The dosage form may be in any form suitable for oral administration, including, but not limited to, a capsule or a tablet. In some embodiments, the present disclosure provides a single unit dosage capsule or tablet form containing 1-25 mg (e.g., 1, 1.5, 2, 2.5, 3, 3.5, 4, 4.5, 5, 6, 7, 7.5, 8, 9, 10, 11, 12, 12.5, 13, 14, 15, 16, 17, 18, 19, 20, 21, 22, 23, 24, or 25 mg) of mavacamten or a pharmaceutically acceptable salt thereof. In some embodiments, the amount of mavacamten in a unit dosage is from about 2 to 5 mg, from about 5 to 10 mg, about 2.5 mg or about 5 mg. In some embodiments, the single unit dosage form of is a capsule. In some embodiments, the single unit dosage form of is a tablet.

Combination Therapy

The present disclosure provides both a myosin inhibitor monotherapy and combination therapy. In combination therapy, a myosin inhibitor regimen of the present disclosure is used in combination with an additional therapy regimen, e.g., a standard of care (SOC) therapy for the patient's cardiac condition or other therapy useful for treating the relevant disease or disorder. The additional therapeutic agent may be administered by a route and in an amount commonly used for said agent or at a reduced amount, and may be administered simultaneously, sequentially, or concurrently with a myosin inhibitor.

In certain embodiments, a myosin inhibitor is administered with another therapeutic agent such as a beta-blocker, an angiotensin converting enzyme (ACE) inhibitor, an angiotensin receptor antagonist (e.g., an angiotensin II receptor blocker), an angiotensin receptor neprilysin inhibitor (ARNI) (e.g., sacubitril/valsartan), a mineralocorticoid receptor antagonist (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium or magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), warfarin, a RAAS inhibitor, an arrhythmia medication, an anticoagulant, an antithrombotic agent, an antiplatelet agent, or any combination thereof.

Suitable ARBs may include, e.g., A-81988, A-81282, BIBR-363, BIBS39, BIBS-222, BMS-180560, BMS-184698, candesartan, candesartan cilexetil, CGP-38560A, CGP-48369, CGP-49870, CGP-63170, CI-996, CV-11194, DA-2079, DE-3489, DMP-811, DuP-167, DuP-532, E-4177, elisartan, EMD-66397, EMD-73495, eprosartan, EXP-063, EXP-929, EXP-3174, EXP-6155, EXP-6803, EXP-7711, EXP-9270, FK-739, GA-0056, HN-65021, HR-720, ICI-D6888, ICI-D7155, ICI-D8731, irbesartan, isoteoline, KRI-1177, KT3-671, KW-3433, losartan, LR-B/057, L-158809, L-158978, L-159282, L-159874, L-161177, L-162154, L-163017, L-159689, L-162234, L-162441, L-163007, LR-B/081, LR B087, LY-285434, LY-302289, LY-315995, LY-235656, LY-301875, ME-3221, olmesartan, PD-150304, PD-123177, PD-123319, RG-13647, RWJ-38970, RWJ-46458, saralasin acetate, S-8307, S-8308, SC-52458, saprisartan, saralasin, sarmesin, SL-91.0102, tasosartan, telnisartian, UP-269-6, U-96849, U-97018, UP-275-22, WAY-126227, WK-1492.2K, YM-31472, WK-1360, X-6803, valsartan, XH-148, XR-510, YM-358, ZD-6888, ZD-7155, ZD-8731, and zolasartan.

In particular embodiments, the additional therapeutic agent may be an ARNI such as sacubitril/valsartan (Entresto®) or a sodium-glucose cotransporter 2 inhibitor (SGLT2i) such as empaglifozin (e.g., Jardiance®), dapagliflozin (e.g. Farxiga®), or sotagliflozin.

In yet another embodiment, a patient being treated for heart failure with a nyosin inhibitor is also being treated with an ARNI, a beta blocker, and/or an MRA.

In one embodiment, the anti-arrhythmia medication is disopyramide.

If any adverse effect occurs, the patient may be treated for the adverse effect. For example, a patient experiencing a headache due to the myosin inhibitor treatment may be treated with an analgesic such as ibuprofen and acetaminophen.

EXAMPLES

Abbreviations

AE adverse event
AESI adverse event of special interest
ALP alkaline phosphatase
ALT alanine aminotransferase
ASA alcohol septal ablation
AST aspartate aminotransferase
BP blood pressure
CPET cardiopulmonary exercise testing
CV cardiovascular
DILI drug-induced liver injury
EC ethics committee; refers to an IRB or IEC or equivalent
ECG electrocardiogram
eCRF electronic case report form
EDC electronic data capture
EOS end of study
ET early termination
FDA Food and Drug Administration
FSH follicle-stimulating hormone
GCP Good Clinical Practice
HCM hypertrophic cardiomyopathy
HR heart rate
IUD intrauterine device
IUS intrauterine system
IXRS interactive response system
KCCQ Kansas City Cardiomyopathy Questionnaire
LV left ventricular
LVEF left ventricular ejection fraction
LVOT left ventricular outflow tract
MAD multiple ascending dose
MedDRA Medical Dictionary for Regulatory Activities NT-proBNP N-terminal pro b-type natriuretic peptide
NYHA New York Heart Association
oHCM obstructive hypertrophic cardiomyopathy
PD pharmacodynamic(s)
PK pharmacokinetic(s)
PM poor metabolizer
QD once daily
QoL quality of life
QTc corrected QT interval
QTcF Fridericia-corrected QT interval
SAD single ascending dose
SAE serious adverse event
SD standard deviation
SOC system organ class
SRT septal reduction therapy
SUSAR suspected unexpected serious adverse reactions
Stress echo Stress echocardiography
TBL total bilirubin
TEAE treatment-emergent adverse event
TTE transthoracic echocardiography, transthoracic echocardiogram
ULN upper limit of normal

Example 1. Week-48 Observations from the PIONEER-OLE Study of Mavacamten

In a Phase 2 (PIONEER-HCM) clinical trial of subjects with obstructive HCM, mavacamten reduced or eliminated the obstruction of the left ventricular outflow tract, resulting in improvements in how subjects feel (as measured by New York Heart Association classification and the Kansas City Cardiomyopathy Questionnaire), and how their hearts are functioning (based on peak $VO_2$ measured by cardiopulmonary exercise testing). Heitner, S B, et al., (April 2019 online) *Ann. Intern. Med.* 170(11):741-748

The following describes (1) the trial design of the PIONEER OLE study, which is a Phase 2, open-label, multicenter study of adults with symptomatic oHCM who have previously completed the PIONEER-HCM Study and (2) observations at Week 48 with respect to subjects treated with mavacamten in the PIONEER-OLE, which trial is currently ongoing.

PIONEER-OLE Study Objectives:

(a) Primary Objective: To assess the long-term safety and tolerability of mavacamten in individuals with symptomatic obstructive hypertrophic cardiomyopathy (oHCM).

(b) Secondary Objectives: To assess in individuals with symptomatic oHCM the long-term effects of mavacamten on left ventricular outflow tract (LVOT) obstruction, on functional capacity, and on oHCM symptoms.

(c) Pharmacokinetic Objective: To perform population pharmacokinetics (PK) analyses in individuals with symptomatic oHCM receiving mavacamten.

Figure 19:
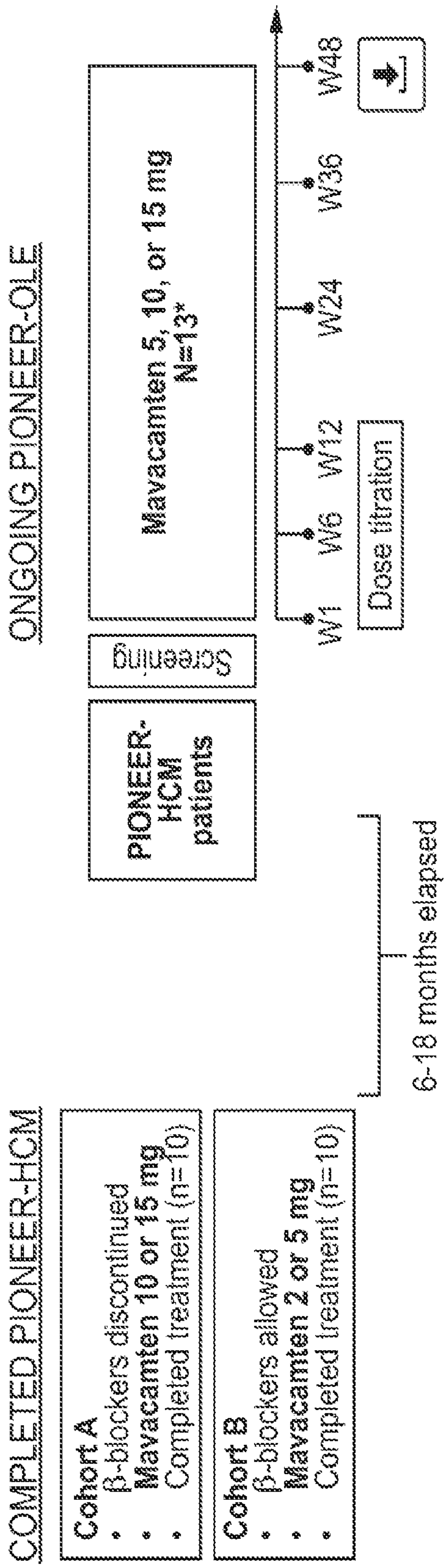
FIG. 19 is a scheme for the study of Example 1 showing the transition to the open label extension study.
Figure 20:
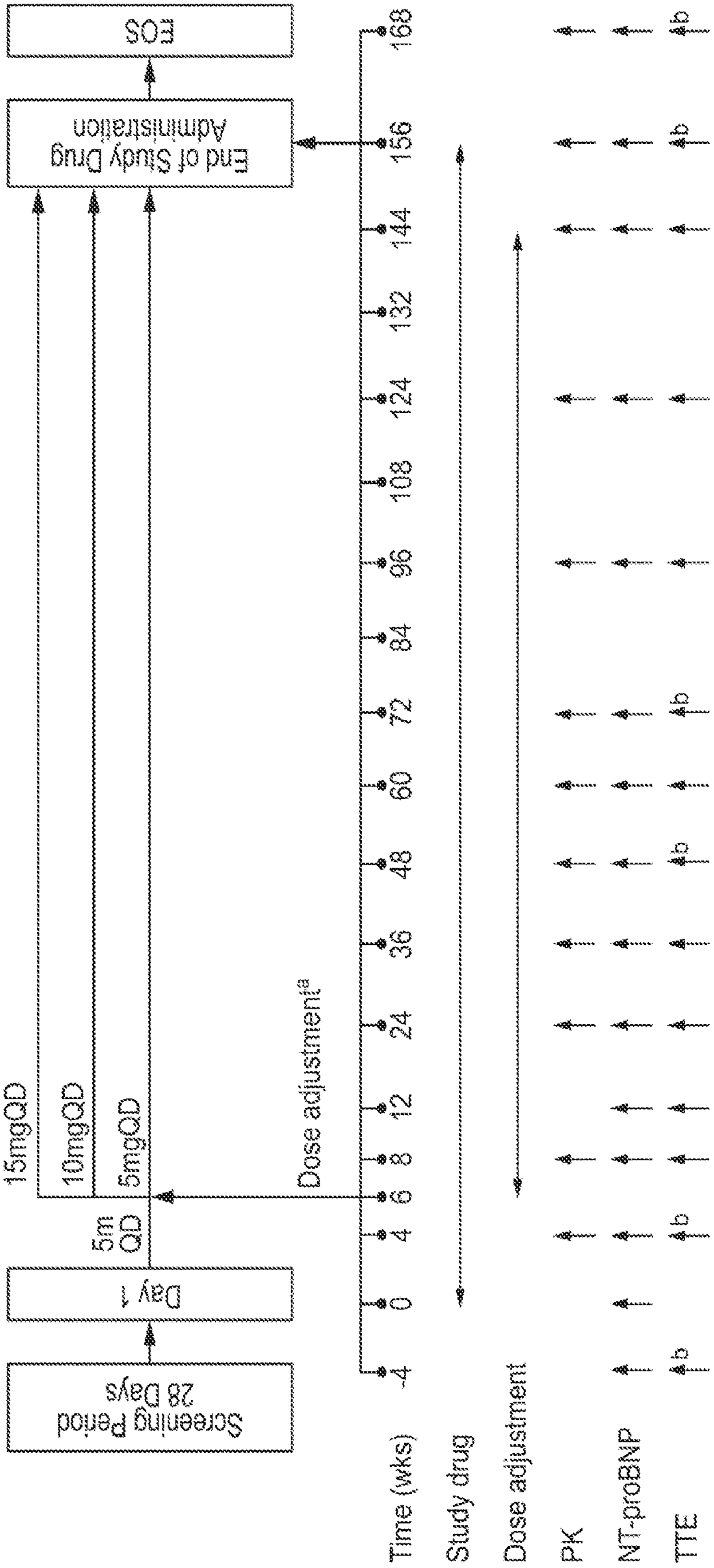
FIG. 20 is a scheme for the study of Example 1 showing the dosing protocol for the study.

Study Design and Plan:

The study was designed as shown in FIGS. 19 and 20. All subjects were started on a dose of 5 mg QD.

To maximize safety, the starting dose will be 5 mg for all subjects. Subjects will return at Week 4 (±4 days) for a plasma PK sample to measure drug levels and to undergo echocardiography to determine LVOT gradient (at rest, after a Valsalva maneuver, and after exercise) and left ventricular ejection fraction (LVEF). Subjects will return at Week 6 (±7 days) for evaluation of Week 4 results and dose adjustment to obtain a steady-state trough plasma concentration of approximately 250 ng/mL to 500 ng/mL, based on PK modeling (i.e., 5, 10 or 15 mg mavacamten QD).

These plasma concentration levels have generally been associated with a marked reduction in LVOT gradient and they have been well-tolerated without excessive reductions in left ventricular ejection fraction (LVEF).

For eligible subjects, an increase in dose beyond the target at a later time point after Week 6 may also be possible. Decreased doses after Week 6 may also be possible if indicated by LVEF, PK or clinical judgment of the investigator in discussion with the medical monitor. Subjects are allowed to stay on background therapy with either beta blockers or calcium channel blockers.

A stress echocardiogram will be administered at Week 48 and Week 72 to evaluate the post-exercise LVOT gradient and to determine whether further dose adjustment may be needed.

If the post-exercise LVOT gradient is measured ≥50 mm Hg, further dose adjustment may be considered.

The dose will not be increased if one or more of the following criteria are met:

(a) LVEF is <55%, and/or (b) LVOT gradient is <30 mmHg after exercise, and/or (c) Trough Mavacamten plasma concentration is >350 ng/mL, and/or (d) A dose increase is not warranted in the clinical judgment of the Investigator.

Dose Reduction Rule: The dose may be reduced or discontinued in the case of an exaggerated pharmacologic effect at any time during the study based on the clinical judgment of the Investigator.

Temporary Discontinuation: If results as reported by the central laboratories from any visit show Mavacamten plasma concentration is ≥1000 ng/mL, or LVEF<45% (central read), or Fridericia-corrected QT interval (QTcF) meets the following criteria, the subject will be notified by the study site/Investigator for further instructions:

(a) If QRS is narrow (<120 ms), then temporary discontinuation criteria are the smaller of: 15% increase from baseline QTcF OR QTcF≥520 ms, (b) If QRS is wide (120 ms), then temporary discontinuation criteria are the smaller of: a 15% increase from baseline QTcF OR QTcF≥550 ms, (c) If the subject is taking 5 mg, 10 mg, or 15 mg, study drug will be temporarily discontinued and he or she will return for an unscheduled visit (with electrocardiogram [ECG] and TTE assessments) 2 to 4 weeks later.

If LVEF≥55% and QTcF<500 ms at the unscheduled visit, then the study drug will be restarted at a lower dose as shown below (previous dose→restart dose):

(a) 5 mg→resume 5 mg, (b) 10 mg→5 mg, (c) 15 mg→10 mg.

Subjects on 5 mg who have been temporarily discontinued on treatment based on clinical evaluation can be considered for dose reintroduction at 5 mg.

If LVEF, plasma drug concentration and/or QTcF persist out of range at the follow-up visit, then the subject will be discontinued from the study.

After Week 6, additional study visits will occur at Week 8 (±7 days), Week 12 (±7 days), and every 12 weeks (±7 days) thereafter. Subjects also will be contacted by phone in between clinic visits, at Week 18 and every 12 weeks thereafter. An end of study (EOS) visit will occur 12 weeks (±7 days) after the last administration of study drug. Visits (including the Screening visit which serves as the baseline)

will entail recording vital signs, targeted physical examination, ECGs, safety laboratory tests, N-terminal pro b-type natriuretic peptide (NT-proBNP), adverse events (AEs), New York Heart Association (NYHA) functional class, Kansas City Cardiomyopathy Questionnaire (KCCQ) score, and concomitant medications. At Weeks 4, 8, 24, 36, 48, 60, 72, 96, 120, 144, 156/early termination (ET), and 168/EOS, a predose blood sample for assessment of drug concentration will be obtained. A standard TTE (including but not limited to assessment of LVOT gradient at rest and after Valsalva) will be performed at baseline, at Weeks 4, 8, 12, 24, 36, 48, 72, 96, 120, 144, 156/ET, and 168/EOS. In addition, a stress echocardiogram (with assessment of LVOT gradient post-exercise) will also be performed at baseline, Weeks 4, 48, 72, 156/ET, and 168/EOS.

Subjects will be followed through completion of EOS procedures. All AEs, including serious adverse events (SAEs), will be collected from the time of informed consent through the duration of the study, up to and including the Week 168/EOS visit. If there is a significant clinical abnormality or clinically significant laboratory abnormality in need of monitoring, the subject will be followed until resolution of the abnormality or until it is considered stable in the opinion of the Investigator.

Subject may receive dose reduction after they are on a stable dose of 10 mg or 15 mg treatment for 24 weeks or longer. Subjects that have been dose reduced will undergo a follow-up visit 4 to 8 weeks (±7 days) later (to mirror Week 8 assessments including a TTE assessment). Based on results and clinical symptoms at follow-up visits, subsequent dose decisions will be determined. This cycle of potential dose reduction and follow up can be repeated more than once (after at least 24 weeks on a stable dose of 10 or 15 mg treatment).

Study Duration:

The study duration is 172 weeks (up to 4 weeks for screening, 156 weeks for treatment, and a 12-weeks post treatment follow-up). The study protocol may be amended to allow an extension beyond 3 years.

Study Endpoints:

The study endpoints include safety, tolerability, and select measures of efficacy using individualized dosing. Key measurements include LVOT gradient, LVEF, NT-proBNP.

Safety Endpoints Include:

1. Frequency and severity of treatment-emergent AEs and SAEs,
2. Frequency of cardiovascular (CV) death,
3. Frequency of sudden death,
4. Frequency of CV hospitalization,
5. Frequency of heart failure requiring the initiation of oral loop diuretics or the administration of intravenous loop diuretics,
6. Frequency of myocardial infarction,
7. Frequency of ventricular arrhythmias (ventricular tachycardia, ventricular fibrillation, ventricular flutter, torsade de pointe),
8. Frequency of syncope,
9. Frequency of seizures,
10. Frequency of stroke,
11. Frequency of LVEF≤45 as measured by echocardiography,
12. QT and QTcF intervals over time.

Efficacy and Pharmacodynamics Include:

1. Post-exercise, post-Valsalva, and resting LVOT gradient over time,
2. NYHA functional class over time,
3. KCCQ scores over time,
4. NT-proBNP over time,
5. Frequency of septal reduction therapy.

Pharmacokinetics Endpoints Include:

Mavacamten plasma concentration over time and Population PK.

Baseline Characteristics of Subjects

| Characteristic | PIONEER-HCM n = 13 | PIONEER-OLE N = 13 |
|---|---|---|
| Age, year, mean (SD) | 56.5 (13.2) | 57.8 (133) |
| Male, n (%) | 9 (69.2) | |
| NYHA functional class, n (%) | | |
| Class II | 9 (69.2) | 12 (92.3) |
| Class III | 4 (30.8) | 1 (7.7) |
| Background HCM therapy while on study drug, n | | |
| Metoprolol | 7 (53.8) | 11 (84.6) |
| Bisoprolol | 0 | 1 (7.7) |
| Echocardiography parameters | | |
| Resting LVEF, %, mean (SD) | 73.0 (5.6) | 72.0 (4.9) |
| LVOT gradient, mm Hg, mean (SD) | | |
| Resting | 69.7 (53.9) | 67.3 (42.8) |
| Valsalva | 93.7 (55.6) | 89.9 (30.7) |
| Post-exercise | 94.5 (45.0) | 127.5 (33.4) |
| NT-pro BNP, pg/mL, mean (SD) | 1601 (2702) | 1836 (2886) |

PIONEER-OLE Study Results:

Result 1. PIONEER-OLE Week-48 Results: Safety and Efficacy Maintained Through One Year in Open-Label Extension Study of 12 Subjects with Symptomatic, Obstructive HCM.

Data for twelve subjects at 48 weeks of treatment with mavacamten were consistent with prior safety and efficacy observations at the 12-, 24-, and 36-week readouts. Highlights of the data include continued safety and tolerability and sustained clinical benefits, including reductions in left ventricular outflow tract gradient (LVOT), improvements in NYHA functional class and improvement of multiple biomarkers toward normal ranges. For the first time, a reduction in septal wall thickness, a defining characteristic of HCM, was observed, as well as improvements in subjects' quality of life, as measured by the Kansas City Cardiomyopathy Questionnaire (KCCQ), were also reported.

Data for twelve subjects at 48 weeks in this trial demonstrates continued safety, reduced LVOT gradient profile and normal LVEF. Mavacamten was well tolerated throughout the one-year treatment period. There were no cardiac-related adverse events (AEs) attributed to study drug throughout the 48-week period. To date, all adverse events attributed to treatment have been mild or moderate and transient.

The longest duration of mavacamten therapy was 1.5 years. There were no dose changes due to AEs. There were 4 SAEs in 3 subjects; not cardiovascular and not related to study drug. There was one cardiovascular AE (NSVT) not related to study drug. Of 64 AEs, most were mild or moderate, and transient. 8 AEs in 3 subjects were considered potentially related to study drug (fatigue, dyspnea, dizziness, lethargy); 7 were mild and 1 was moderate; one subject had 3 severe AEs and 1 serious AE that were unrelated—male with history of ulcerative colitis presented 4 days after Week 24 visit with epigastric pain, elevated AST (>5×ULN), and biliary obstruction; subsequently diagnosed with Klatskin type cholangiocarcinoma; the subject discontinued study drug dosing and had an early study termination.

Figure 1B:
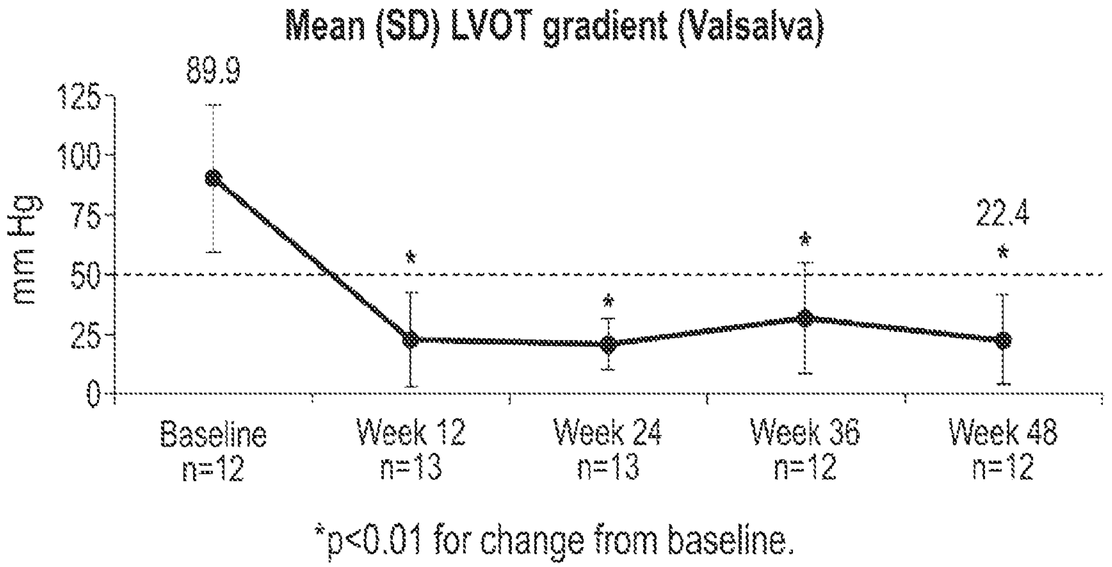
FIG. 1B is a plot of Mean LVOT gradient (Valsalva) for the subjects in Example 1.
Figure 1C:
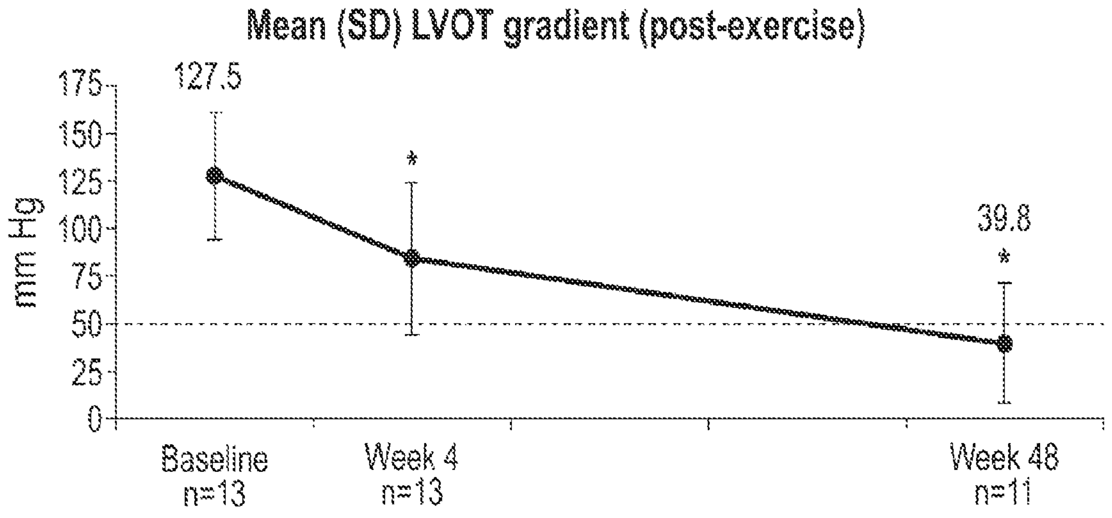
FIG. 1C is a plot of Mean LVOT gradient (post-exercise) for the subjects in Example 1.
Figure 1D:
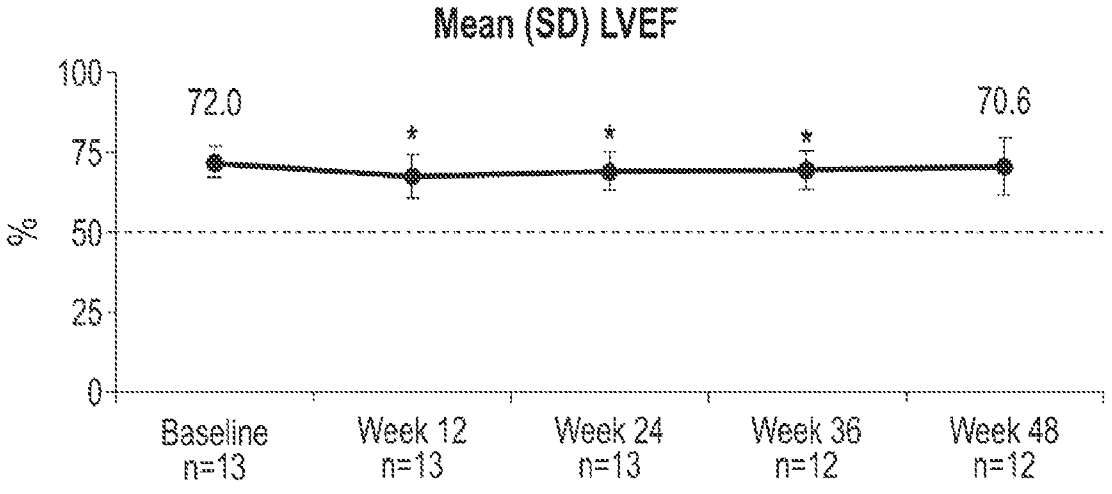
FIG. 1D is a plot of Mean LVEF for the subjects in Example 1.

LVOT gradient, a measure of obstruction of the left ventricle, was consistently reduced from baseline with statistical significance p<0.01 in all subjects with evaluable visits at all timepoints under multiple conditions of testing: i.e. at rest, post-exercise and upon provocation with a Valsalva maneuver. At week 48, resting LVOT gradient for all subjects was below 50 mmHg, the guideline-based threshold for an invasive intervention, and 11 of 12 subjects were below the 30 mmHg threshold at which obstructive HCM is diagnosed. Provoked gradient measurements, taken using a Valsalva maneuver and post-exercise, were also below 50 mmHg in all but two subjects at Week 48. In FIGS. 1A-1C, the mean resting LVOT gradient was 67.3 mm Hg (standard deviation [SD], 42.8) at baseline and 14.0 mm Hg (SD, 9.7) at Week 48 (mean change of −52.7 mm Hg, P=0.0005). Similar improvements were seen in Valsalva LVOT gradient (mean change of −66.0 mm Hg, P=0.001) and post-exercise LVOT gradient (mean change of −85.1 mm Hg, P=0.001) at Week 48. Five patients achieved a post-exercise LVOT gradient<30 mm Hg. The mean change from baseline in LVEF was −1.8% (P=0.3013) at Week 48 (1D). LVEF was maintained above 50% for all patients at all timepoints throughout the study. One subject could not complete a stress echocardiogram at Week 48 due to residual effects from serious adverse event. Left ventricular ejection fraction (LVEF) remained above normal (50%) for all 12 subjects at all times of assessment. See FIG. 1D.

Result 2. Improvements in Both Symptom Burden and Quality of Life has been Observed Among the PIONEER-OLE Subjects at Week 48.

Figure 2A:
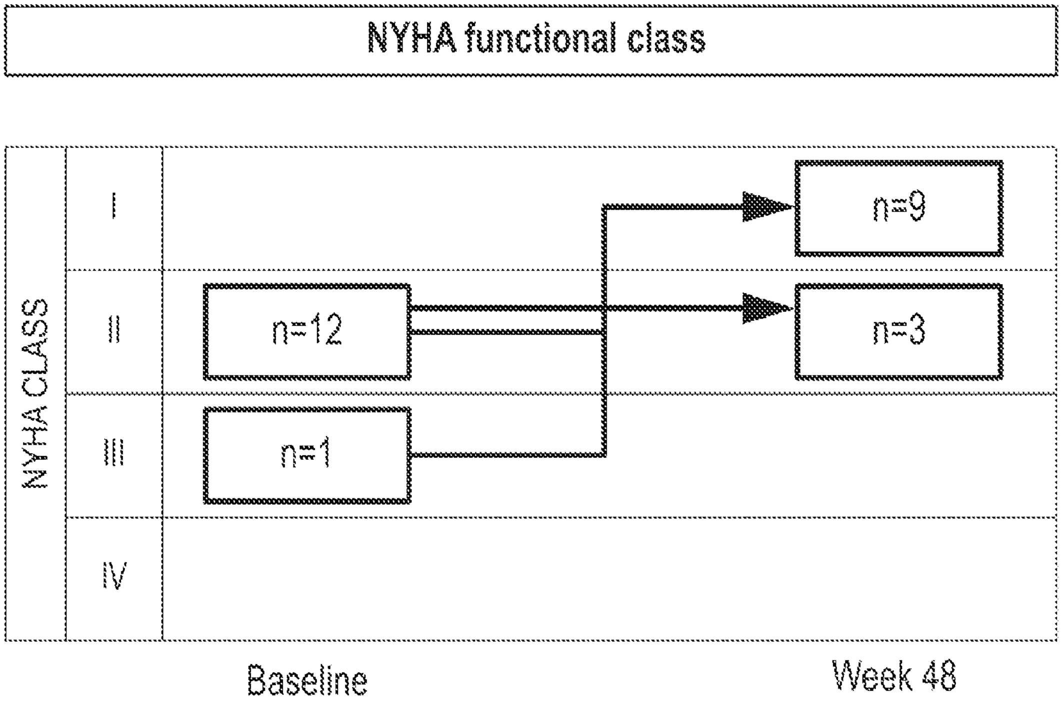
FIG. 2A is a chart showing the change in NYHA functional class after 48 weeks in the study of Example 1.

At baseline, subjects enrolled in PIONEER-OLE were symptomatic with a NYHA classification of Class II or III. NYHA classifications were measured at Week 24 and Week 48 and demonstrated improvements, with nine out of twelve subjects achieving asymptomatic status (Class I). See FIG. 2A.

Figure 2B:
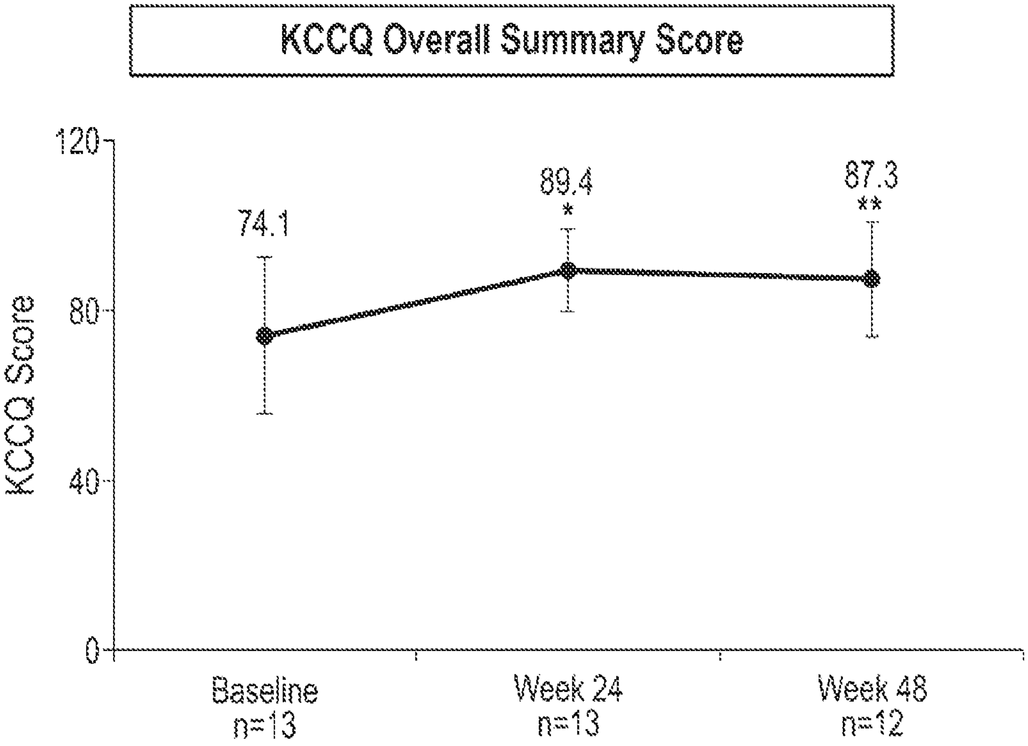
FIG. 2B is a plot of the change in KCCQ overall summary score after 48 weeks in the study of Example 1.

Positive results from the Kansas City Cardiomyopathy Questionnaire (KCCQ), designed to measure subjects' perception of their heart failure health status and its impact on the activities of daily living, were also reported. In PIONEER-OLE, KCCQ mean scores went from 74.1 at baseline to 87.3 at Week 48 (Scores range from 0-100, and higher scores reflect better status). A clinically significant change in KCCQ is defined as greater than or equal to 6. See FIG. 2B. In FIG. 2B, scores range from 0 to 100. Higher score reflects better health status.

Result 3. Evidence Suggests Favorable Impact on Cardiac Structure, Including Reductions in Interior Septal Wall Thickness, and Left Ventricle Filling As shown below, mavacamten improved markers related to ventricular filling at Weeks 12, 24, 36, and 48. During this period, there was a significant increase in mitral annular velocity during early diastole ($e'_{lat}$) and concomitant reduction in $E/e'_{lat}$; there was a significant decrease in left atrial (LA) volume, and the levels of NT-proBNP were significantly reduced.

NT-proBNP, an established circulating blood marker of cardiac wall stress, significantly decreased to ranges closer to normal (considered less than 125 pg/mL). NT-proBNP levels in HCM subjects of <310 pg/mL have been associated with a 75 percent reduction in the rate of heart failure-related death or hospitalization, progression to end-stage disease, and stroke, as compared with subjects with levels≥310 pg/mL.

E/e', an echocardiographic measure of left ventricular filling pressure, decreased from a mean baseline measure of 12.8 to 9.1.

Left atrial volume index decreased to normal levels from a baseline mean of 41 mL/$m^2$ to a mean of 32 mL/$m^2$. Left atrial volumes are a measure of the filling pressure of the left ventricle, and increased volumes are potentially associated with an increased risk of atrial fibrillation in HCM subjects.

Reductions in interventricular septal (IVS) thickness as measured by echocardiography were observed in PIONEER-OLE subjects. Overall, PIONEER-OLE subjects began the study with a mean IVS of 17 mm at baseline, and progressively decreased to 15 mm after 48 weeks of mavacamten treatment. Studies of HCM subjects post-septal reduction interventions have shown that IVS reductions in HCM subjects are associated with improvements in LVOT gradient, functional capacity and symptoms. The risk of sudden cardiac death in HCM subjects has been observed to increase progressively as wall thickness increases above 15 mm.

Figure 3A:
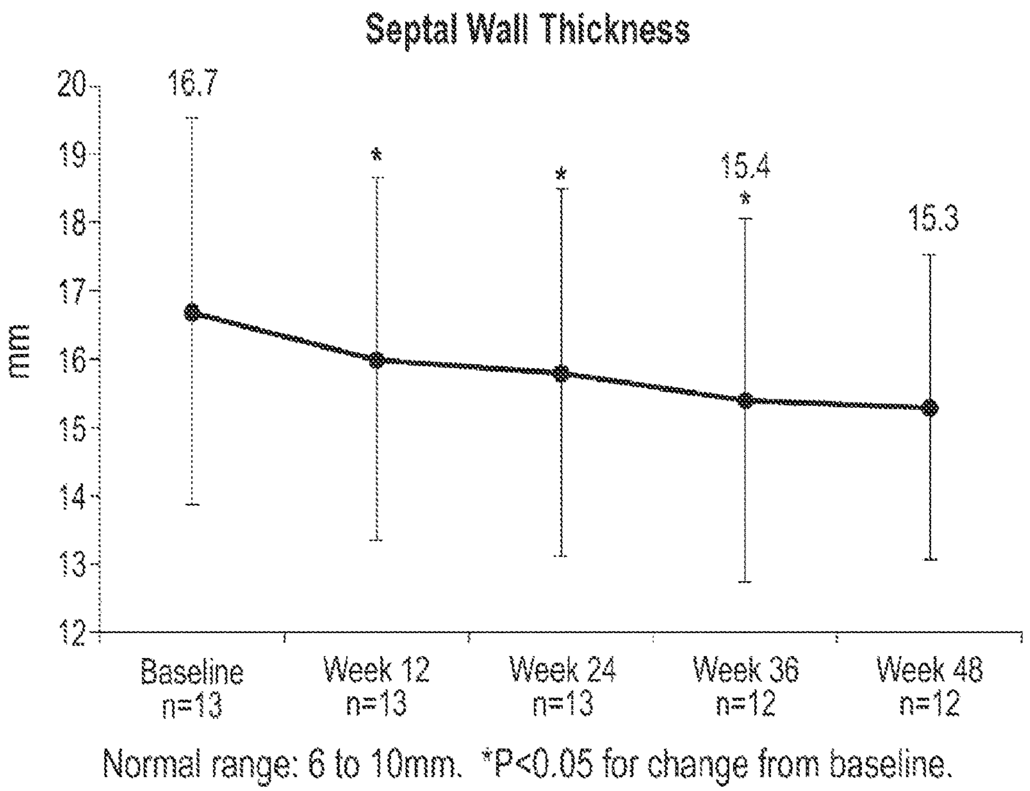
FIG. 3A is a plot of septal wall thickness measurements over 48 weeks in the study of Example 1.
Figure 3B:
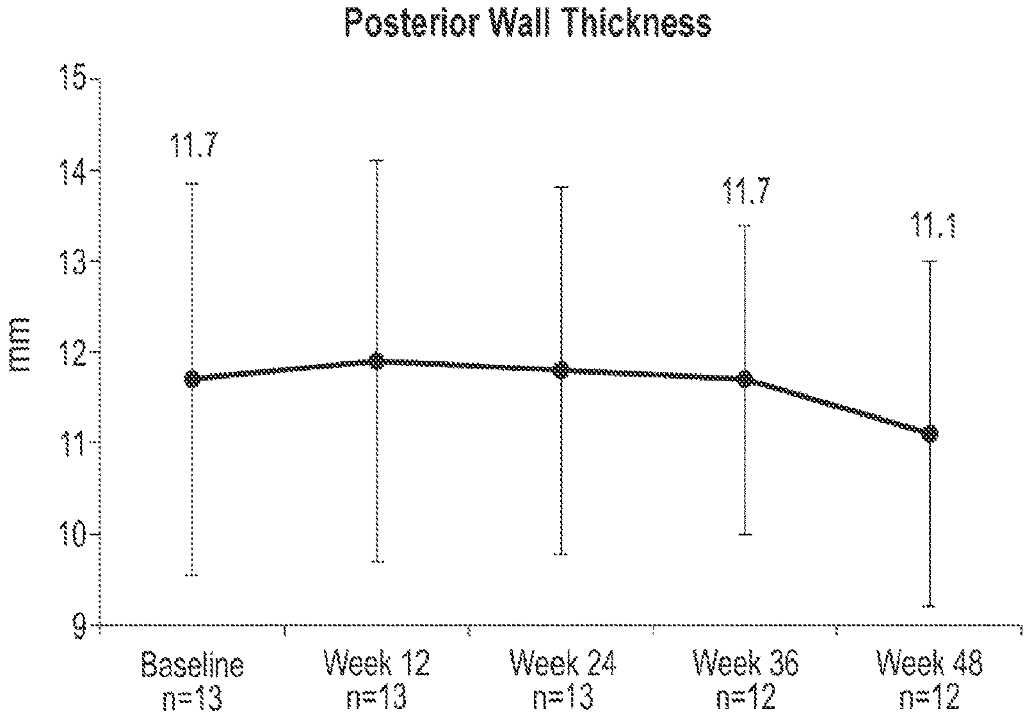
FIG. 3B is a plot of posterial wall thickness measurements over 48 weeks in the study of Example 1.

For the first time, the data below shows that interventricular septal thickness was reduced in humans at Week 12, 24, 36, and 48, by a myosin inhibitor without changes in posterior wall thickness. See Table 1.1, Table 1.2, and FIGS. 3A and 3B for biomarker measurements, mean (SD), cardiac wall stress, diastole, and structural changes.

Significant reductions were seen in serum levels of NT-proBNP. The median serum NT-proBNP level was 136.5 pg/mL at Week 48, resulting in a change from baseline of −472 pg/mL (P=0.0005). A similar reduction in median NT-proBNP levels was seen at Week 60 (change from baseline of −481 pg/mL, P=0.0005). For exploratory assessments, mavacamten improved markers related to ventricular filling. There was a significant increase in $e'_{lat}$ (mean change from baseline of 1.6 cm/s, P=0.002) and concomitant reduction in $E/e'_{lat}$ (mean change from baseline of −3.4, P=0.001). There was a significant decrease in LA volume index at Week 48 (mean change from baseline of −9.8 mL/$m^2$, P=0.0269). Systolic anterior motion of the mitral valve was noted in 12 of 13 patients at baseline and in 4 of 12 evaluable patients by Week 48.

TABLE 1.1

| | Normal ranges | Baseline (N = 13) | Week 12 (N = 13) | Week 24 (N = 13) | Week 36 (N = 12) | Week 48 (N = 12) | Change from Baseline to Week 48 |
|---|---|---|---|---|---|---|---|
| NT-proBNP (pg/mL), median (IQR) | <125 | 594 | 99 | 93 | 168 | 137 | −472 (−2467, −157)** |
| e'lat, cm/s, mean ± SD | >12 | 6.4 ± 1.3 | 8.4 ± 2.3 | 7.9 ± 2.2 | 8.7 ± 2.8 | 8.0 ± 1.6 (n = 11) | 1.6 ± 1.1* |
| E/e' lateral | <13 | 12.8 (±2.9) | 9.8 (±2.5) | 10.2 (±2.7) | 8.5 (±2.3) | 9.1 (±2.0) † | −3.4 (3.0)** |

TABLE 1.1-continued

| | Normal ranges | Baseline (N = 13) | Week 12 (N = 13) | Week 24 (N = 13) | Week 36 (N = 12) | Week 48 (N = 12) | Change from Baseline to Week 48 |
|---|---|---|---|---|---|---|---|
| LA volume index (mL/m2) mean ± SD | 16-34 | 40.9 (±16.4) | 31.8 (±8.4) | 30.8 (±8.0) | 30.4 (±8.7) | 31.5 (±6.9) | −9.8 (±13.5)* |
| IVS (mm) | 6-10 mm | 16.7 (2.8) | 16.0 (2.7) | 15.8 (2.7) | 15.4 (2.7) | 15.3 (2.2) | −1.5 (2.6) |
| Systolic anterior motion of the mitral valve present (Y/N n (%) | N/A | 12 (92.3) | 6 (46.2) | 6 (46.2) | 7 (58.3) | 4 (33.3) | — |

**$p < 0.01$;
*$p < 0.05$;
"†" = n is 11

Mavacamten was associated with reductions in interventricular septal thickness over 48 weeks (mean change from baseline of −1.2 mm, P=0.1294) without any notable changes in posterior wall thickness. Significant reductions in LV mass index (mean change from baseline of −16.3 g/m$^2$, P=0.021) and LV maximum wall thickness (mean change from baseline of −1.4 mm, P=0.0259) were also seen at Week 48.

TABLE 1.2

| Parameter | Baseline N = 13 | Week 12 N = 13 | Week 24 N = 13 | Week 36 N = 12 | Week 48 N = 12 |
|---|---|---|---|---|---|
| Interventricular septal thickness, mm | | | | | |
| Mean ± SD | 16.6 ± 2.9 | 15.9 ± 2.7 | 15.8 ± 2.7 | 15.4 ± 2.7 | 15.5 ± 2.0 |
| Change from baseline, mean ± SD | — | −0.7 ± 0.7 | −0.7 ± 1.1 | −1.2 ± 1.7 | −1.2 ± 2.3 |
| P value | — | 0.0007 | 0.0215 | 0.0425 | 0.1294 |
| LV posterior wall thickness, mm | | | | | |
| Mean ± SD | 11.7 ± 2.2 | 11.9 ± 2.2 | 11.8 ± 2.0 | 11.7 ± 1.7 | 11.1 ± 1.9 |
| Change from baseline, mean ± SD | — | 0.2 ± 0.8 | 0.2 ± 0.9 | 0.0 ± 1.5 | −0.5 ± 1.9 |
| P value | — | 0.3757 | 0.8394 | 0.8501 | 0.4697 |
| LV mass index, g/m$^2$ | | | | | |
| Mean ± SD | 103.0 ± 25.8 | 101.1 ± 26.1 | 99.4 ± 25.1 | 95.8 ± 22.3 | 86.0 ± 18.7 |
| Change from baseline, mean ± SD | — | −1.9 ± 8.0 | −3.6 ± 15.6 | −6.4 ± 17.5 | −16.3 ± 20.3 |
| P value | — | 0.4548 | 0.2163 | 0.3013 | 0.0210 |
| LV maximum wall thickness, mm | | | | | |
| Mean ± SD | 20.9 ± 2.1 | 20.1 ± 2.5 | 19.1 ± 2.4 | 19.0 ± 2.2 | 19.4 ± 2.7 |
| Change from baseline, mean ± SD | — | −0.8 ± 2.0 | −1.8 ± 1.8 | −1.8 ± 1.9 | −1.4 ± 2.2 |
| P value | — | 0.0596 | 0.0034 | 0.0054 | 0.0259 |

Example 2. Chronic Effect of MYK-581 in a Min-Pig Genetic Model of Non-Obstructed Hypertrophic Cardiomyopathy: In Vivo Evidence for Improved Relaxation and Functional Reserve Introduction: Hypertrophic cardiomyopathy (HCM) is a heritable disease characterized by cardiac remodeling, impaired relaxation, and exertional intolerance. Direct myosin-attenuation with mavacamten can normalize contractility and improve exercise capacity in subjects with obstructed HCM, providing sustained symptomatic relief. However, mavacamten and its surrogate MYK-581 can also improve relaxation by limiting residual cross-bridges during diastole, and therefore, may offer cardiac benefits beyond obstruction reprieve. This in vivo study evaluated the chronic effects of MYK-581 in a genetic large-animal model of non-obstructed HCM.

Figure 4:
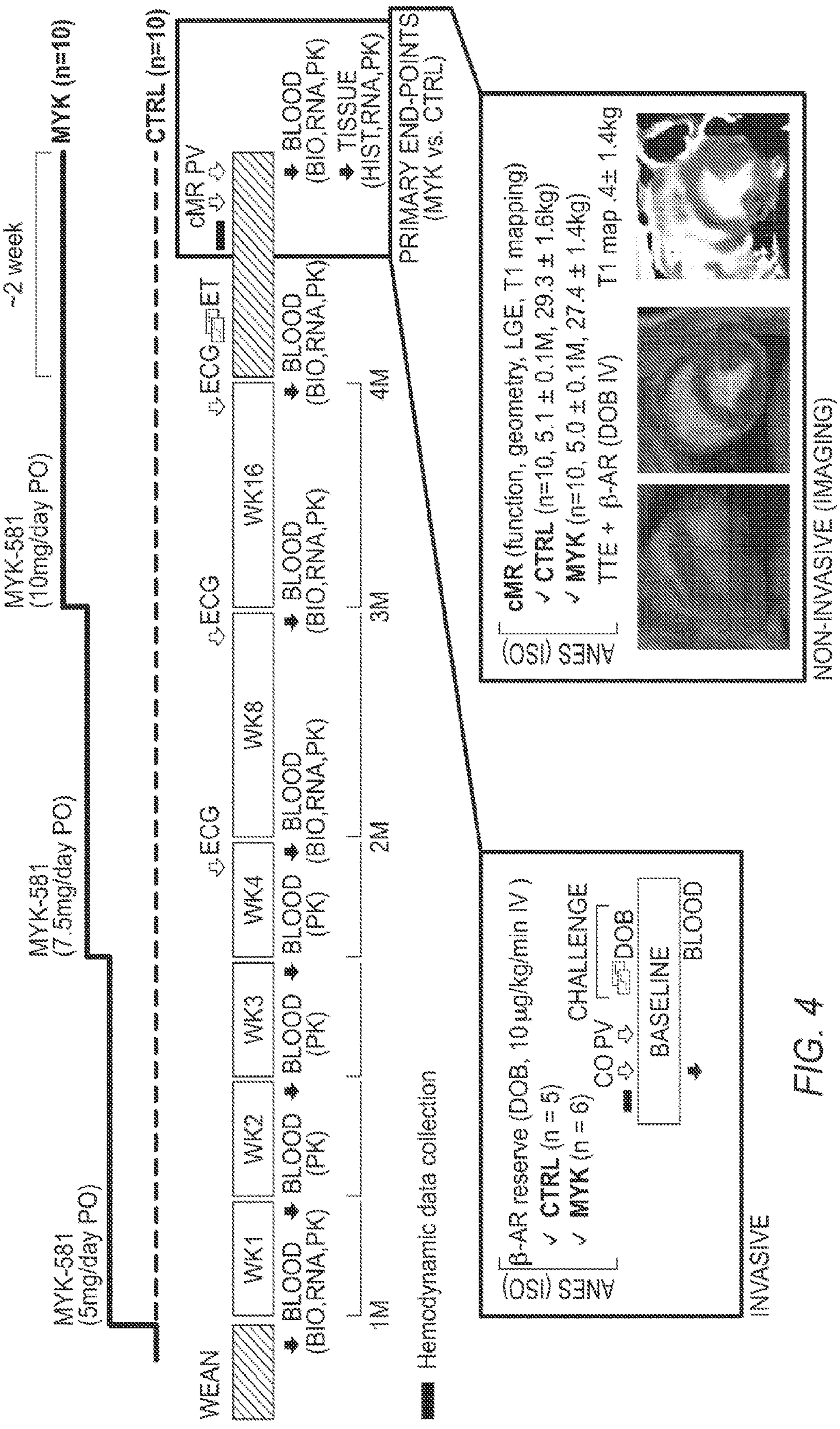
FIG. 4 is a scheme for the study of Example 2.

Methods: Young cloned Yucatan mini-pigs with a heterozygous MYH7 R403Q mutation were randomly assigned to one of two arms: time-controls (n=10) or daily MYK-581 (n=10; PO). The mini-pigs were treated for at least 12 weeks and were evaluated as shown in Schematic 1 below. Treated animals received progressively increasing MYK-581 doses (5, 7.5, and 10 mg/day PO) to account for weight gain 6.4±0.3 to 28.3±1.1 kg (P<0.05) as shown in Schematic 1 below. After ~14 weeks of treatment, all pigs underwent in vivo cMR imaging for the assessment of LV function and geometry, as well as of myocardial composition via of Late Gadolinium Enhancement (LGE) and T1 mapping techniques including extracellular volume (ECV) assessments. In addition, a subset of animals (MYK: n=6, CTRL: n=5) also underwent terminal invasive hemodynamics assessments, including cardiac output (CO, via thermodilution), load-independent systolic/diastolic function (via LV pressure-volume relationships), and β-adrenergic (β-AR) cardiac reserve (via dobutamine at 5 ug/kg/min IV). See FIG. 4.

The mini-pig model can be obtained following the method disclosed in a presentation entitled "A Minipig Genetic Model of Hypertrophic Cardiomyopathy Uncovers the Pathophysiological Mechanisms of Disease Evolution", by E. Green et al., at University of Iowa, Carver College of Medicine.

Results:

In R403Q mutant pigs, MYK-581 treatment decreased ($P<0.05$) both EF (59±2 vs. 65±2%) and LV mass (51±4 vs. 66±5 g), while preserving CO. Treated pigs had smaller left-atrial volumes (16±1 vs. 29±4 mL, $P<0.05$) with lower T1-times and ECV (27±1 vs. 32±2%, $P<0.05$), suggesting improved LV structure/compliance. Indeed, the MYK-group had lower ($P<0.05$) LV end-diastolic pressures (9±1 vs. 23±4 mmHg) and stiffness (1.3±0.2 vs. 3.5±0.3 mmHg/mL) with faster time-constants of relaxation (45±3 vs. 71±5 ms, $P<0.05$). Treatment also rescued β-AR stroke-volume recruitment (+15±4 vs. −14±6%, $P<0.05$).

Result 1 Chronic MYK-581 Normalized Diastole a. Chronic MYK-581 preserved end-diastolic pressures (EDP)/stiffness ($E_{ed}$)

Improved compliance and early relaxation ($tau_w$; dP/dt).

b. Chronic MYK-581 rescued β-AR cardiac reserve (dobutamine challenge):

↑ SV (CTRL: −14±6% vs. MYK: +15±4%, $P<0.05$)

↑ CO (CTRL: +26±2% vs. MYK: +60±8%, $P<0.05$)

Figure 5A:
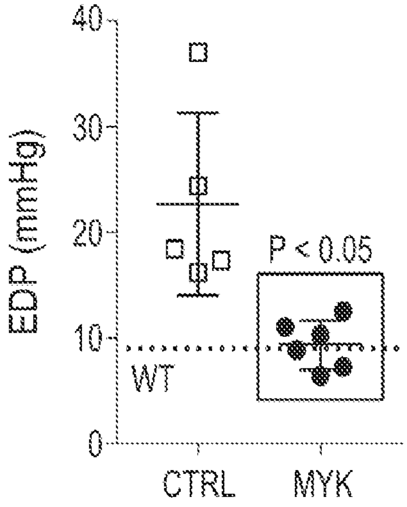
FIG. 5A is a plot of EDP (end-diastolic pressures) for MYK-581 versus control.
Figure 5B:
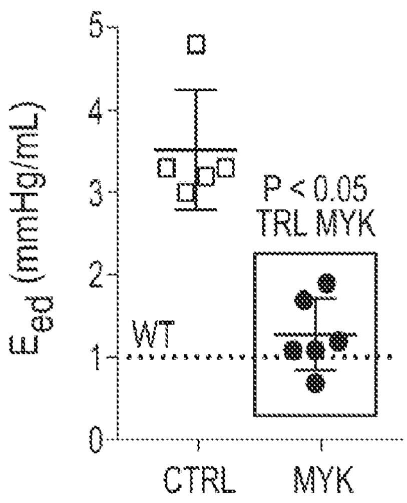
FIG. 5B is a plot of $E_{ed}$ (stiffness) for MYK-581 versus control.
Figure 5C:
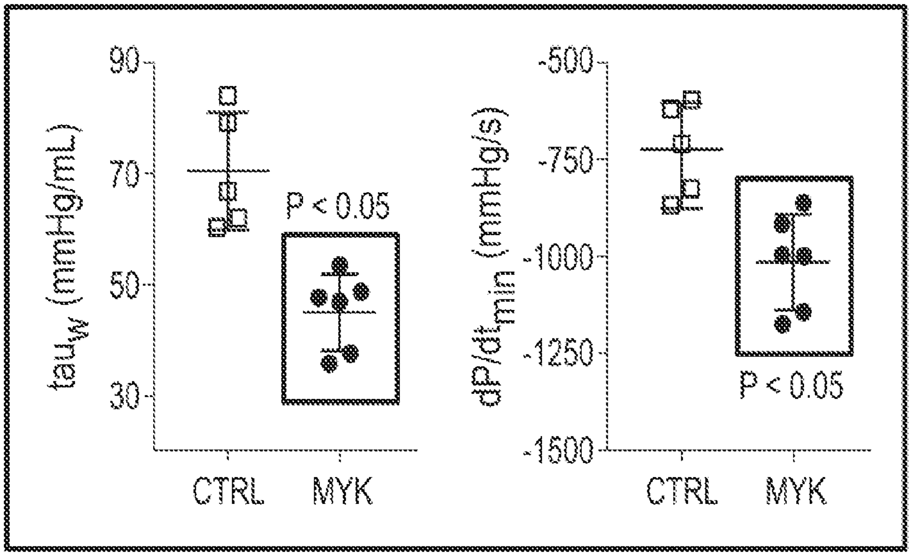
FIG. 5C shows side-by-side plots for $tau_W$ and $dP/dt_{min}$ for MYK-581 versus control, demonstrating improved compliance and early relaxation.
Figure 6A:
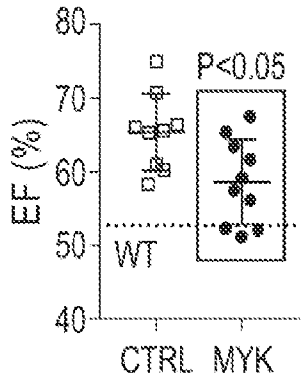
FIG. 6A is a plot of ejection fraction (EF) from the study of Example 2.
Figure 6B:
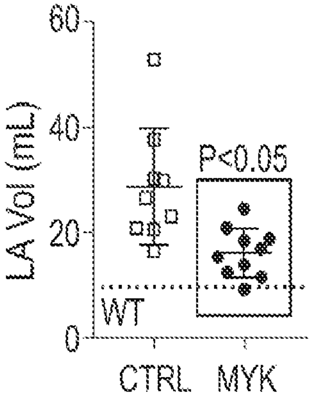
FIG. 6B is a plot of left atrial (LA) volume from the study of Example 2.
Figure 6C:
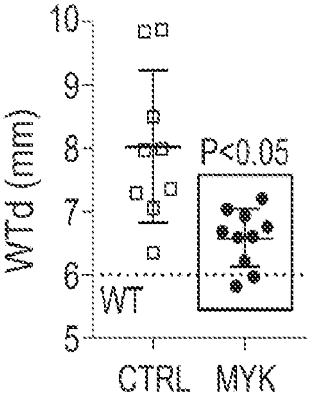
FIG. 6C is a plot of $WT_d$ (diastolic wall thickness over the left ventricle) from the study of Example 2.
Figure 6D:
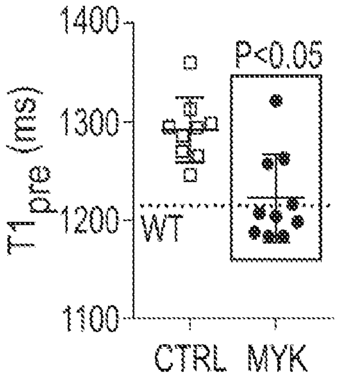
FIG. 6D is a plot of $T1_{pre}$ from the study of Example 2.
Figure 6E:
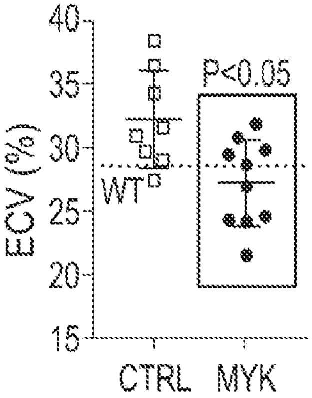
FIG. 6E is a plot of extracellular volume (ECV) from the study of Example 2.
Figure 6F:
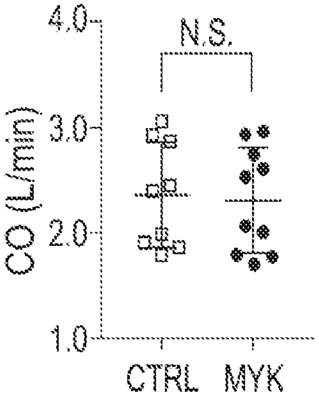
FIG. 6F is a plot of cardiac output (CO) from the study of Example 2.
Figure 6G:
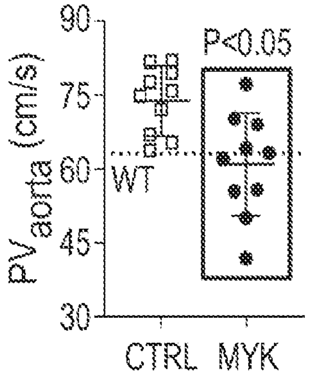
FIG. 6G is a plot of $PV_{aorta}$ from the study of Example 2.
Figure 6H:
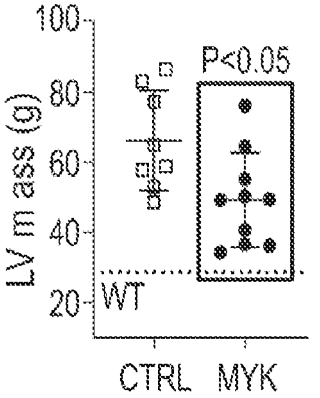
FIG. 6H is a plot of left ventricular (LV) mass from the study of Example 2.
Figure 6I:
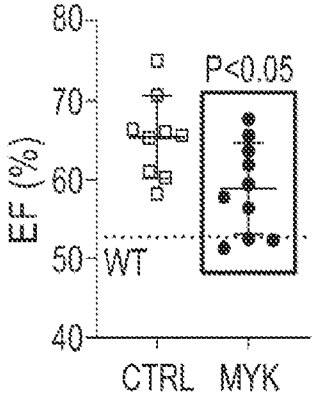
FIG. 6I is a plot of ejection fraction (EF) from the study of Example 2.

The Result 1 indicates a preserved ability of the myocardium to respond to stress, which suggests a potential ability to preserve exercise capacity. Also see FIGS. 5A-C.

Result 2 Chronic MYK-581 Normalized Cardiac Phenotype a. Chronic MYK-581 reduced hyper-contractility, while preserving cardiac output, both via cMR and thermodilution b. Chronic MYK-581 preserved LA volume (LA vol), blunting increases in average diastolic wall thickness over the left ventricle (WTd) and LV mass gain (LV mass)

c. Chronic MYK-581 preserved LV structure (reduced T1 and ECV)

d. Improved mortality (trend): CTRL: 40% vs. MYK 0% at the end of the study (~5 months).

See FIGS. 6A-I.

Chronic direct myosin attenuation with a mavacamten surrogate, MYK-581, prevented cardiac remodeling characteristic of disease in a genetic HCM model and reduced mortality. Chronic treatment improved diastolic function and cardiac reserve while reducing left atrial size, a known prognostic indicator in HCM. These observations suggests potential salutary effects beyond obstruction relief in subjects with HCM and that early and chronic administration of mavacamten suppresses the development of ventricular hypertrophy, cardiomyocyte disarray, attenuates hypertrophic gene expression.

From this chronic pig study, we observed total plasma concentrations between 30 and 140 ng/mL. After correcting for species differences in plasma protein binding, and potency differences between MYK-581 and mavacamten, the observed levels in pig translate to human plasma concentrations in a range of 50-250 ng/mL that would be expected to have equivalent effects. From our understanding of mavacamten PK, this in turn translates to doses in the range of 1-5 mg QD, which is approximately 2-5 fold lower than the doses required to relieve obstruction in humans.

Figure 21A:
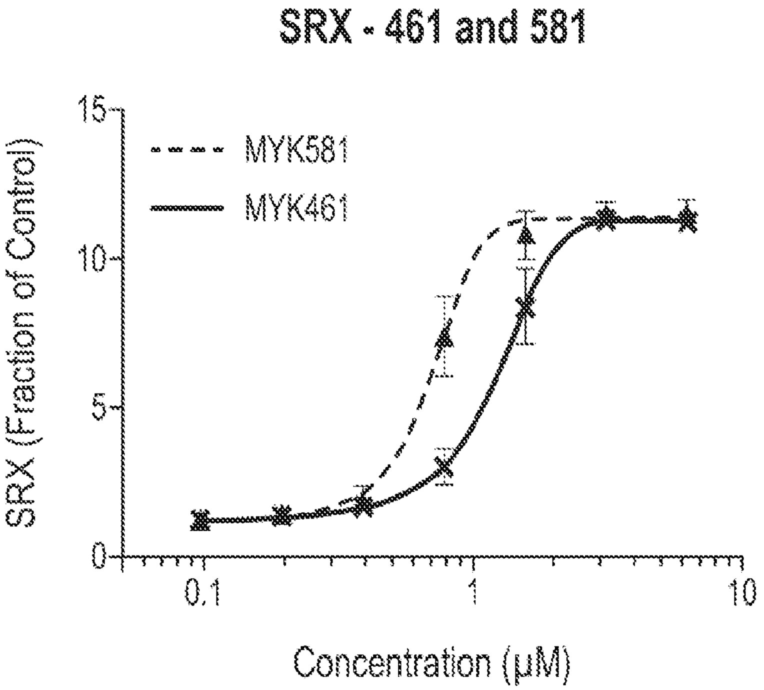
FIG. 21A is a chart of SRX versus concentration for mavacamten (MYK-461) and MYK-581.
Figure 21B:
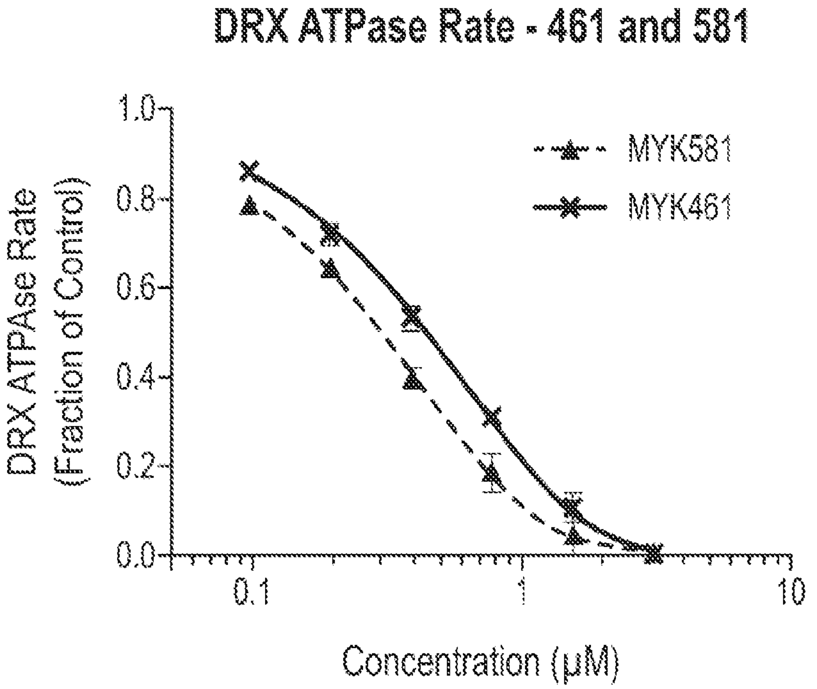
FIG. 21B is a chart of DRX ATPase rate versus concentration.
Figure 21C:
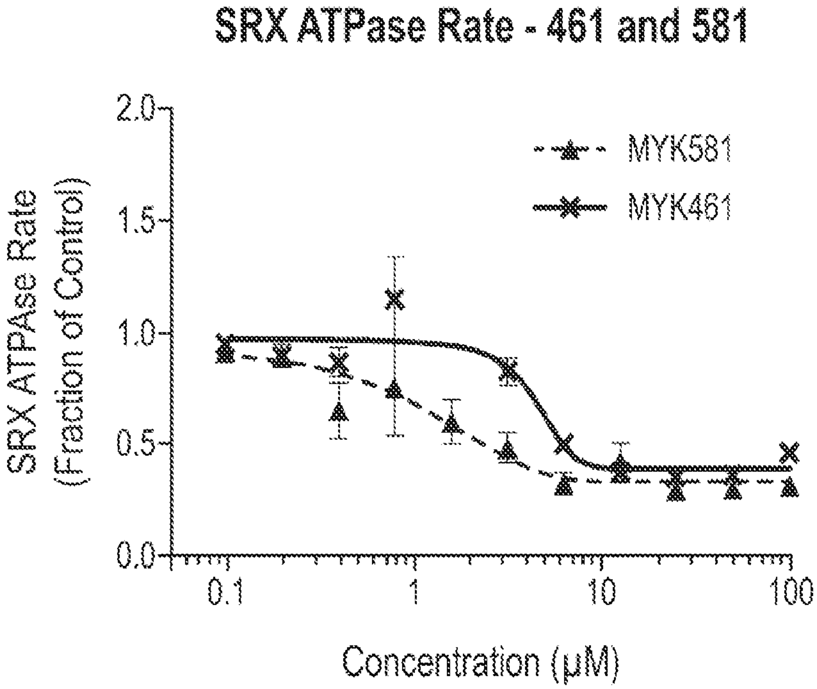
FIG. 21C is a chart of SRX ATPase rate versus concentration.

Comparative studies of MYK-581 and mavacamten have shown that these two compounds behave alike in terms of ATPase inhibition and populating super relaxed states (SRX). Particularly, studies of MYK-581 and mavacamten in bovine cardiac synthetic myosin filaments showed similar DRX ATPase rate and SRX ATPase Rate (as a fraction of control) for the two compounds over a range of concentrations. See FIGS. 21A-C. Due to these similarities, mavacamten is expected to provide like benefits in the measures related to nHCM in this Example 2.

Example 3. MAVERICK-HCM TRIAL: A Randomized, Double-blind, Placebo-controlled, Concentration-Guided Study, Exploratory Study of Mavacamten in Subjects with Symptomatic Non-obstructive Hypertrophic Cardiomyopathy (nHCM) and Preserved Left Ventricular Ejection Fraction This is a Phase 2 trial designed to assess the safety and tolerability of a range of exposures over 16 weeks of treatment in subjects with symptomatic, non-obstructive HCM. All study subjects were required to be diagnosed with non-obstructive HCM, with left ventricular wall thickness either ≥15 mm or ≥13 mm with a family history of HCM, LVEF≥55%, NYHA classifications of Class II or III, and NT-proBNP levels of greater than 300 pg/mL at rest. Baseline characteristics, such as age, weight, gender, pathogenic mutation status, background beta blocker use, NYHA classification and exercise capacity were approximately evenly distributed between active and placebo arms.

Study Objective:

(a) Primary Objective: To evaluate safety and tolerability of a 16-week course of mavacamten in individuals with symptomatic nHCM.

(b) Exploratory:

1. To evaluate the effect of a 16-week course of mavacamten on exercise capacity as measured by peak oxygen uptake (VO2),
2. To evaluate the relationship of mavacamten concentration to pharmacodynamic response (eg, echocardiographic measures of diastolic and systolic function),
3. To assess the effect of a 16-week course of mavacamten on symptoms and quality of life,
4. To assess the effect of a 16-week course of mavacamten on circulating levels of N-terminal pro b-type natriuretic peptide (NT-proBNP),
5. To assess effect of a 16-week course of mavacamten on daily activity level as measured by accelerometer,
6. To assess the reversibility of the effects of mavacamten after a 16-week course of the treatment has been discontinued for approximately 8 weeks.

(c) Pharmacokinetic Objective: To characterize the pharmacokinetics (PK) profile of mavacamten.

Methods:

This double-blind study enrolled 59 individuals with nHCM (Left ventricular outflow tract gradient<30 mmHg; resting or provoked), NYHA Class II or III, and LVEF≥55%. Subjects were randomized 1:1:1 to one of two target plasma drug concentrations (Group 1: ~200 ng/mL and Group 2: ~500 ng/mL) or placebo for 16 weeks, followed by an 8-week washout. The starting dose of mavacamten was 5 mg daily, with one-step dose titration at Week 6 based on plasma drug concentration. Predefined criteria, including LVEF (LVEF≤45%), guided study drug discontinuation if indicated. Cardiopulmonary exercise testing was performed at baseline and Week 16 to assess the impact on exercise capacity.

Figure 7:
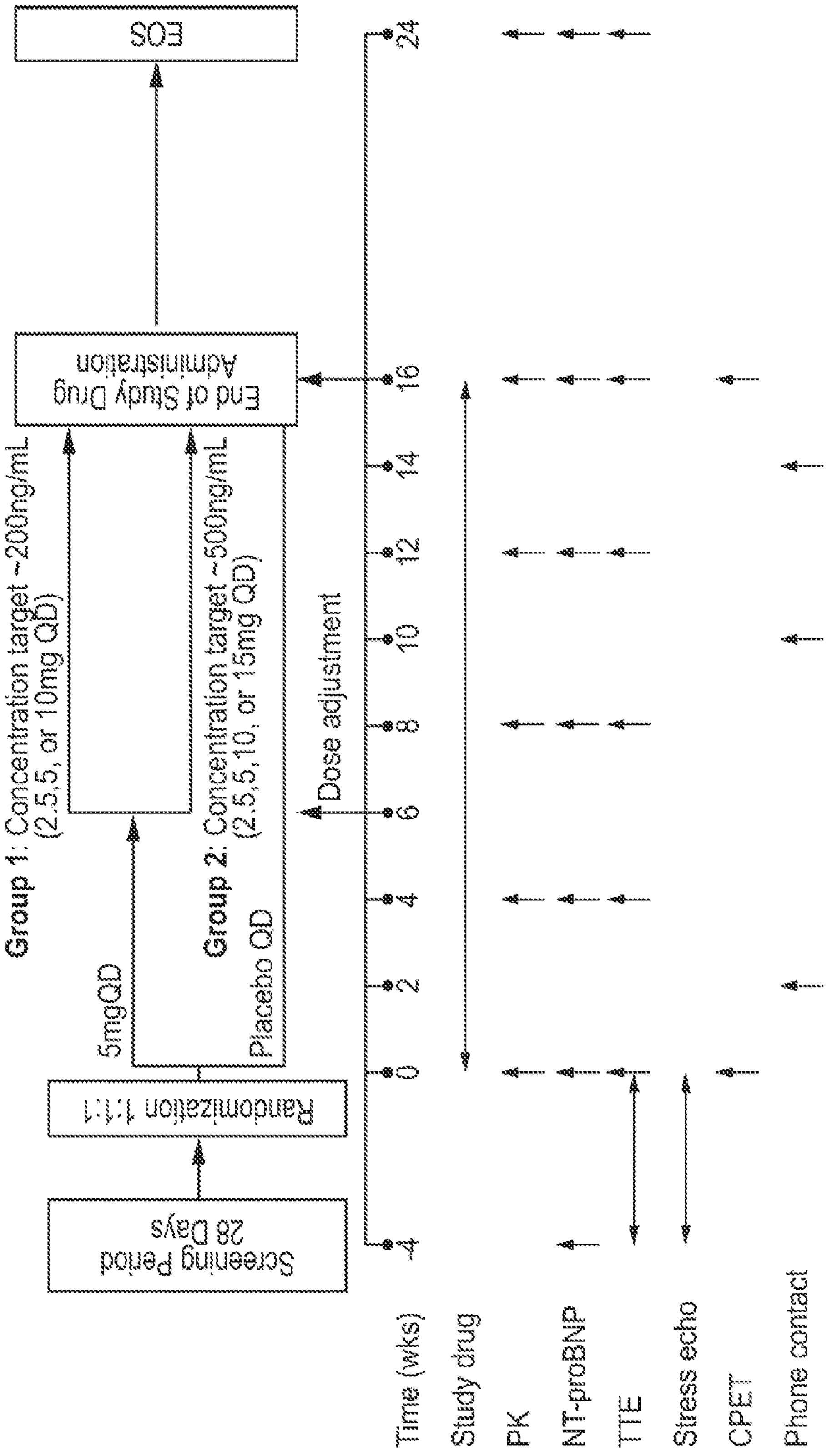
FIG. 7 is a scheme for the study of Example 3.

Study Design and Plan:

This study is to evaluate the safety, tolerability, preliminary efficacy, PD, and PK of 2 target drug concentrations of Mavacamten compared with placebo in subjects with symptomatic nHCM. Study Scheme is shown in FIG. 7.

Approximately 60 subjects with symptomatic nHCM are randomized and receive a 16-week course of Mavacamten doses titrated to achieve 1 of 2 target drug concentrations (Group 1: ~200 ng/mL; Group 2: ~500 ng/mL) or placebo once daily (QD). Dose adjustments will be based on PK parameters. Assessments include safety, standardized cardiopulmonary exercise testing (CPET) with measurement of peak oxygen consumption, echocardiography to evaluate left ventricular ejection fraction (LVEF) and parameters of diastolic function, symptoms, quality of life, daily step counts, and NT-proBNP at rest and after exercise. In addition, subjects may consent to hypertrophic cardiomyopathy genotyping and pharmacogenetic sampling.

For subjects who consented and had prior HCM genotype test results demonstrating a pathogenic mutation known to be associated with HCM, no further genotype assessment were performed if the data could be provided from a clinical laboratory source document and the subject consents to share this information. Subjects who had not been tested and subjects who did not have an HCM genotype test results demonstrating a pathogenic mutation known to be associated with HCM might consent separately to have blood drawn prior to dosing on Day 1 for assessment of HCM genotype. For subjects who consented to pharmacogenetic assessment, blood samples were collected prior to dosing for analysis of genetic biomarkers of efficacy, safety, PD, or PK parameters as determined by future studies, using clinically meaningful endpoints, through additional DNA sequencing or other genetic testing.

Cardiac Troponin I levels were evaluated on plasma and serum samples of subjects at baseline and at various time points in the trial (Abbott Architect Stat Troponin-I assay (Ref. 2K41)). Cardiac Troponin T levels were evaluated on plasma and serum samples of subjects at baseline and at various time points in the trial (Roche Elecsys Troponin T hs assay) (Ref. 08469873190) performed on a cobas e 801 analyzer). NT-proBNP levels were evaluated on plasma samples using the Roche Elecsys proBNPII assay (Ref. 07027664190) on a cobas e 801 analyzer.

Key Inclusion Criteria:

1. Was at least 18 years old at Screening, body weight was greater than 45 kg at Screening,
2. Diagnosed with nHCM (hypertrophied and non-dilated left ventricle in absence of systemic or other known cause) consistent with current American College of Cardiology Foundation/American Heart Association and European Society of Cardiology guidelines, with:
   Left ventricular (LV) wall thickness ≥15 mm, or
   LV wall thickness ≥13 mm with a positive family history of HCM,
3. LV ejection fraction ≥55%,
4. LVOT peak gradient at rest AND during Valsalva AND post-exercise <30 mmHg,
5. Maximal intracavitary gradient at rest AND during Valsalva AND post-exercise <30 mmHg as determined by the echocardiography central laboratory,
6. Has New York Heart Association (NYHA) Class II or III symptoms,
7. Has an elevated NT-proBNP at rest (>300 pg/mL).

Key Exclusion Criteria:

1. Had a known infiltrative or storage disorder causing cardiac hypertrophy that mimics nHCM, such as Fabry disease, amyloidosis, or Noonan syndrome with LV hypertrophy,
2. Has any medical condition that precludes upright exercise stress testing,
3. Had a history of syncope or a history of sustained ventricular tachyarrhythmia with exercise within the past 6 months,
4. Had a history of resuscitated sudden cardiac arrest at any time or known appropriate implantable cardioverter defibrillator (ICD) discharge within 6 months,
5. Had paroxysmal, intermittent atrial fibrillation with atrial fibrillation present per the investigator's evaluation of the subject's electrocardiogram (ECG) at the time of Screening,
6. Had persistent or permanent atrial fibrillation not on anticoagulation for at least 4 weeks prior to Screening and/or is not adequately rate-controlled within 6 months,
7. Was currently treated with disopyramide or ranolazine,
8. Fridericia-corrected QT interval (QTcF)>480 ms or any other ECG abnormality considered to pose a risk to subject safety,
9. For subjects on beta blocker, verapamil, or diltiazem, any dose adjustment<14 days before screening,
10. Currently treated or planned treatment during the study with a combination of beta blocker and verapamil or a combination of beta blocker and diltiazem,
11. Has been treated with invasive septal reduction (surgical myectomy or percutaneous alcohot septal ablation) within 6 months prior to screening,
12. Documented history of resting or post-exercise LVOT or intracavity gradient>30 mmHg unless subsequently treated by septal reduction therapy,
13. Has documented obstructive coronary artery disease (>70% stenosis in one or more epicardial coronary arteries) or myocardial infarction within the past 6 months,
14. Has known moderate or severe aortic valve stenosis at screening,
15. Has pulmonary disease that limits exercise capacity or systemic arterial oxygen saturation,
16. Currently taking, or has taken within 14 days prior to screening, a prohibited medication such as a cytochrome P450 (CYP) 2C19 inhibitor (eg, omeprazole), a strong CYP 3A4 inhibitor, or St. John's Wort.

Study Treatment:

A concentration guided approach was used to evaluate what doses of mavacamten resulted in improvement of diastolic function in nHCM subjects. Subjects were randomized via an interactive response system to 3 groups in a 1:1:1 ratio: 2 active treatment groups and 1 matching placebo.

5 mg QD was used as the starting dose for the study. All subjects in the active treatment groups started on 5 mg QD. Subjects were assessed for plasma concentration of mavacamten in blood samples taken at Week 4 visit. PK modeling was used to guide blinded dose adjustment at the Week 6 visit, based on the plasma concentrations collected at Week 4. Subjects in the placebo group underwent the same assessments in order to preserve the blind. The study drug was provided in mavacamten capsules in available strengths of 2.5 mg, 5 mg, 10 mg and 15 mg. Subjects were instructed to take the drug under fasting conditions, at approximately the same time each day, and with 8 ounces of water.

A target mavacamten blood plasma concentration of 200 ng/mL was the goal in Group 1 subjects. To achieve the target concentration, if a subject's Week 4 concentration was >450 ng/mL, the subject's dose was decreased to 2.5 mg QD; if Week 4 concentration was 110-450 ng/mL, the dose was maintained at 5 mg QD; and if Week 4 concentration was <110 ng/mL, the dose was increased to 10 mg QD.

A target Mavacamten blood plasma concentration of 500 ng/mL was the goal in Group 2 subjects. To achieve the target concentration, if a subject's Week 4 concentration was >450 ng/mL, the subject's dose was decreased to 2.5 mg QD; if Week 4 concentration was 300-450 ng/mL, the dose was maintained at 5 mg QD; if Week 4 concentration was greater than or equal to 175 and less than 300 ng/mL, the dose was increased to 10 mg QD; and if Week 4 concentration was <175 ng/mL, the dose was increased to 15 mg QD.

Subjects were monitored for adverse events (AE), including high blood plasma concentration, systolic dysfunction, QT prolongation, and LVEF decrease. If any of the following thresholds were hit PK 1000 or more, QTcF 500, or LVEF 45%, the subjects were discontinued on drug. Specifically, high blood plasma concentration was defined as blood plasma concentration greater than or equal to 1000 ng/mL; QT prolongation was defined as QTcF greater than or equal to 500 ms; and LVEF shortening was defined as LVEF less than or equal to 45% (including serious adverse event (SAE) for LVEF less than or equal to 30%).

Efficacy and pharmacodynamics assessments were also made. Resting transthoracic echocardiography measurements were taken at Weeks 4, 8, 12 and 16. Ejection fraction (2-D) and LV frantional shortening were analyzed along with other echocardiographic at baseline measures including measure of diastolic function. Post-exercise stress echocardiography was also performed following a standard symptom-limited exercise test performed by the subjects. Instantaneous peak LVOT gradient was assessed immediately post-exercise. Cardiopulmonary exercise testing (CPET) was also performed. CPET was conducted using a standardized treadmill or upright bicycle ergometer on Day 1 and at Week 16. Subjects were encouraged to perform maximally to achieve expected heart rate. Oxygen uptake (VO2), carbon dioxide production (VCO2), volume expired (VE), VE/VO2, ventilatory efficiency (VE/VCO2), respiratory exchange ratio, circulatory power, and metabolic equivalent of the task were assessed.

Pharmacokinetic assessments were also made during the study. Blood samples were collected for mavacamten plasma concentration assessments at Weeks 4, 8, 12 and 16. At Week 16, a predose and postdose PK blood sample was taken.

Study Endpoints:

The primary endpoint is the frequency and severity of treatment-emergent adverse events. Secondary endpoints including echocardiographic measures of diastolic function, NT-proBNP levels, subject reported outcomes, and physical activity by wearable accelerometer.

Exploratory Endpoints:

1. Change from baseline to Week 16 in peak $VO_2$,
2. Change from baseline to Week 16 in echocardiographic measures of systolic function (eg, LVEF),
3. Change from baseline to Week 16 in echocardiographic measures of diastolic function (peak velocity of early diastolic septal and lateral mitral annular motion [e'], ratio of peak velocity of early diastolic transmitral flow [E] to e' [E/e'], ratio of E to peak velocity of late transmittal flow [A] [E/A], pulmonary artery systolic pressure, left atrium size),
4. Change from baseline to Week 16 in NYHA class,
5. Change from baseline to Week 16 in KCCQ scores,
6. Change from baseline to Week 16 in EQ-5D score,
7. Change from baseline to Week 16 in subject-reported severity of HCM symptoms as assessed by the HCMSQ score,
8. Change from baseline to Week 16 in perceived severity of symptoms assessed by the PGIC and PGIS questionnaire scores,
9. Change from baseline to Week 16 in NT-proBNP at rest (prior to exercise) and after maximal exercise,
10. Change from baseline to Week 16 in accelerometer daily step count,
11. Change in echocardiographic measures of diastolic function (e', E/e', E/A, pulmonary artery systolic pressure, left atrium size) from Week 16 to Week 24,
12. Change in NYHA class, KCCQ scores, EQ-5D score, HCMSQ scores, and PGIC and PGIS questionnaire scores from Week 16 to Week 24,
13. Change in NT-proBNP at rest from Week 16 to Week 24.

The composite functional endpoint was also studied and is described below.

Results:

59 participants were randomized 19/21/19 to 200 ng/mL/500 ng/mL/placebo. Baseline characteristics are shown in Table 3.1. 40 participants had a detectable cTnI level and among those, 19 (32%) had an elevated cTnI (>0.03 ng/mL or >99th percentile; 13 participants on mavacamten and 6 participants on placebo). For those with detectable cTnI, baseline geometric mean cTnI level was 0.03 ng/mL in the pooled-mavacamten group and 0.05 ng/mL in placebo. Baseline E/e'$_{average}$ was elevated (>14) in 25 of 59 (42.4%) participants.

TABLE 3.1

Demographics and Baseline Characteristics

| Characteristic | Group 1 mavacamten ~200 ng/ml (n = 19) | Group 2 mavacamten ~500 ng/mL (n = 21) | Pooled mavacamten (n = 40) | Placebo (n = 19) |
|---|---|---|---|---|
| Age, mean years (SD) | 58.3 (13.7) | 50.0 (14.7) | 54.0 (14.6) | 53.8 (18.2) |
| Female sex, n (%) | 9 (47.4) | 12 (57.1) | 21 (52.5) | 13 (68.4) |
| Race, n (%) | | | | |
| Asian | 1 (5.3) | 0 | 1 (2.5) | 0 |
| Black or African American | 1 (5.3) | 1 (4.8) | 2 (5.0) | 0 |
| White | 17 (89.5) | 18 (85.7) | 35 (87.5) | 17 (89.5) |
| Unknown | 0 | 2 (9.5) | 2 (5.0) | 2 (10.5) |
| BMI, kg/m$^2$ (SD) | 28.8 (4.1) | 29.8 (6.1) | 29.3 (5.2) | 31.0 (4.9) |

TABLE 3.1-continued

| Demographics and Baseline Characteristics | | | | |
|---|---|---|---|---|
| Characteristic | Group 1 mavacamten ~200 ng/ml (n = 19) | Group 2 mavacamten ~500 ng/mL (n = 21) | Pooled mavacamten (n = 40) | Placebo (n = 19) |
| Consented to Optional HCM Genotyping, n (%) | 14 (73.7) | 14 (66.7) | 28 (70.0) | 12 (63.2) |
| Pathogenic or Likely Pathogenic HCM Gene Mutation, n (%) of 40 with genetic testing | 7 (50.0) | 7 (50.0) | 14 (50.0) | 8 (66.7) |
| NT-proBNP (pg/mL) | 889 | 763 | 821 | 914 |
| Geometric mean 95% CI | 747, 1575 | 606, 1261 | 790, 1293 | 770, 1558 |
| cTnI (ng/mL) | 0.024 | 0.023 | 0.023 | 0.020 |
| Geometric mean 95% CI | 0, 0.503 | 0.016, 0.080 | 0, 0.253 | 0.013, 0.119 |
| cTnI > 0.03 ng/mL,* n (%) | 6 (31.6) | 7 (33.3) | 13 (32.5) | 6 (31.6) |
| NYHA class, n (%) | | | | |
| Class II | 15 (78.9) | 18 (85.7) | 33 (82.5) | 13 (68.4) |
| Class III | 4 (21.1) | 3 (14.3) | 7 (17.5) | 6 (31.6) |
| Peak $VO_2$ (mL/kg/min), mean (SD) | 19.5 (5.2) | 21.0 (6.6) | 20.4 (6.0) | 17.9 (5.1) |
| Maximal LV Wall Thickness (mm), mean (SD) | 20.9 (3.0) | 20.4 (4.8) | 20.6 (4.0) | 18.8 (3.5) |
| LVEF, % (SD) | 68.0 (5.2) | 69.4 (5.8) | 68.7 (5.5) | 66.4 (7.7) |
| Lateral e' (cm/s) mean (SD) | 8.5 (3.8) | 7.7 (2.6) | 8.1 (3.2) | 7.8 (3.6) |
| Septal e' (cm/s) mean (SD) | 5.3 (2.0) | 4.5 (1.6) | 4.9 (1.8) | 4.4 (1.7) |
| E/e' average, mean (SD) | 13.9 (5.4) | 14.2 (7.7) | 14.1 (6.6) | 18.5 (9.9) |
| LVEDV (mL) mean (SD) | 59.5 (14.5) | 58.5 (18.6) | 58.9 (16.6) | 60.5 (21.6) |
| LA Volume Index ($mL/m^2$), mean (SD) | 40.3 (16.1) | 34.5 (8.9) | 37.3 (13.0) | 40.8 (15.2) |
| Peak gradient (mmHg), mean (SD) | 8.1 (3.3) | 9.4 (3.6) | 8.8 (3.5) | 7.8 (2.5) |
| Background HCM therapy, n (%) | | | | |
| Beta blocker | 12 (63.2) | 13 (61.9) | 25 (62.5) | 12 (63.2) |
| Calcium channel blocker | 5 (26.3) | 5 (23.8) | 10 (25.0) | 3 (15.8) |
| Neither | 3 (15.8) | 3 (14.3) | 6 (15.0) | 4 (21.1) |

*99th percentile, BMI, body mass index; IQR, interquartile range; SD, standard deviation.

The primary study objective was demonstrating safety and tolerability in the subjects with nHCM, which was achieved. The rate of adverse events (AEs) was greater in the mavacamten groups than the placebo group. The majority of AEs and treatment emergent AEs (TEAEs) reported were mild or moderate in severity and reversible or self-resolving. Serious adverse events (SAEs) occurred twice as frequently in the placebo arm (21%) as compared to subjects receiving mavacamten (10%). Transient ejection fraction reductions below the protocol-defined threshold of 45% occurred in five subjects in the active drug arms.

The overall change in LVEF was as follows: [mean % change (SD)]: Group 1-2.3% (5.3); Group 2-5.6% (9.7); Pooled-mavacamten −4.1% (8.0); placebo −2.3% (4.9). Planned echocardiographic assessment at weeks 11-12 identified 5 participants among the 40 receiving active treatment (12.5%; 2 participants in Group 1, 3 in Group 2) with a decrease in LVEF to ≤45% (range 38%-45%), leading to discontinuation of study drug per pre-specified stopping rules. Four of the 5 participants (3 in Group 2 and 1 in Group 1) had undergone the protocol-defined, concentration-targeted dose up-titration from 5 mg to 10 mg at week 6. The fifth participant (Participant 5, Group 1) remained on 5 mg.

Figure 8:
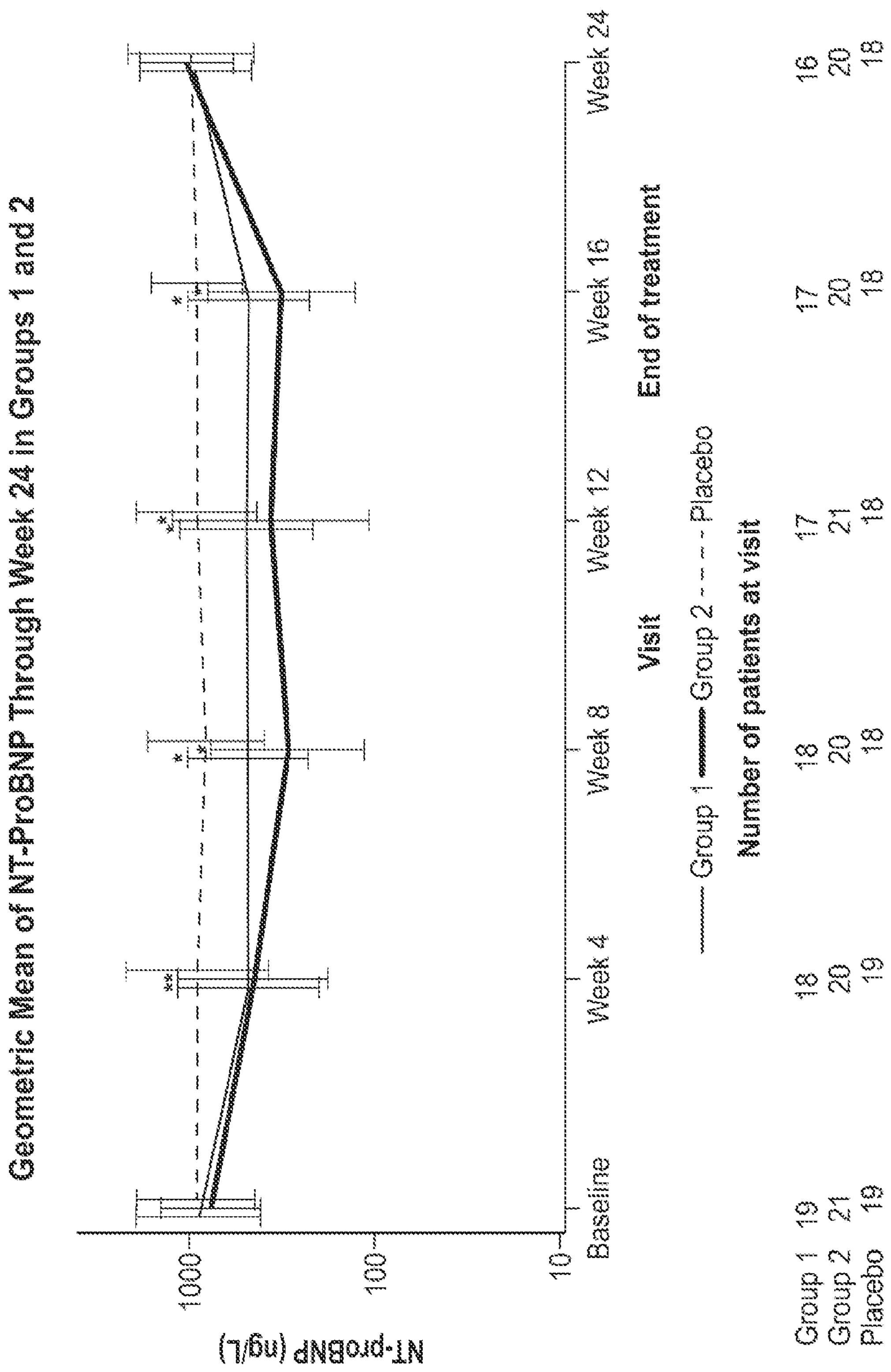
FIG. 8 is a plot of the geometric mean of NT-proBNP through week 24 in Example 3.

For the intent-to-treat population, there was a statistically significant difference at 16 weeks between active and placebo groups in the exploratory endpoint for the biomarker NT-proBNP, for which levels were markedly reduced in subjects receiving mavacamten (p=0.004) across both treatment cohorts, as compared to the placebo group. The NT-proBNP geometric mean at week 16 decreased by 53% in the pooled-mavacamten group (47% in Group 1, 58% in Group 2) vs 1% decrease in placebo with geometric mean differences of −435 pg/mL and −6 pg/mL, respectively (P=0.0005 for the difference between pooled-mavacamten and placebo). See FIG. 8. NT-proBNP in the pooled-mavacamten group was lower than placebo at all timepoints from week 4 to week 16. An initial decline in NT-proBNP was noted at week 4 on 5 mg daily dosing, provided to both groups. Group 2 participants showed a further decrease in NT-proBNP at week 8 (after week 6 titration), consistent with a dose dependent effect. These lower NT-proBNP levels were maintained through week 16 and increased to baseline values at week 24 after the drug was discontinued. NT-proBNP is a well-established biomarker of cardiac wall stress, and elevated NT-proBNP levels are associated with higher risk of heart failure-related death or hospitalization, progression to end-stage disease and stroke. NT-proBNP was measured by Elecsys ProBNP II Immunoassay on Cobas platform.

In subjects with elevated cardiac troponin believed to be at higher risk of morbidity and mortality, meaningful trends suggesting clinical benefit were observed for subjects on treatment versus placebo across multiple endpoints of symptoms, function, biomarkers of cardiac stress and diastolic compliance.

Additionally, similar trends were observed in a subgroup of subjects with elevated cardiac filling pressures (measured by E/e'), suggesting improvement driven by reduced left ventricular pressure, consistent with mavacamten's targeted mechanism.

In addition to a consistent safety profile, the trial establishes that it was able to identify a subject profile with diastolic dysfunction that could achieve benefit from mavacamten treatment. Three million people in the United States have diseases of diastolic dysfunction, referred to as HFpEF, who historically have been addressed as a single group and treated in an undifferentiated manner. With data from the MAVERICK trial, it can now subtype these subjects—both those with HCM and those w/o HCM—and advance development of mavacamten in a "precision", efficient fashion.

For subjects having elevated troponin levels, there was an observed numerical improvement in the combined treated group (Group 1 and Group 2) compared to placebo in several parameters (see asterisked parameters in the Table below) and especially with respect to the medial E/e' ratio (resting), average E/e' ratio (resting), serum NT-proBNP, and Peak VO2. See Table 3.2 below. Elevated troponin levels have been linked with cardiac magnetic resonance imaging evidence of myocardial fibrosis, a well-defined prognostic factor in HCM.

TABLE 3.2

| | Elevated Troponin | | | Other | | |
|---|---|---|---|---|---|---|
| Endpoints | MYK-461 (N = 13) Mean | Placebo (N = 6) Mean | Mean Difference | MYK-461 (N = 27) Mean | Placebo (N = 13) Mean | Mean Difference |
| Peak VO2 (mL/kg/min)* | 1.475 | −1.220 | 2.695 | −0.530 | 1.277 | −1.807 |
| NYHA Class* | −0.462 | −0.200 | −0.262 | −0.417 | −0.538 | 0.122 |
| Lateral E/E' Ratio, Resting* | −2.258 | 0.325 | −2.583 | −0.304 | −1.650 | 1.346 |
| Medial E/E' Ratio, Resting* | −3.169 | 3.875 | −7.044 | −3.896 | −3.900 | 0.004 |
| Average E/E' Ratio, Resting* | −2.754 | 2.075 | −4.829 | −2.492 | −2.767 | 0.275 |
| LV End-Diastolic Volume Index (mL/m2), Resting | 0.791 | 0.750 | 0.042 | 2.623 | −0.709 | 3.332 |
| LV Mass Index (g/m2), Resting* | −6.639 | −1.941 | −4.698 | −3.564 | −7.886 | 4.322 |
| LA Volume Index (mL/m2), Resting | 0.899 | −0.934 | 1.833 | 1.631 | −0.767 | 2.398 |
| Serum NT-proBNP (ng/L)* | −950.462 | −166.400 | −784.062 | −280.667 | −102.154 | −178.513 |
| Serum Troponin I (ng/mL) | −0.123 | −0.040 | −0.083 | −0.003 | 0.001 | −0.004 |
| Overall KCCQ Summary Score | 6.410 | 4.514 | 1.896 | 2.210 | 6.705 | −4.495 |
| Clinical KCCQ Summary Score* | 6.891 | −1.875 | 8.766 | 1.195 | 7.159 | −5.964 |
| Average Daily Accelerometry Unit* | 136328 | −214019 | 350347 | 82413 | −210744 | 293157 |

Figure 9:
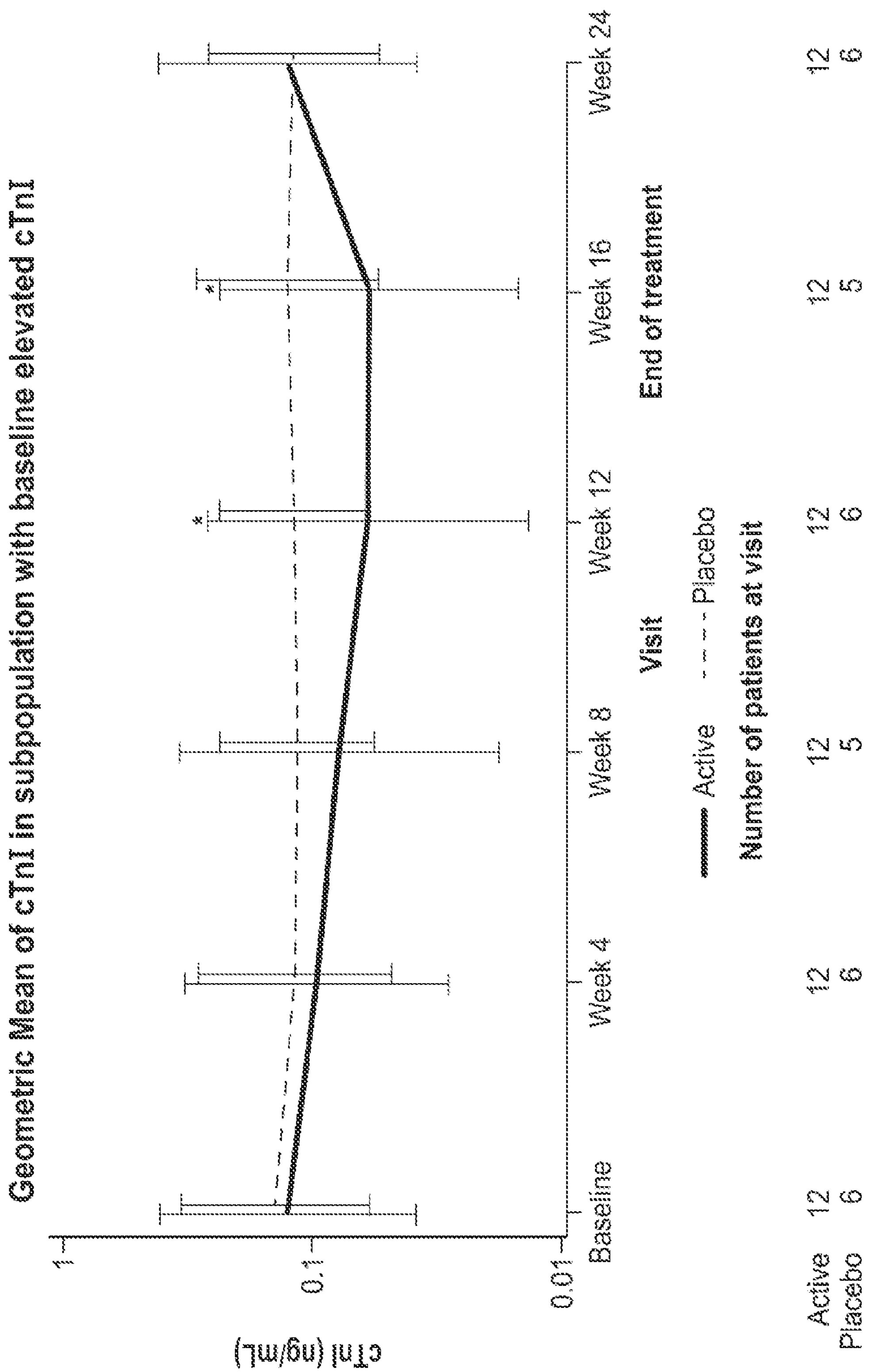
FIG. 9 is a plot of the geometric mean of cTnI in subpopulation with elevated cTnI through week 24 in Example 3.
Figure 10:
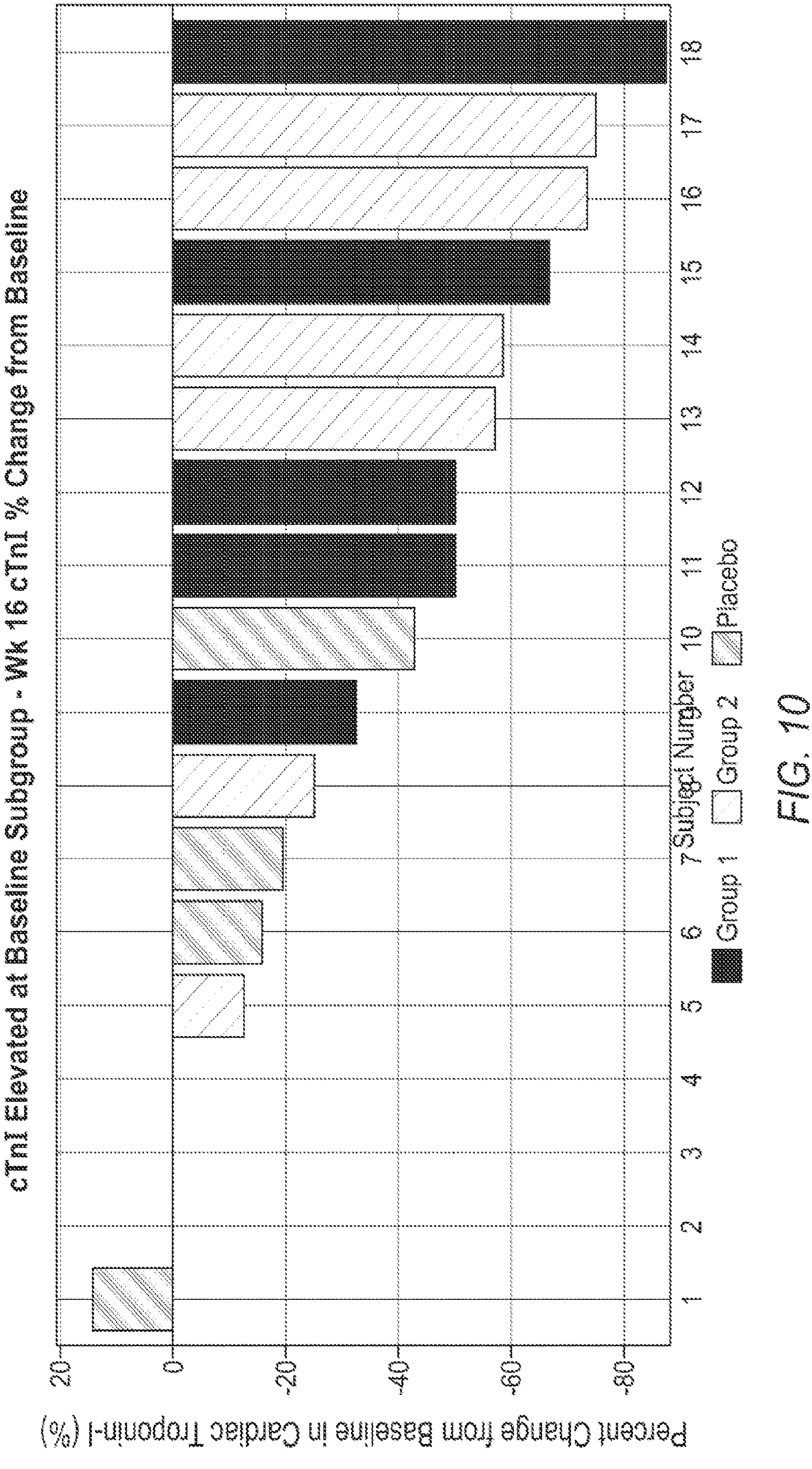
FIG. 10 is a bar chart of the percent change from baseline in cTnI at week 16 in the subpopulation with elevated cTnI in Example 3.

Additionally, in the subgroup with elevated cardiac troponin I (cTnI) subgroup at baseline, cTnI levels decreased in 11 of 13 (84.6%) study subjects at week 16 compared to baseline and remained unchanged in 2 of 13 (15.4%). The % reduction in the 11 of 13 with reductions ranged from 12.5% to 75.0%. The treated individuals demonstrate a 30-80% percentage change in cardiac troponin I from baseline. After study drug was stopped at week 16, cTnI levels in the pooled-mavacamten group increased to baseline by week 24. See FIGS. 9 and 10. That treatment was associated with significant dose-dependent reductions in NT-proBNP and cTnI suggests improvement in myocardial wall stress and cardiac injury in nHCM patients and generally suggests a physiological benefit. cTnI was measured using Abbott Stat Architect platform.

In the intent-to-treat (ITT) population, there was also a significant decrease in cTnI levels. The cTnI geometric mean at Week 16 decreased by 34% in the pooled-mavacamten group vs a 4% increase in placebo with geometric mean differences of −0.008 ng/mL and +0.001 ng/mL, respectively (P=0.009). See Table 3.3. After study drug was stopped at week 16, cTnI levels in the pooled mavacamten group increased to baseline by week 24.

TABLE 3.3

Change in Efficacy and Pharmacodynamic Parameters in the ITT Population

| Parameter, Mean (SD) | Group 1 Mavacamten ~200 ng/mL (n = 19) | Group 2 Mavacamten ~500 ng/mL (n = 21) | Pooled mavacamten (n = 40) | Placebo (n = 19) |
|---|---|---|---|---|
| LVEF (%) | −2.30 (5.30) | −5.61 (9.65) | −4.09 (8.02) | −2.31 (4.94) |
| 95% CI | −5.03, 0.42 | −10.13, −1.09 | −6.77, −1.42 | −4.85, 0.23 |
| P value | 0.91 | 0.42 | 0.45 | — |
| Lateral e' (cm/s) | 0.34 (2.57) | 1.46 (3.55) | 0.94 (3.15) | 0.32 (2.37) |
| 95% CI | −0.99, 1.66 | −0.20, 3.12 | −0.11, 1.99 | −0.94, 1.59 |
| P value | 0.66 | 0.10 | 0.35 | — |
| Septal e' (cm/s) | 0.64 (1.63) | 1.60 (1.49) | 1.17 (1.61) | 0.41 (1.20) |
| 95% CI | −0.21, 1.48 | 0.92, 2.27 | 0.64, 1.69 | −0.23, 1.05 |
| P value | 0.79 | 0.02 | 0.14 | — |
| $E/e'_{lat}$ ratio | −0.71 (2.73) | −1.13 (4.85) | −0.94 (3.97) | −1.16 (6.37) |
| 95% CI | −2.12, 0.69 | −3.40, 1.14 | −2.26, 0.39 | −4.55, 2.24 |
| P value | 0.81 | 0.41 | 0.43 | — |
| $E/e'_{sep}$ ratio | −1.42 (3.56) | −5.45 (10.03) | −3.65 (8.00) | −1.96 (9.11) |
| 95% CI | −3.25, 0.41 | −10.0, −0.88 | −6.28, −1.02 | −6.81, 2.90 |
| P value | 0.74 | 0.25 | 0.46 | — |
| $E/e'_{average}$ ratio | −1.51 (2.44) | −3.45 (6.78) | −2.58 (5.33) | −1.56 (6.449) |
| 95% CI | −2.77, −0.26 | −6.54, −0.36 | −4.33, −0.83 | −4.993, 1.880 |
| P value | 0.72 | 0.28 | 0.50 | — |
| LVEDV (mL) | 1.15 (10.9) | 6.50 (13.5) | 4.04 (12.5) | −0.35 (10.4) |
| 95% CI | −4.45, 6.75 | 0.19, 12.8 | −0.12, 8.2 | −5.68, 4.97 |
| P value | 0.46 | 0.12 | 0.22 | — |
| LA vol (index) ($mL/m^2$) | 0.25 (7.23) | 2.40 (9.13) | 1.39 (8.25) | −0.82 (8.72) |
| 95% CI | −3.47, 3.97 | −2.00, 6.80 | −1.40, 4.18 | −5.30, 3.67 |
| P value | 0.85 | 0.88 | 0.90 | — |
| Peak $VO_2$ (mL/kg/min) | 0.36 (3.12) | 0.12 (3.76) | 0.22 (3.44) | 0.58 (2.39) |
| 95% CI | −1.44, 2.16 | −1.75, 1.99 | −1.02, 1.46 | −0.60, 1.77 |
| P value | 0.87 | 0.67 | 0.93 | — |
| NYHA Class | −0.6 (0.7) | −0.3 (0.6) | −0.4 (0.7) | −0.4 (0.6) |
| 95% CI | −1.0, −0.2 | −0.5, −0.3 | −0.7, −0.2 | −0.8, −0.1 |
| P value | 0.42 | 0.51 | 0.95 | — |
| NT-proBNP* (%) | | | | |
| Geometric mean | −47.1 | −57.9 | −53.2 | −0.7 |
| P value | 0.01 | 0.001 | 0.0005 | — |
| cTnI* (%) | | | | |
| Geometric mean | −23.4 | −41.0 | −34.0 | 3.8 |
| P value | 0.09 | 0.003 | 0.009 | — |
| Overall KCCQ Summary Score | 0.35 (8.71) | 6.24 (10.73) | 3.82 (10.24) | 6.02 (17.63) |
| 95% CI | −4.68, 5.38 | 1.22, 11.26 | 0.24, 7.39 | −3.38, 15.42 |
| P value | 0.52 | 0.48 | >0.99 | — |
| Clinical KCCQ Summary Score | 0.11 (7.67) | 5.66 (10.01) | 3.37 (9.41) | 4.34 (16.05) |
| 95% CI | −4.32, 4.54 | 0.97, 10.34 | 0.09, 6.66 | −4.22, 12.89 |
| P value | 0.96 | 0.40 | 0.47 | — |

*Percent change is presented.

Figure 11A:
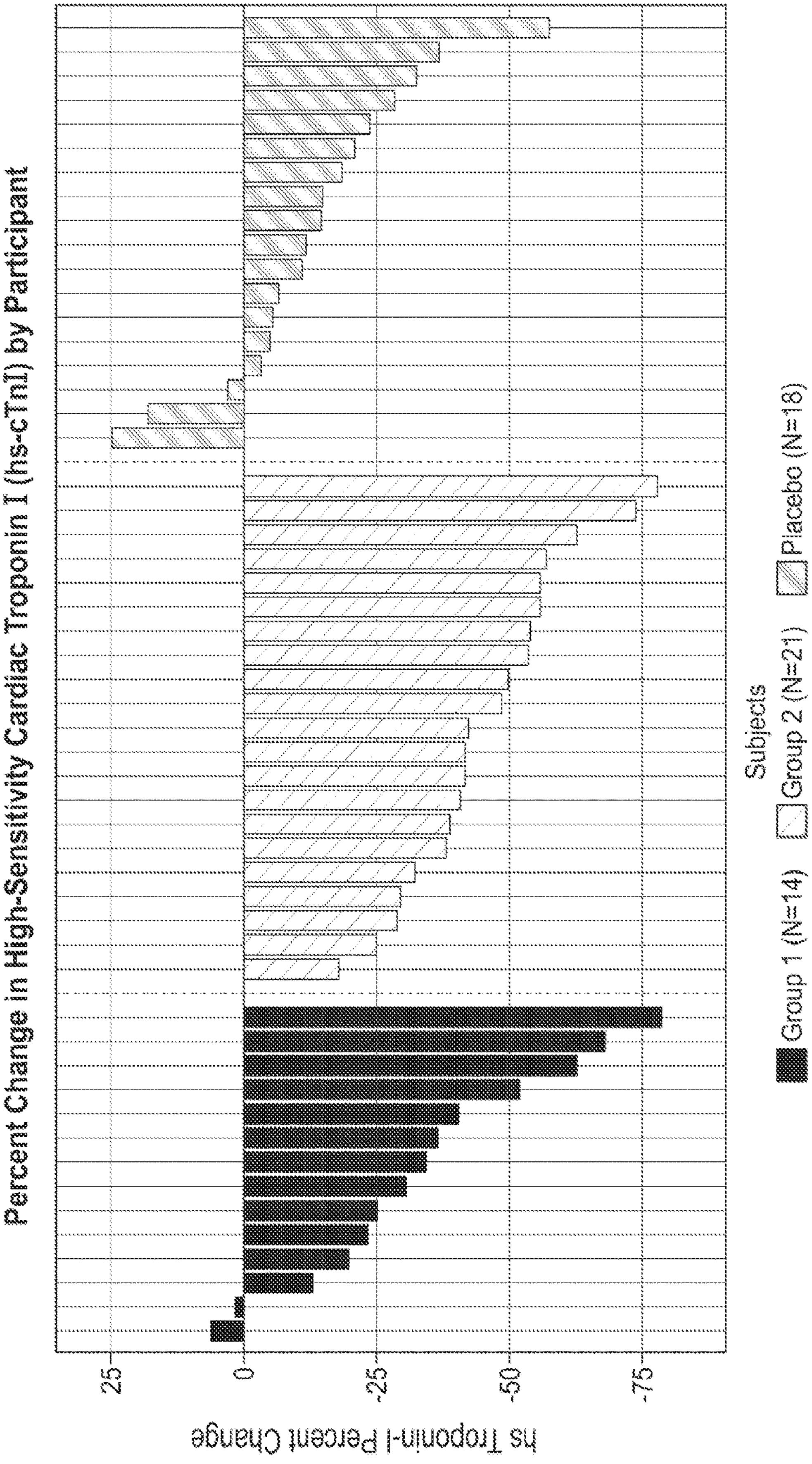
FIG. 11A is a bar chart of the percent change in hs-cTnI by participant in Example 3.
Figure 11B:
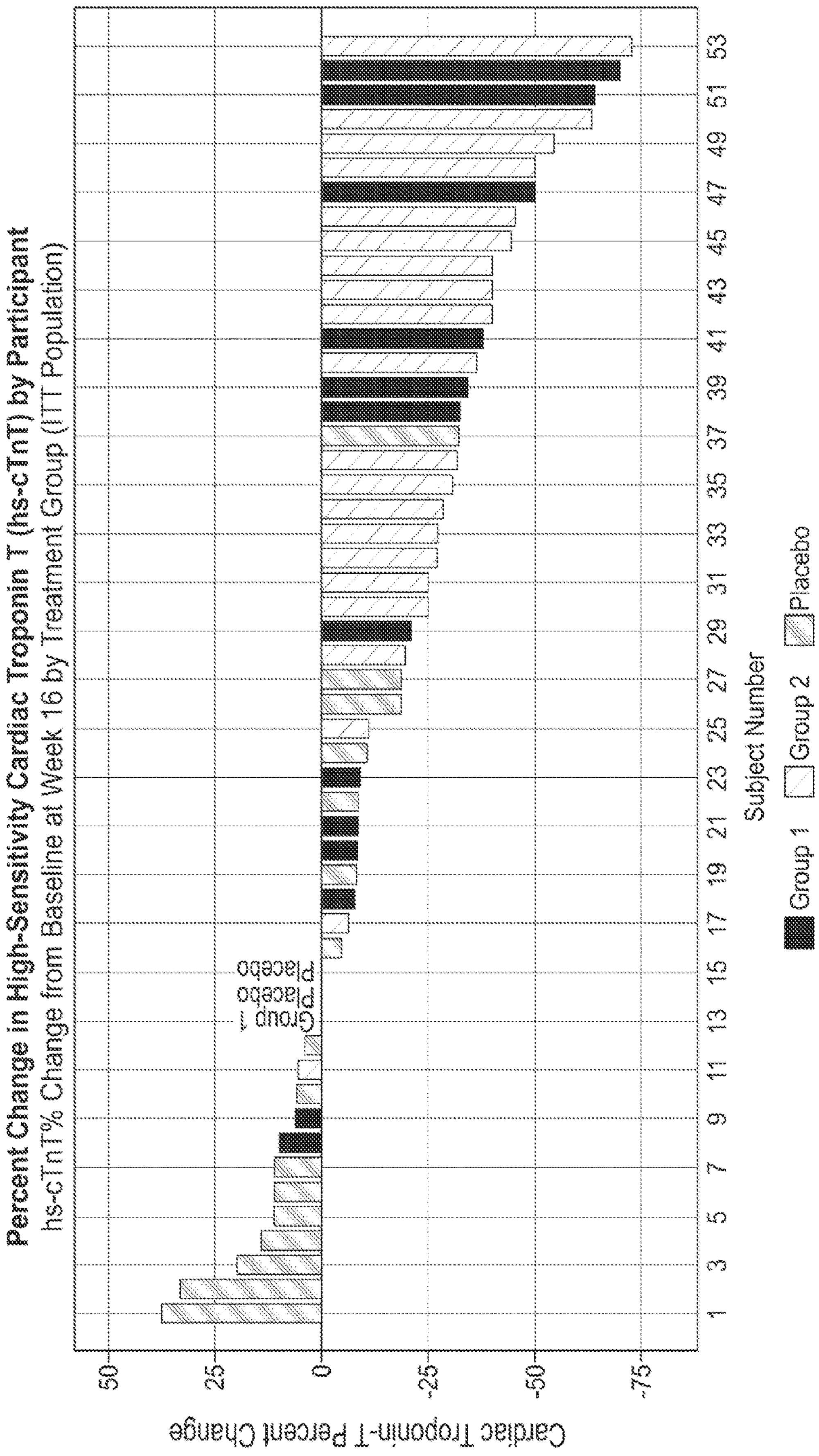
FIG. 11B is a bar chart of the percent change in hs-cTnT by participant in Example 3.

Post-hoc analyses of high sensitivity cTnI (hs-cTnI) were performed on banked serum samples from baseline and week 16 using an ADVIA Centaur XPT immunoassay system (Siemens). The results from hs-cTnI confirmed the reduction in cTnI with mavacamten treatment. See FIG. 1A. Results from hs-cTnT were also confirmatory of the trend in reduction of cardiac troponin levels. See FIG. 11B. The hs-cTnT assay was also performed on the banked serum samples from baseline and week 16 using an ADVIA Centaur XPT immunoassay system (Siemens).

Figure 12:
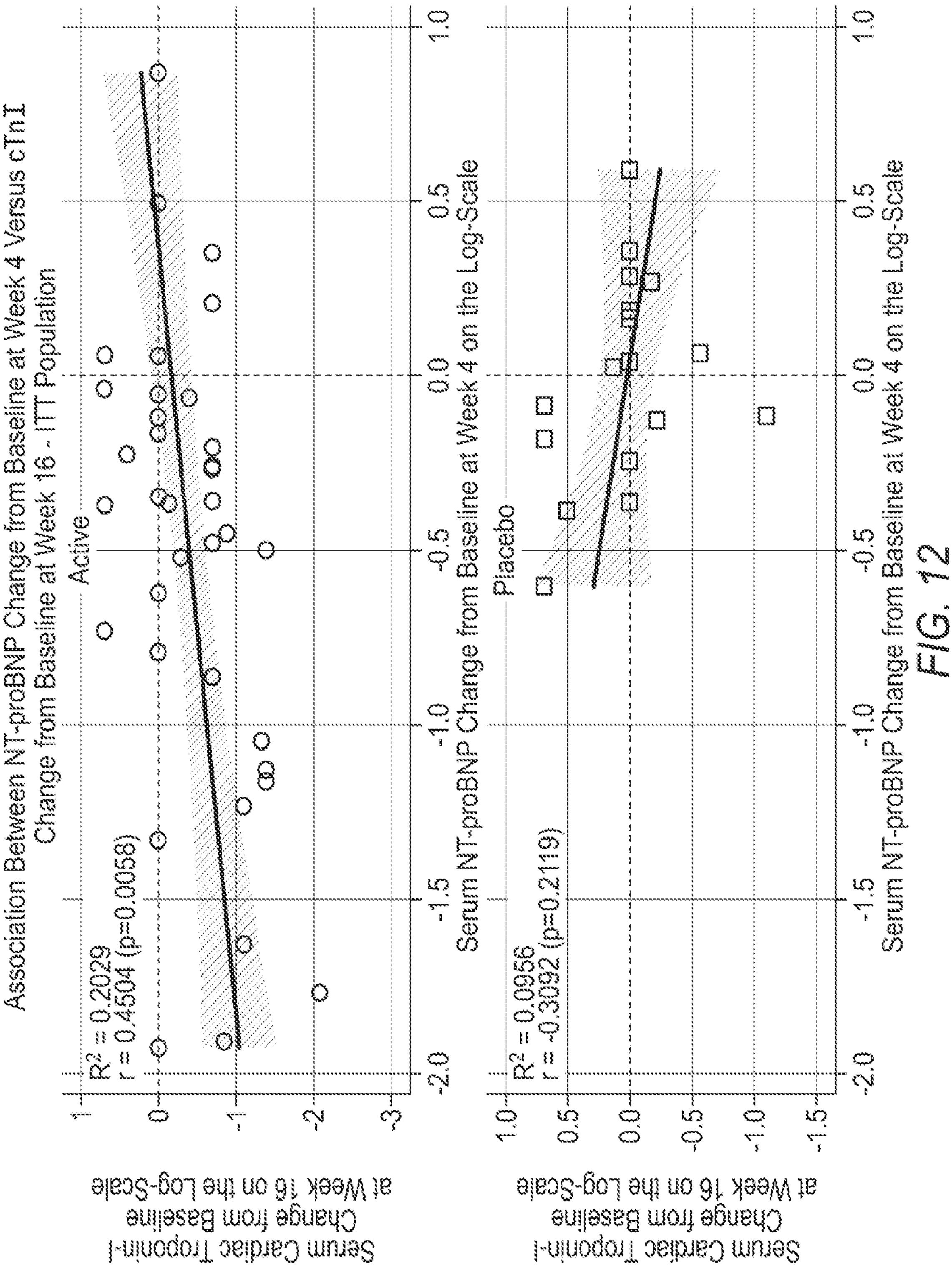
FIG. 12 shows plots depicting the association between NT-proBNP change from baseline at week 4 versus cTnI.

In the pooled-mavacamten group, there was a statistically significant correlation between the change in NT-proBNP at week 4 and the change in cTnI at week 16 (r=0.45, P=0.006). See FIG. 12. No significant correlation was seen in the placebo group (r=−0.31, P=0.212).

Change from baseline in key efficacy and pharmacodynamic parameters in participants with the elevated baseline cTnI is presented in Table 3.4.

TABLE 3.4

Change from Baseline in Efficacy and Pharmacodynamic Parameters in the Subgroup with Elevated cTnI at Baseline

| Parameter | Pooled mavacamten (n = 13) Mean (SD) | Placebo (n = 6) Mean (SD) | Difference mavacamten vs placebo, Mean (95% CI) |
|---|---|---|---|
| Peak $VO_2$ (mL/kg/min) | 1.47 (3.05) | −1.22 (1.94) | 2.70 (−0.48, 5.87) |
| NYHA Class | −0.5 (0.8) | −0.2 (0.5) | −0.3 (−1.1, 0.5) |
| $E/e'_{lat}$ Ratio | −2.3 (5.1) | 0.3 (1.1) | −2.6 (−6.0, 0.8) |
| $E/e'_{sep}$ Ratio | −3.2 (8.7) | 3.9 (4.9) | −7.0 (−16.9, 2.8) |
| $E/e'_{average}$ Ratio | −2.8 (6.6) | 2.1 (3.0) | −4.8 (−12.2, 2.5) |
| LVEDVi ($mL/m^2$) | 0.79 (7.69) | 0.75 (8.43) | 0.042 (−8.92, 9.00) |
| LA Volume Index | 0.9 (11.1) | −0.9 (5.7) | 1.8 (−9.5, 13.1) |
| NT-proBNP (ng/L) | −951 (1040) | −166 (496) | −784 (−1826, 258) |
| cTnI (ng/mL) | −0.12 (0.23) | −0.04 (0.04) | −0.083 (−0.23, 0.063) |
| Overall KCCQ Summary Score | 6.4 (11.2) | 4.5 (11.3) | 1.9 (−10.7, 14.5) |
| Clinical KCCQ Summary Score | 6.9 (9.7) | −1.9 (9.1) | 8.8 (−1.9, 19.4) |

Elevated cTnI defined as >0.03 ng/mL (>$99^{th}$ percentile).

Exploratory analyses were performed to assess the impact of 16 weeks of mavacamten treatment on echo parameters of diastolic function (E/e', e' velocity) and the composite functional endpoint, which was defined as:

1) an improvement of at least 1.5 mL/kg/min in $pVO_2$ and a reduction of 1 or more NYHA Class, or
2) an improvement of at least 3.0 mL/kg/min in $pVO_2$ with no worsening in NYHA Class.

Standardized CPET-based $pVO_2$ was determined at baseline and week 16 by a core laboratory (Cardio-metabolic Diagnostic Research Institute, Palo Alto, CA). In the ITT population, no significant changes were identified in E/e' or e' velocity across treatment groups. For participants with the elevated baseline E/e', change from baseline in key efficacy and pharmacodynamic parameters is presented in Table 3.5.

TABLE 3.5

Change from Baseline in Efficacy and Pharmacodynamic Parameters in the Subgroup with Elevated E/e' at Baseline

| Parameter | Pooled mavacamten (n = 14) Mean (SD) | Placebo (n = 11) Mean (SD) | Difference mavacamten vs placebo Mean (95% CI) |
|---|---|---|---|
| Peak $VO_2$ (mL/kg/min) | 1.2 (3.5) | −0.7 (1.8) | 1.9 (−0.7, 4.4) |
| NYHA Class | −0.4 (0.8) | −0.4 (0.7) | 0.0 (−0.6, 0.7) |
| $E/e'_{lat}$ Ratio | −2.8 (4.8) | −2.4 (8.3) | −0.4 (−6.1, 5.3) |
| $E/e'_{sep}$ Ratio | −8.7 (11.0) | −3.3 (12.0) | −5.4 (−15.5, 4.8) |
| $E/e'_{average}$ Ratio | −6.4 (6.7) | −2.9 (8.3) | −3.6 (−10.1, 3.0) |
| LVEDVi ($mL/m^2$) | 2.8 (7.0) | −1.1 (5.7) | 3.9 (−1.7, 9.4) |
| LA Volume Index | 2.8 (6.3) | −0.2 (9.2) | 3.0 (−3.7, 9.8) |
| NT-proBNP (ng/L) | −656 (1103) | −301 (520) | −355 (−1060, 350) |
| cTnI (ng/mL) | −0.09 (0.23) | −0.02 (0.04) | −0.07 (−0.20, 0.07) |
| Overall KCCQ Summary Score | 4.7 (8.6) | 4.4 (8.8) | 0.4 (−7.4, 8.2) |
| Clinical KCCQ Summary Score | 4.6 (8.7) | 0.5 (8.1) | 4.1 (−3.5, 11.8) |

Figure 13:
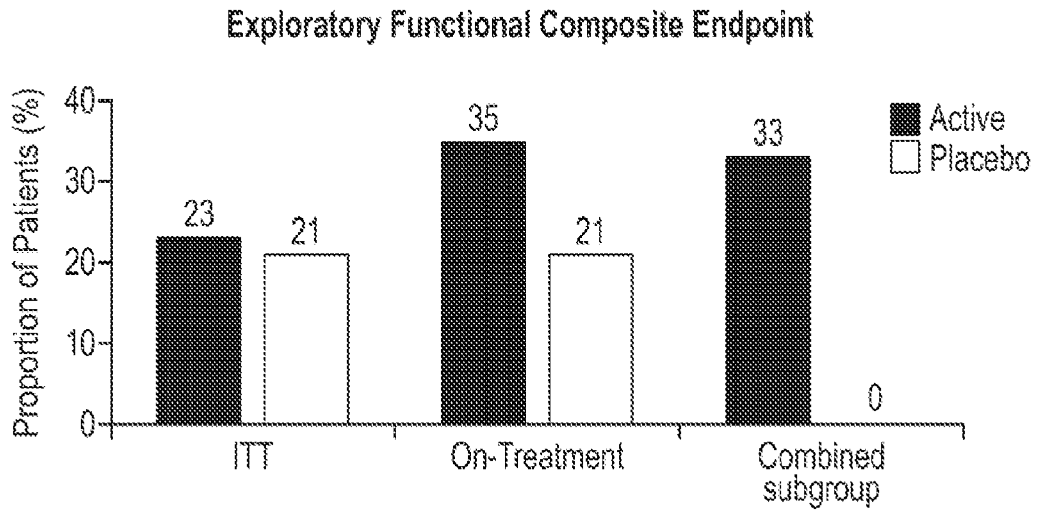
FIG. 13 is a bar chart of the exploratory function composite endpoint of Example 3.

There was no clear difference observed in the proportion of participants achieving the composite functional endpoint in the ITT group—Group 1, 16%; Group 2, 29%; placebo, 22% of participants (p>0.05). However, when analyzing a subgroup of participants with elevated cTnI (>99th percentile) or E/e' average (>14) at baseline (21 participants on mavacamten and 12 participants on placebo) (the "combined subgroup"), 33% of mavacamten-treated participants met the composite functional endpoint, while none of the placebo-treated participants achieved this (P=0.03). See FIG. 13 and Table 3.6. Thus, in the initial exploratory analysis of this subset of participants with more severe disease expression (reflected by baseline elevated E/e' and/or baseline elevated cTnI), mavacamten therapy was associated with improved $pVO_2$ and/or NYHA Class. Based on the data in Table 3.4 and 3.5, there appear to be favorable trends across multiple biomarkers and parameters of symptoms and function, including: Elevated troponin subgroup: peak $VO_2$, NYHA, E/e', and KCCQ; and Elevated E/e' subgroup: peak $VO_2$, E/e', LVEDV, and KCCQ. Accordingly, this subgroup may benefit most from mavacamten therapy.

TABLE 3.6

Composite Functional Endpoint* in the Combined Subgroup (i.e., with Baseline Elevated cTnI or E/e' average >14).

| Parameters | Group 1 mavacamten ~200 ng/mL (n = 9) | Group 2 mavacamten ~500 ng/mL (n = 12) | Pooled mavacamten (n = 21) | Placebo (n = 12) |
|---|---|---|---|---|
| Met endpoint, either type, n (%) | 3 (33.3) | 4 (33.3) | 7 (33.3) | 0 |
| 95% CI | 7.5, 70.1 | 9.9, 65.1 | 14.6, 57.0 | 0, 26.5 |
| P value | 0.0456 | 0.0336 | 0.0287 | — |
| Type 1, n (%) | 1 (11.1) | 1 (8.3) | 2 (9.5) | 0 |
| 95% CI | 0.3, 48.3 | 0.2, 38.5 | 1.2, 30.4 | 0, 26.5 |
| Type 2, n (%) | 2 (22.2) | 3 (25.0) | 5 (23.8) | 0 |
| 95% CI | 2.8, 60.0 | 5.5, 57.2 | 8.2, 47.2 | — |

Figure 14:
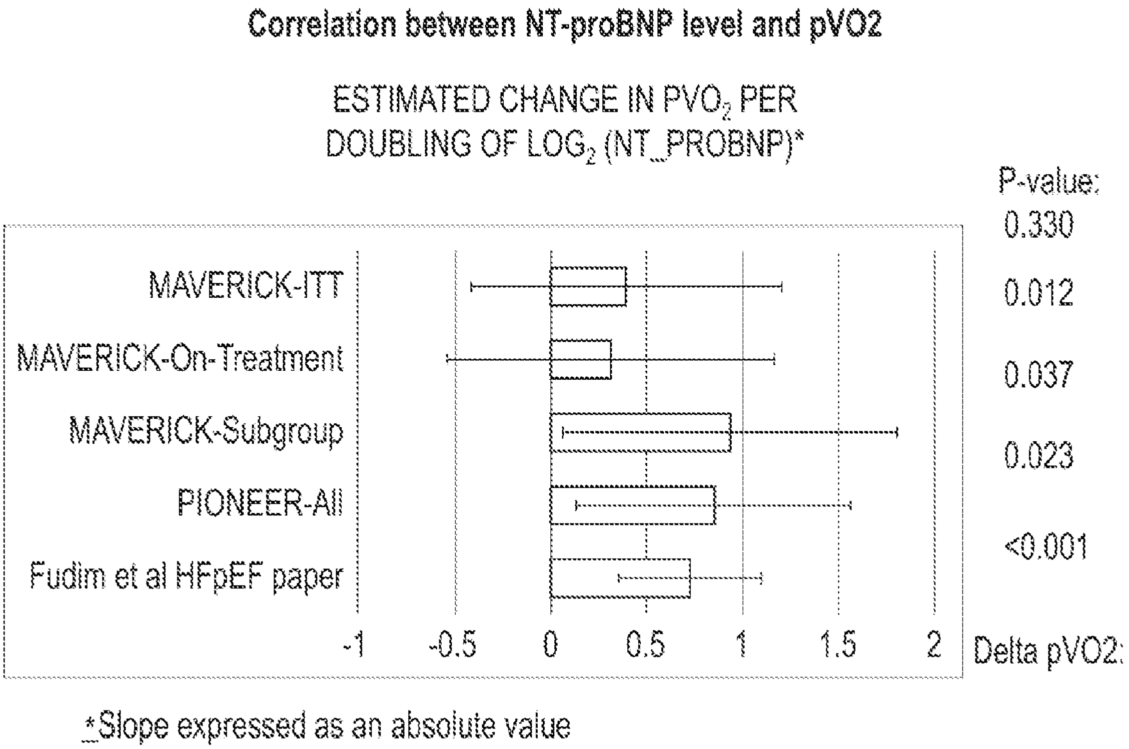
FIG. 14 is a bar chart showing the correlation between NT-proBNP level and $pVO_2$ in different studies and different treatment groups.

*Composite functional endpoint was ≥1.5 mL/kg/min increase in pVO2 and ≥1 NYHA Class improvement; or ≥3.0 mL/kg/min increase in pVO2 with no worsening in NYHA Class An inverse correlation was observed between NT-proBNP levels and pVO2, a marker of clinical benefit in a Maverick patient subgroup (i.e., elevated troponin and/or elevated E/e'). See FIG. 14.

Example 4. Overdosing of Mavacamten

Experiments with isolated adult rat ventricular myocytes in vitro and with anaesthetized rats in vivo have established that the pharmacologic effects of mavacamten can be counteracted by β adrenergic agonists (isoproterenol and dobutamine, respectively). Therefore, in the mavacamten clinical trials, if a subject experiences AEs potentially related to reduced cardiac output due to the administration of mavacamten, administration of therapeutic doses of a β adrenergic agonist (e.g., 5 to 10 μg/kg/min dobutamine infusion) should be considered. Additional supportive measures, e.g., intravenous volume supplementation and/or the use of arterial vasoconstrictor agents (a adrenergic agonists) may complement the use of a β adrenergic agonist.

Methods: The responsiveness of mavacamten-induced cardio-depression to positive inotropic challenges was assessed in a set of conscious Sprague-Dawley rats. In these animals, functional reserve was assessed via either dobutamine (+DOB, 10 ug/kg/min IV for 10 min, n=7) or levosimendan (+LEVO, 0.3 μmol/kg IV over 30; n=6) challenges given 3 hrs following a single-dose administration of MAVA (at 4 mg/kg, PO). Cardiac function/geometry were recorded and compared at three separate time-points/days: prior to dosing (i.e., at baseline) and at 3 hrs post-dosing both before as well as during the inotropic challenge; in order to account for the levosimendan-induced changes in loading conditions, an additional echocardiographic examination was performed following acute preload-restoration in LEVO-treated rats (+LEVO/F, 0.9% NaCl at 30 mL/kg/hr IV).

In these experiments, left-ventricular fractional shortening (FS), an index of systolic performance, as well as LV dimensions/volumes and heart rates were measured using a high-frequency transducer and parasternal long-axis transthoracic views (Vevo2100, VisualSonic). FS was defined as the end-diastole normalized change in internal dimensions/diameter of the left ventricle between end-systole (LVESd) and end-diastole (LVEDd) (i.e., FS=100·[LVEDd−LVESd]/LVEDd). LV volumes were derived assuming a Teichholz model (LVV=7·[2.4+LVid]−1·LVid3).

In addition, the effects of MAVA (at 1.5 mg/kg PO, via gavage) on cardiac reserve were evaluated via acute β-AR challenges (dobutamime: 2, 5, and 10 ug/kg/min IV) in conscious fully-instrumented (LVPV group) dogs with normal cardiac function (n=8). These challenges were performed before/after dosing (+3-hour) in control- and MAVA-treated animals both under normal cardiac physiological conditions (n=4) and under (mild) concomitant cardio-depression induced via either selective β-AR blockade (+BB, metoprolol 0.5±0.1 mg/kg PO tid; n=4) or L-type Ca2+-channel blockade (+CCB, verapamil at 5±1 mg/kg PO tid; n=4); pharmacological blockades were established for 7 days prior to the MAVA treatment. Both peak and dose-responses were evaluated at steady state.

Throughout these experiments, analog signals were digitally acquired (1000 Hz) and recorded continuously with a data acquisition/analysis system (IOX; EMKA Technologies). Heart rate (HR), end-systolic (ESP) and end-diastolic pressures (EDP), as well as the peak rates of pressure rise/decline (dP/dtmax and dP/dtmin), the contractility index (CI: dP/dt/P at dP/dtmax), and the time-constant of myocardial relaxation (tau1/2, time for 50% decay from dP/dtmin) were derived from the LV pressure signal. Meanwhile, the end-systolic (ESV) and end-diastolic volumes (EDV) were measured from the LV volume signal derived from the implanted myocardial crystals. LV volumes were derived assuming a Teichholz model, and stroke volume (SV=EDV−ESV), ejection fraction (EF=SV/EDV), as well as cardiac output (CO=SV·HR) were calculated; in a subset of animals, SV and CO values were verified from data derived from the implanted aortic flow problem. During each experiment, LV pressure-volume relationships were also evaluated during brief periods of cardiac preload reduction (transient occlusion of the inferior vena cava by inflation of the implanted cuff) using the telemetry-based LV pressure and the crystal-derived volume signals. The slopes of the preload-recruitable stroke work (PRSW; stroke work vs. EDV) and the end-systolic pressure-volume relationships (ESPVR; end-systolic elastance, Ees) were derived by software using linear models (IOX; EMKA Technologies), and were used as load-independent inotropic indices. Ventricular load was estimated by the effective arterial elastance (Ea=ESP/SV). In addition, the functional left-ventricular stiffness at end-diastole (LV-b) was estimated as the slope of the linear end-diastolic pressure-volume relationship (EDPVR), while the EDV/EDP ratio was used as an index of LV distensibility.

Both dobutamine (a synthetic β-AR agonist) and levosimendan (a phosphodiesterase-3 inhibitor) successfully rescued/restored echocardiography-derived indices of systolic function in healthy rats exposed to a supra-therapeutic dose of mavacamten (resulting an approximately a 50% reduction in ejection fraction). Similar observations were noted in conscious chronically-instrumented dogs. In dogs, dobutamine triggered comparable stroke-volume/cardiac output recruitments both before (i.e., control condition) and under acute mavacamten treatment, despite the induced depression; notably, MAVA blunted β-AR elevations in dP/dtmax and CI. Moreover, in these animals, mavacamten not only permitted systolic recruitment but also enhanced the β-AR induced acceleration of tau (and/or dP/dtmin, data not shown) at any given dP/dtmax gain, an observation consistent with the improvements in myocardial distensibility noted above.

Example 5. MYK-461-019 TRIAL: An Exploratory, Open-Label, Proof-of-Concept Study of Mavacamten (MYK-461) in Patients with Heart Failure with Preserved Ejection Fraction (HFpEF) and Chronic Elevation of Cardiac Troponin-I and/or NT-proBNP This study will be a multicenter, exploratory, open-label study of the administration of mavacamten in approximately 35-40 ambulatory participants with a diagnosis of (symptomatic) HFpEF and either elevated hs-cTnI or NT-proBNP (as defined in inclusion/exclusion criteria). The number of participants entering the study without elevated (>99th percentile) hs-cTnI will be limited to 23. Participants will receive a 26 week course of mavacamten followed by an 8 week washout period. All participants will initially receive 2.5 mg orally each day. At week 14, the dose for some participants may be increased to 5 mg orally each day as defined below in Study Treatment section.

Study Treatment:

Doses of mavacamten used in this study will be 2.5 and 5 mg. Dose adjustments at Week 14 will be based upon biomarkers (hs-cTnI and NT-proBNP) and left ventricular ejection fraction (LVEF) measured at the Week 12 visit.

For participants entering the study with hs-cTnI>99$^{th}$ percentile, the dose will be increased to 5 mg at Week 14 if the following conditions are met:

1. hs-cTnI (at Week 12) has not decreased by at least 30% relative to the mean of all available pre-treatment values (pre-screening, screening, and day 1 pre-dose) AND
2. Resting LVEF (at Week 12) has not decreased by ≥15% (relative reduction from the mean of all available screening and Day 1 Pre-Dose resting LVEFs) AND
3. NT-proBNP has not increased by >50% from the mean of all available screening and Day 1 pre-dose resting measurements If the core laboratory determines that a precise quantitative estimate of LVEF is not possible for the Week 12 echo due to technical factors, a repeat echo from an unscheduled visit (if performed by Week 14) can be utilized for this purpose. If this is not possible, a qualitative assessment of LVEF from the Week 12 TTE may be utilized.

For participants entering the study with NT-proBNP elevation and hs-cTnI≤99$^{th}$ percentile, the dose will be increased to 5 mg at Week 14 if the following conditions are met:

1. NT-proBNP (at Week 12) has not decreased by at least 50% or increased by at least 50% relative to the mean of all available pre-treatment values (pre-screening, screening, and day 1 pre-dose) AND
2. Resting LVEF (at Week 12) has not decreased by ≥15% (relative reduction from the mean of all available screening and Day 1 Pre-Dose resting LVEFs)

There will also be a provision for temporary or permanent treatment discontinuation based on the LVEF after all visits in which it is measured:

- If the local sonographer determines that the LVEF is ≤45%: under these circumstances, the sonographer should review and re-measure the findings with at least one other professional qualified in echocardiography assessment (can be the investigator) in addition to informing the investigator. If the result is confirmed locally (LVEF≤45%), then study drug will be permanently discontinued.
- If the central echo lab determines that LVEF has either decreased (relative reduction) of 20% from baseline (mean of all screening/pre-dose values) OR that the LVEF is <50% but >45%, study drug will be temporarily discontinued for two weeks. In the event that TTE quality is deemed insufficient by the central core laboratory to precisely estimate LVEF, an attempt to obtain a repeat unscheduled TTE for this purpose should be made; however, if this is not possible or if LVEF still cannot be quantitatively estimated, the core TTE laboratory should qualitatively determine whether the LVEF is likely <50% and this information will be utilized for dosing.
- If the local investigator is informed that LVEF is <50 on a non-study TTE, study drug should be temporarily discontinued and the TTE images obtained for core TTE lab review. If the core TTE lab determines that LVEF was ≤45% on the TTE, study drug must be permanently discontinued. If the core TTE lab determines that LVEF was <50% but >45%: the procedures in (2) above should be followed.

If study drug is temporarily discontinued under (2), it may be restarted after 2 weeks if repeat TTE demonstrates that participant no longer meets the criteria leading to temporary discontinuation on the subsequent TTE. The dose upon restarting will be 2.5 mg regardless of the dose at the time of temporary discontinuation. If a participant meets criteria for temporary discontinuation a second time after restarting study drug, the study drug will be permanently discontinued.

Study Objectives:

| | |
|---|---|
| Primary Objectives | To evaluate the effect of a 26-week course of mavacamten on hs-cTnI levels (at rest and post-exercise)<br>To evaluate the effect of a 26-week course of mavacamten on NT-proBNP levels (at rest and post-exercise)<br>To evaluate the safety and tolerability of a 26-week course of mavacamten in individuals with HFpEF with chronic elevation of cTn and/or NT-proBNP |
| Exploratory Objectives | To assess the effect of a 26-week course of mavacamten on Peak $VO_2$ and $VE/VCO_2$ slope by CPET<br>To assess the effect of a 26 week course of mavacamten on diastolic function (both with and without exercise) by TTE<br>To assess the effect of a 26-week course of mavacamten on systolic function (both with and without exercise) by TTE<br>To assess the effect of a 26-week course of mavacamten on activity measured by accelerometry<br>To assess the effect of a 26-week course of mavacamten on NYHA class<br>To evaluate the effect of a 26-week course of mavacamten on KCCQ<br>To evaluate the effect of a 26-week course of mavacamten on Seattle Angina Questionnaire |
| Pharmacokinetic Objective | To characterize the pharmacokinetics (PK) profile of mavacamten in individuals with HFpEF with chronic elevation of cTn and/or NT-proBNP |
| CMR Substudy Exploratory Objectives (Optional) | To evaluate the effect of a 26-week course of mavacamten on left ventricular mass index as measured by cardiac magnetic resonance (CMR) imaging<br>To evaluate the effect of a 26-week course of mavacamten on myocardial perfusion as measured by CMR |

Study Criteria

| | |
|---|---|
| Inclusion Criteria | Each participant must meet the following criteria to be included in this study:<br>1. Able to understand and comply with the study procedures, understand the risks involved in the study, and provide written informed consent according to federal, local, and institutional guidelines before the first study-specific procedure<br>2. Is at least 50 years old at Screening<br>3. Body weight is greater than 45 kg at Screening<br>4. Prior objective evidence of heart failure as shown by 1 or more of the following criteria:<br>Previous hospitalization for heart failure with radiographic evidence of pulmonary congestion<br>Elevated left ventricular end-diastolic pressure or pulmonary capillary wedge pressure at rest (≥15 mm Hg) or with exercise (≥25 mm Hg)<br>Elevated level of NT-proBNP (>400 pg/mL) or BNP (>200 pg/mL). In the absence of qualifying historical NT-proBNP or BNP levels meeting this threshold, screening NT-proBNP meeting the threshold in inclusion criterion 5 will satisfy inclusion criterion 4.<br>Echocardiographic evidence of medial E/e' ratio ≥15 or left atrial enlargement together with chronic treatment with a loop diuretic<br>5. Has either:<br>a screening hs-cTnI >$99^{th}$ percentile. OR<br>a screening NT-proBNP >300 pg/mL (if not in atrial fibrillation or atrial flutter) or >750 pg/mL (if in atrial fibrillation or atrial flutter)*<br>*No more than 23 participants may enter the study without a screening hs-cTnI >$99^{th}$ percentile<br>6. Has documented left ventricular ejection fraction ≥60% at the Screening visit as determined by the echocardiography central laboratory and no prior LVEF ≤45%. |

-continued

| | |
|---|---|
| | 7. Has documented elevated left ventricular mass index by 2-dimensional imaging (>95 g/$m^2$ if female and >115 g/$m^2$ if male). Upon agreement of the study Co-Coordinating Investigators and MyoKardia after an interim review of data, the LVMI threshold for inclusion may be increased if deemed appropriate.<br>8. Has adequate acoustic windows on screening resting transthoracic echocardiogram as determined by echocardiography central laboratory, to enable high likelihood of acquisition of high quality transthoracic echocardiograms throughout study.<br>9. Has New York Heart Association (NYHA) Class II or III symptoms at Screening<br>10. Has safety laboratory parameters (chemistry, hematology, coagulation, and urinalysis) within normal limits (according to the central laboratory reference range) at Screening; however, a participant with safety laboratory parameters outside normal limits may be included if he or she meets all of the following criteria:<br>The safety laboratory parameter outside normal limits is considered by the investigator to be clinically unimportant<br>If there is an alanine aminotransferase or aspartate aminotransferase result, the value must be <3× the upper limit of the laboratory reference range<br>The body size-adjusted estimated glomerular filtration rate is ≥45 mL/min/1.73 $m^2$<br>11. Female participants must not be pregnant or lactating and, if sexually active, must be using one of the following highly effective birth control methods from the Screening visit through 3 months after the last dose of study drug.<br>Combined (estrogen- and progestogen-containing) hormonal contraception associated with inhibition of ovulation or progestogen-only hormonal contraception associated with inhibition of ovulation by oral, implantable, or injectable route of administration<br>Intrauterine device (IUD)<br>Intrauterine hormone-releasing system (IUS)<br>Female is surgically sterile for 6 months or postmenopausal for 1 year. Permanent sterilization includes hysterectomy, bilateral oophorectomy, bilateral salpingectomy, and/or documented bilateral tubal occlusion at least 6 months prior to Screening. Females are considered postmenopausal if they have had amenorrhea for at least 1 year or more following cessation of all exogenous hormonal treatments and follicle-stimulating hormone levels are in the postmenopausal range<br>Male partners must also use a contraceptive (e.g., barrier, condom or vasectomy) |
| Exclusion Criteria | A participant who meets any of the following exclusion criteria may not participate in this study:<br>1. Previously participated in a clinical study with mavacamten<br>2. Hypersensitivity to any of the components of the mavacamten formulation<br>3. Participated in a clinical trial where the participant received any investigational drug (or is currently using an investigational device) within 30 days prior to screening or 5 times the respective elimination half-life (whichever is longer)<br>4. Has a known infiltrative or storage disorder causing HFpEF and/or cardiac hypertrophy, such as amyloidosis, Fabry disease, or Noonan syndrome with LV hypertrophy OR has imaging results from this study deemed on central review by the co-lead investigators to be suspicious for amyloid OR has an abnormal serum free light chain ratio at screening OR a positive serum immunofixation result<br>5. Has any medical condition that precludes upright exercise stress testing (for stress echocardiogram)<br>6. Has a history of syncope within the last 6 months or sustained ventricular tachycardia with exercise within the past 6 months<br>7. Has a history of resuscitated sudden cardiac arrest at any time or known appropriate implantable cardioverter defibrillator (ICD) discharge within 6 months prior to Screening<br>8. Has paroxysmal, intermittent atrial fibrillation with atrial fibrillation present per the investigator's evaluation of the participant's electrocardiogram (ECG) at the time of screening<br>9. Has persistent or permanent atrial fibrillation not on anticoagulation for at least 4 weeks prior to Screening and/or is not adequately rate controlled within 6 months prior to Screening (note: patients with persistent or permanent atrial fibrillation who are anticoagulated and adequately rate-controlled are allowed)<br>10. For participants on beta blocker, verapamil or diltiazem, any dose adjustment <14 days before screening |

-continued

| | |
|---|---|
| | 11. Currently treated or planned treatment during the study with a combination of beta blocker and verapamil or a combination of beta blocker and diltiazem<br>12. Fridericia-corrected QT interval (QTcF) >500 ms or any other ECG abnormality considered by the investigator to pose a risk to participant safety (eg, second-degree atrioventricular block type II)<br>13. Has known unrevascularized coronary artery disease<br>14. Has known moderate or severe (as per the Investigator's judgment) aortic valve stenosis at Screening<br>15. Has any acute or serious comorbid condition (eg, major infection or hematologic, renal, metabolic, gastrointestinal, or endocrine dysfunction) that, in the judgment of the investigator, could lead to premature termination of study participation or interfere with the measurement or interpretation of the efficacy and safety assessments in the study<br>16. Has severe chronic obstructive pulmonary disease (COPD), or other severe pulmonary disease, requiring home oxygen, chronic nebulizer therapy, chronic oral steroid therapy or hospitalized for pulmonary decompensation within 12 months<br>17. Hemoglobin <10 g/dL<br>18. Body Mass Index ≥45 $kg/m^2$<br>19. Positive serologic test at Screening for infection with human immunodeficiency virus, hepatitis C virus, or hepatitis B virus<br>20. Active acute respiratory infection at time of screening or randomization<br>21. History of clinically significant malignant disease within 10 years of Screening:<br>Participants who have been successfully treated for nonmetastatic cutaneous squamous cell or basal cell carcinoma or have been adequately treated for cervical carcinoma in situ can be included in the study<br>22. History or evidence of any other clinically significant disorder, condition, or disease (with the exception of those outlined above) that, in the opinion of the investigator or medical monitor, would pose a risk to participant safety or interfere with the study evaluation, procedures, or completion<br>23. Currently taking, or has taken within 14 days prior to Screening, a prohibited medication such as a cytochrome P450 (CYP) 2C19 inhibitor (eg, omeprazole, esomeprazole), a strong CYP 3A4 inhibitor, or St. Johns Wort<br>24. Prior treatment with cardiotoxic agents such as doxorubicin or similar<br>25. Unable to comply with the study requirements, including the number of required visits to the clinical site<br>26. Employed by, or a relative of someone employed by MyoKardia, the investigator, or his/her staff or family |
| Additional CMR Substudy Inclusion Criterion | 1. Consents to participation in MRI substudy |
| Additional CMR Substudy Exclusion Criterion | 1. Any contraindication to MRI (including contraindications to gadolinium contrast) based on local clinical protocols |

Study Endpoints:

| | |
|---|---|
| Primary Endpoints | Change from baseline to Week 26 in hs-cTnI |
| | Change from baseline to Week 26 in NT-proBNP |
| Exploratory Endpoints | Change from baseline to Week 26 in Peak $VO_2$ |
| | Change from baseline to Week 26 in $VE/VCO_2$ slope |
| | Change from baseline to Week 26 in TTE measures of resting diastolic function (e', E/e', E/A, pulmonary artery systolic pressure, left atrial size) |
| | Change from baseline to Week 26 in TTE measures of diastolic function upon exercise stress echo |
| | Change from baseline to Week 26 in TTE measures of systolic function (eg, LVEF) |
| | Change from baseline to Week 26 in TTE measures of systolic function upon exercise stress echo |
| | Change from baseline to Week 26 in average daily activity units as measured by accelerometry |
| | Change from baseline to Week 26 in NYHA Class |
| | Change from baseline to Week 26 in KCCQ Scores |
| | Change from baseline to Week 26 in Seattle Angina Questionnaire score |

-continued

| | |
|---|---|
| Exploratory Endpoints - CMR Sub-Study | Change from baseline to Week 26 in left ventricular mass index by CMR<br>Change from baseline to Week 26 in maximal left ventricular wall thickness by CMR<br>Change from baseline to Week 26 in perfusion by CMR |
| Safety Endpoints | Frequency and severity of treatment-emergent adverse events, adverse events of special interest (permanent or temporary treatment discontinuation due to LVEF reduction), and serious adverse events; laboratory abnormalities; vital signs; and cardiac rhythm abnormalities |
| Pharmacokinetic Endpoint | Mavacamten plasma concentration over time |

Example 6. VALOR TRIAL: A Randomized, Double-Blind, Placebo-Controlled Study to Evaluate Mavacamten in Adults with Symptomatic Obstructive Hypertrophic Cardiomyopathy Who are Eligible for Septal Reduction Therapy This is a Phase 3 study to evaluate the effect of mavacamten treatment on reducing the number of septal reduction therapy (SRT) procedures performed in subjects with symptomatic obstructive hypertrophic cardiomyopathy (oHCM [also known as HOCM]) who are eligible for SRT based on American College of Cardiology Foundation (ACCF)/American Heart Association (AHA) and/or European Society of Cardiology (ESC) guidelines (ie, guidelines). Data from this study will complement results from the completed MYK-461-004 (PIONEER-HCM) and ongoing MYK-461-005 (EXPLORER-HCM) studies of mavacamten in subjects with symptomatic oHCM and potentially expand the benefit of mavacamten to a population of oHCM patients with severe symptoms refractory to maximal medical therapy.

Study Objective and Endpoints:

The primary, secondary, exploratory, and pharmacokinetics (PK) objectives and endpoints of the study are as follows:

| Objectives | Endpoints |
|---|---|
| Primary | |
| To evaluate the ability of mavacamten to reduce the need for SRT in guideline-eligible subjects with oHCM who are referred for SRT. | The primary endpoint will be a composite of:<br>1) Decision to proceed with SRT prior to or at Week 16 and 2) SRT guideline eligible at Week 16 (but declined by subject). |
| Secondary | |
| To evaluate the persistence of the effects of mavacamten in reducing the number of SRT procedures. | The endpoint will be a composite of the outcomes at Week 32 compared with Week 16 for subjects in the mavacamten group in:<br>1) Decision to proceed with SRT prior to or at Week 32 and 2) SRT guideline eligible at Week 32 (but declined by subject). |
| To evaluate the effect of mavacamten on subject symptoms. | Change from baseline to Week 16 in the mavacamten group compared with the placebo group in:<br>New York Heart Association (NYHA) functional class<br>Kansas City Cardiomyopathy Questionnaire 23-item version (KCCQ-23). |
| To evaluate the effect of mavacamten on cardiac biomarkers | Change from baseline to Week 16 in the mavacamten group compared with the placebo group in N-terminal pro b-type natriuretic peptide (NT-proBNP) and cardiac troponin. |
| To evaluate the effect of mavacamten on a hemodynamic parameter | Change from baseline to Week16 in the mavacamten group compared with the placebo group in left ventricular outflow tract (LVOT) gradient. |
| Exploratory | |
| To evaluate the ability of mavacamten to reduce the need for SRT in subjects who were randomized to receive placebo for the first 16 weeks of the study. | The endpoint will be a composite of the outcomes at Week 32 compared with Week 16 for subjects in the placebo-to-active group on:<br>1) Decision to proceed with SRT prior to or at Week 32 and 2) SRT guideline eligible at Week 32, but declined by subject. |
| To evaluate the ability of mavacamten to reduce symptoms and hemodynamic gradient. | Analysis of NYHA functional class, KCCQ-23, and LVOT gradient will be performed for:<br>Change from baseline to Week 16 compared with change from baseline to Week 32 in the mavacamten group; Change from baseline to Week 32 in the mavacamten group compared with the placebo-to-active group. |

-continued

| Objectives | Endpoints |
|---|---|
| To evaluate the ability of mavacamten to reduce hemodynamic parameters and cardiac biomarkers and to improve subject activity level and quality of life. | Analysis of left ventricular ejection fraction (LVEF), left ventricular (LV) filling pressures, left atrium size, cardiac biomarkers, accelerometry, and EuroQol 5-dimensions 5-level questionnaire will be performed for:<br>Change from baseline to Week 16 in the mavacamten group compared with the placebo group;<br>Change from baseline to Week 16 compared with change from baseline to Week 32 in the mavacamten group;<br>Change from baseline to Week 32 in the mavacamten group compared with the placebo-to-active group. |
| Evaluate the effects of mavacamten on type and dose of cardiac medications. | Change from baseline to Week 16, Week 16 to 32, and Week 32 to Week 128 in HCM standard of care cardiac medications. |
| Safety | |
| To evaluate the safety of mavacamten for the duration of the study. | Incidence of LVEF <50% following dose titration determined by transthoracic echocardiography (TTE)<br>Incidence and severity of treatment-emergent adverse events (TEAEs), treatment-emergent serious adverse events (SAEs), and laboratory abnormalities (including trends in NT-proBNP);<br>Incidence of SAEs in subjects taking mavacamten compared with subjects taking placebo and with those who undergo SRT;<br>Incidence of major adverse cardiac events (MACE; death, stroke, acute myocardial infarction);<br>Incidence of hospitalizations (due to cardiovascular [CV] and non-CV events);<br>Incidence of heart failure (HF) events, (including hospitalizations and urgent emergency room/outpatient visits for HF and escalation in HF treatment);<br>Incidence of atrial fibrillation/flutter (new from screening and recurrent);<br>Incidence of implantable cardioverter-defibrillator (ICD) therapy and resuscitated cardiac arrest<br>Incidence of ventricular tachyarrhythmias (includes ventricular tachycardia, ventricular fibrillation, and Torsades de Pointe);<br>Incidence of adverse events of special interest (AESIs; symptomatic overdose, pregnancy, LVEF ≤30%). |
| Pharmacokinetics | |
| Evaluate plasma concentrations of mavacamten | Summarize mavacamten plasma concentrations from on-treatment sample collection |

Overall Design:

This is a Phase 3, randomized, double-blind, placebo-controlled, multicenter study of males and females≥18 years with oHCM who meet ACCF/AHA and/or ESC guideline criteria for SRT (e.g., LVOT gradient of ≥50 mmHg and NYHA Class III-IV) and have been referred for an invasive procedure. After completing screening assessments, eligible subjects will be randomized 1:1 to the mavacamten or placebo treatment groups. Randomization will be stratified by the type of SRT procedure recommended (myectomy or alcohol septal ablation [ASA]) and NYHA functional class.

The study duration will be up to 138 weeks, including a 2-week screening period (Week −2), 128 weeks of treatment, and an 8-week posttreatment follow-up visit (Week 136).

There will be 3 dosing periods as follows:

- Placebo-controlled dosing period (Day 1 to Week 16): Subjects will receive double-blind mavacamten or placebo once daily for 16 weeks.
- Active-controlled dosing period (Week 16 to Week 32): All subjects will receive mavacamten once daily for 16 weeks. Dose will be blinded.
- Long-term extension (LTE) dosing period (Week 32 to Week 128): All subjects will receive mavacamten once daily for 96 weeks. Dose will remain blinded unless the sponsor chooses to unblind once the primary analysis is complete.

Study Procedures and Treatment:

- Study visits will occur at screening, Day 1, every 4 weeks through Week 32, every 12 weeks thereafter until Week 128 (EOT), and Week 136 (end of study). Visits must take place at the study center at Day 1 and Weeks 8, 16, 24, and 32, every 12 weeks thereafter through Week 128, and Week 136. For selected sites, study visits may take place at a subject's home with a qualified home health care professional who is contracted by the sponsor at Weeks 4, 12, 20, and 28. Subjects who prematurely discontinue study drug at any time (except for SRT) will attend a treatment discontinuation visit within 14 days of study drug discontinuation and will be followed every 24 weeks thereafter until Week 128.
- On Day 1, eligible subjects will be randomized in a double-blind manner via an interactive response system (IXRS) to the mavacamten or placebo groups. Randomization will be stratified by the type of SRT procedure recommended (myectomy or ASA) and NYHA functional class. Subjects will begin mavacamten 5 mg or matching placebo once daily by mouth for 16 weeks with subsequent assessments for dose adjustments.

At Weeks 16, 32, 80, and 128, subjects will be reevaluated for SRT eligibility. The investigator will confirm that the subject remains on maximal medical therapy, determine NYHA class, and enter the information in the electronic case report form (eCRF). Every effort should be made to have the same investigator who evaluates NYHA at screening also evaluate NYHA at Weeks 16, 32, 80, and 128. Independently, and blinded to the investigator, a TTE will be performed to assess LVOT gradients at rest, provocation, and post exercise. At Weeks 16 and 32, TTE will be read at the core echocardiography laboratory, and a categorical LVOT gradient result (<50 mmHg or ≥50 mmHg) will be reported to the study site by the core laboratory. At Weeks 80 and 128, LVOT<50 mmHg or ≥50 mmHg will be determined by site-read echocardiography. The investigator will remain blinded to the LVOT gradient result until after NYHA results have been entered in the eCRF. Results of medical therapy, NYHA functional class, and LVOT will be reviewed by the investigator, who will determine whether the subject meets ACCF/AHA and/or ESC eligibility criteria for SRT (yes or no). The investigator will discuss the recommendation with the subject. If the recommendation is to proceed with SRT, the subject may schedule the SRT at a recommended HCM center to occur after a recommended study drug washout period≥6 weeks, or the subject may decline the recommendation and remain on study drug.

After Week 16 assessments, subjects in the mavacamten treatment group who elect to continue treatment (i.e., do not make a decision to have SRT) will continue once-daily dosing with mavacamten at the dose they had been receiving at Week 16 for an additional 16 weeks; subjects in the placebo group who elect to continue treatment (i.e., do not make a decision to have SRT) will begin dosing with mavacamten 5 mg once daily for 16 weeks with subsequent assessments for dose adjustments (placebo-to-active group). During the active-controlled dosing period, mavacamten dose will remain blinded.

After Week 32 assessments, all subjects (mavacamten group and placebo-to-active group) who elect to continue treatment (ie, do not make a decision to have SRT) will continue daily dosing with mavacamten at the dose they had been receiving at Week 32 for an additional 96 weeks to Week 128 (EOT). During the LTE dosing period, mavacamten dose will remain blinded unless the sponsor chooses to unblind once the primary analysis is complete. Subjects will be reevaluated for SRT eligibility at Weeks 80 and 128.

During the study, dose may be titrated based on LVEF and LVOT by TTE read at the core echocardiography laboratory and according to dose titration guidelines. Throughout the study, all dose adjustments will occur in a blinded manner via the IXRS.

During the placebo-controlled dosing period (Day 1 to Week 16), all subjects will be evaluated for possible down-titration at Week 4 and up-titration at Weeks 8 and 12. Although subjects in the placebo group will be evaluated for dose titration, they will remain on placebo.

During the active-controlled dosing period (Weeks 16 to 32), subjects in the placebo-to-active group, who begin dosing with mavacamten at Week 16, will be evaluated for possible down-titration at Week 20 and up-titration at Weeks 24 and 28.

During the LTE dosing period (Weeks 32 to 128), mavacamten dose may be up-titrated at any scheduled visit after Week 32 if the site-read LVOT gradient with Valsalva maneuver is ≥30 mmHg and LVEF is ≥50. All dose increases during LTE dosing must be approved by the medical monitor before they are implemented. Subjects who have their mavacamten dose increased during the LTE period will attend an unscheduled study visit 4 weeks after the dose increase and then resume the regular study visit schedule.

Dose may be down-titrated for safety at any time. Safety will be monitored throughout the study.

Table 6.0 provides dose titration guidelines for the study

TABLE 6.0

Dose Titration Guidelines

| | LVEF ≥ 50% | | | | | |
|---|---|---|---|---|---|---|
| | Mavacamten Group Day 1 to Week 16 Study Week | | | Placebo-to-Active Group Week 16 to Week 32 Study Week | | |
| | 4 | 8 | 12 | 20 | 24 | 28 |
| Valsalva LVOT ≥30 mmHg | Remain on 5 mg | Increase dose (2.5 mg to 5 mg, or 5 mg to 10 mg) | Increase dose (2.5 mg to 5 mg, 5 mg to 10 mg, or 10 mg to 15 mg) | Remain on 5 mg | Increase dose (2.5 mg to 5 mg, or 5 mg to 10 mg) | Increase dose (2.5 mg to 5 mg, 5 mg to 10 mg, or 10 mg to 15 mg) |
| Valsalva LVOT <30 mmHg | Decrease dose (5 mg to 2.5 mg) | Dose remains unchanged | Dose remains unchanged | Decrease dose (5 mg to 2.5 mg) | Dose remains unchanged | Dose remains unchanged |
| LVOT not applicable | LVEF <50%<br>If at any time LVEF <50%, discontinue mavacamten 2-4 weeks until follow-up visit. If at follow-up, LVEF ≥50%, then resume at 1 step decreased dose (15 mg to 10 mg, 10 mg to 5 mg, or 5 mg to 2.5 mg, 2.5 mg to a retrial of 2.5 mg)<br>If LVEF again falls to <50%, then mavacamten will be permanently discontinued<br>If at any time LVEF ≤30%, permanently discontinue mavacamten. | | | | | |

Figure 15:
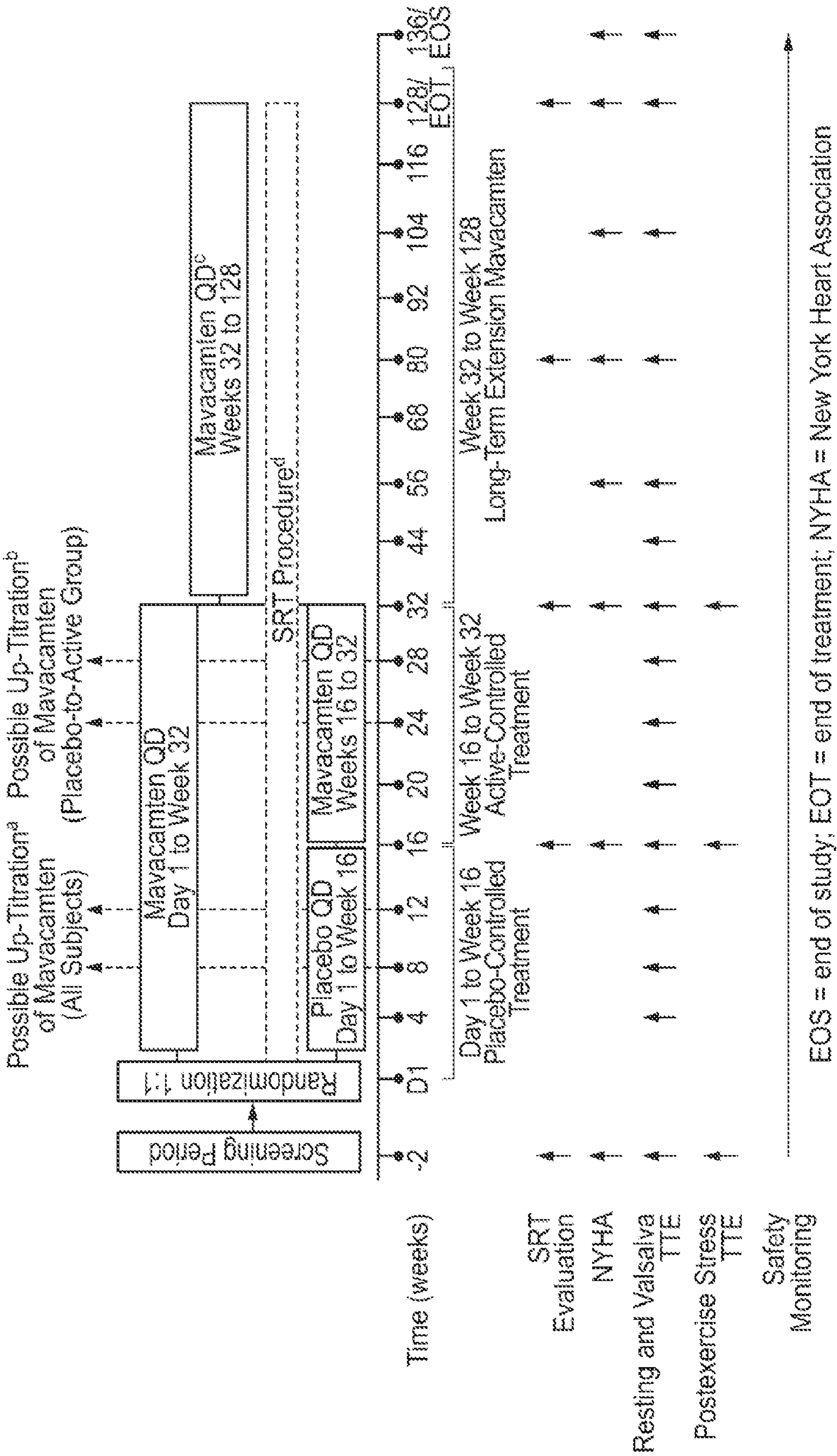
FIG. 15 is a scheme for the study of Example 6.

Study Scheme:

The study scheme is shown in FIG. 15.

Study Scheme Notes:

a During the placebo-controlled dosing period (Day 1 to Week 16) subjects will be evaluated for possible down-titration at Week 4 and up-titration at Weeks 8 and 12 by independent assessment of TTE by the echocardiography core laboratory and according to dose-titration guidelines. Dose may be down-titrated for safety at any time.

b Subjects in the placebo-to-active group, who begin dosing with mavacamten at Week 16, will be evaluated for possible down-titration at Week 20 and up-titration at Weeks 24 and 28. Dose may be down-titrated for safety at any time.

c During the long-term extension (LTE) dosing period (Weeks 32 to 128), mavacamten dose may be up-titrated at any scheduled visit after Week 32 if the site-read LVOT gradient with Valsalva maneuver is ≥30 mmHg and LVEF is ≥50%. All dose increases during LTE dosing must be approved by the MyoKardia medical monitor before they are implemented. Subjects who have their mavacamten dose increased during the LTE period will attend an unscheduled study visit 4 weeks after the dose increase and then resume the regular study visit schedule. Dose may be down-titrated for safety at any time.

d At any time during the study, subjects may withdraw from study drug and proceed with SRT at a recognized HCM center after a recommended study drug washout period≥6 weeks. Subjects who discontinue study drug to undergo SRT will undergo EOT assessments within 14 days and will have a telephone follow-up with the study site to assess adverse events 8 weeks after treatment discontinuation (or prior to SRT, whichever is earlier). Subjects will be followed every 24 weeks from the date of SRT to Week 128.

Study Drug Schedule:

On Day 1, subjects will begin blinded dosing with mavacamten or matching placebo once daily for 16 weeks (placebo-controlled period). After the Week 16 study assessments, subjects in the mavacamten group will continue mavacamten, and subjects in the placebo group will begin dosing with mavacamten, once daily from Weeks 16 to 32 (active-controlled period). During the active-controlled period, mavacamten dose will be blinded. Beginning at Week 16 and throughout the remainder of the study, the placebo group will be referred to as the placebo-to-active group. After the Week 32 assessments, all subjects will continue once-daily mavacamten until Week 128 (LTE period). During the LTE period, mavacamten dose will remain blinded unless the sponsor chooses to unblind once the primary analysis is complete.

Criteria for Evaluation:

Efficacy: The primary endpoint will be a composite of 1) the number of subjects who decide to proceed with SRT prior to or at Week 16 and 2) the number of subjects who are SRT guideline eligible at Week 16 but decline in the mavacamten group compared with the placebo group.

Safety: Safety assessments include monitoring of AEs and concomitant medications, safety laboratory assessments, physical examinations, vital sign measurements, TTEs, cardiac/activity monitoring, and ECGs.

SRT Evaluation:

At screening, the investigator will confirm the subject's NYHA functional class and eligibility for SRT based on the ACCF/AHA and/or ESC guidelines. At any time during the study, subjects may withdraw from study drug and proceed with SRT at a recognized HCM center after a recommended study drug washout period≥6 weeks. Subjects who discontinue study drug to undergo SRT will undergo end-of-treatment (EOT) assessments within 14 days and will have a telephone follow-up with the study site to assess adverse events (AEs) 8 weeks after treatment discontinuation (or prior to SRT, whichever is earlier). Subjects will be followed every 24 weeks from the date of SRT to Week 128.

At Weeks 16, 32, 80, and 128, subjects will be reevaluated for SRT eligibility by maximal medical therapy, NYHA functional class, and TTE. Every effort should be made to have the same investigator who evaluates NYHA at screening also evaluate NYHA at Weeks 16, 32, 80, and 128. At Weeks 16 and 32, LVOT<50 mmHg or ≥50 mmHg will be revealed to the site by the core echocardiography laboratory after the investigator makes the NYHA determination. The investigator will make a guideline-based recommendation for SRT (yes or no). Subjects will be required to decide within 48 hours whether to accept the recommendation for SRT or continue study treatment. At Weeks 80 and 128, LVOT<50 mmHg or ≥50 mmHg will be determined by site-read echocardiography.

An interim analysis will be conducted after 50 subjects have completed the Week 16 study visit to assess efficacy results.

Inclusion Criteria:

(A) Able to understand and comply with the study procedures, understand the risks involved in the study, and provide written informed consent according to federal, local, and institutional guidelines prior to initiation of any study-specific procedure.

(B) At least 18 years old at screening.

(C) Body weight>45 kg at screening.

(D) Adequate acoustic windows to enable accurate TTE (refer to the central echocardiography laboratory's manual of operations).

(E) Diagnosed with oHCM (maximal septal thickness ≥15 mm or ≥13 mm with family history of HCM) consistent with current ACCF/AHA 2011 and/or ESC 2014 guidelines and meet their recommendations for invasive therapies as follows:

a. Clinical criteria: Despite maximally tolerated drug therapy severe dyspnea or chest pain (NYHA Class III or IV) or Class II with exertional symptoms, such as exertion-induced syncope or near syncope, b. Hemodynamic criteria: dynamic LVOT gradient at rest or with provocation (ie, Valsalva or exercise)≥50 mmHg associated with septal hypertrophy (read by the core echocardiography laboratory), and c. Anatomic criteria: targeted anterior septal thickness sufficient to perform the procedure safely and effectively in the judgment of the individual operator.

(F) Referred or under active consideration within the past 12 months for SRT procedure and willing to have SRT procedure.

(G) Subjects referred or considered for ASA must have adequate coronary artery anatomy for the operator to perform the procedure.

(H) Documented oxygen saturation at rest ≥90% at screening.

(I) Documented LVEF≥60% at screening according to core echocardiography laboratory reading.

(J) Female subjects not pregnant or lactating.

Exclusion Criteria:

1. Previously participated in a clinical study with mavacamten (individuals who failed screening for a prior mavacamten study may participate).
2. Hypersensitivity to any of the components of the mavacamten formulation.
3. Participated in a clinical trial in which the subject received any investigational drug (or currently using an investigational device) within 30 days prior to screening, or at least 5 times the respective elimination half-life (whichever is longer).
4. Known infiltrative or storage disorder causing cardiac hypertrophy that mimics oHCM, such as Fabry disease, amyloidosis, or Noonan syndrome with LV hypertrophy.
5. Planned invasive procedure during the first 32 weeks of the study.
6. Papillary muscle or mitral valve in need of repair or any other intracardiac procedure planned (however, if need for mitral valve repair is discovered during SRT procedure, the subject will continue to be followed on study).
7. For individuals on beta blockers, calcium channel blockers, or disopyramide, any dose adjustment of these medications<14 days prior to screening or an anticipated change in regimen during the first 16 weeks of the study.
8. Any medical condition that precludes upright exercise stress testing.
9. Paroxysmal, intermittent atrial fibrillation with atrial fibrillation present at screening per the investigator's evaluation of the subject's electrocardiogram (ECG).
10. Persistent or permanent atrial fibrillation and subject not on anticoagulation for ≥4 weeks prior to screening and/or not adequately rate controlled ≤6 months prior to screening.
11. Previously treated with invasive septal reduction (surgical myectomy or percutaneous ASA).
12. Planned implantable ICD placement or pulse generator change during the first 32 weeks of the study.
13. QT interval with Fridericia correction (QTcF)>500 ms when QRS interval <120 ms or QTcF>520 ms when QRS≥120 ms if subject has left bundle branch block.
14. Acute or serious comorbid condition (e.g. major infection or hematologic, renal, metabolic, gastrointestinal, or endocrine dysfunction) that, in the judgment of the investigator, could lead to premature termination of study participation or interfere with the measurement or interpretation of the efficacy and safety assessments in the study
    1. Pulmonary disease that limits exercise capacity or systemic arterial oxygen saturation
    2. History of malignant disease within 10 years prior to screening:
        1. Subjects who have been successfully treated for nonmetastatic cutaneous squamous cell or basal cell carcinoma or have been adequately treated for cervical carcinoma in situ or breast ductal carcinoma in situ may be included in the study
        2. Subjects with other malignancies who are cancer-free for more than 10 years prior to screening may be included in the study
15. History or evidence of any other clinically significant disorder, condition, or disease that, in the opinion of the investigator, would pose a risk to subject safety or interfere with study evaluations, procedures, or completion.
16. Safety laboratory parameters (chemistry, hematology, coagulation, and urinalysis) outside normal limits (according to the central laboratory reference range) at screening as assessed by the central laboratory; however, a subject with safety laboratory parameters outside the normal limits may be included if all the following criteria are met:
    a. Safety laboratory parameters outside normal limits are considered by the investigator to be clinically not significant
    b. If an alanine aminotransferase or aspartate aminotransferase result, the value must be <3×the upper limit of the laboratory reference range
    c. Body size-adjusted estimated glomerular filtration rate is ≥30 mL/min/1.73 m2.
17. Positive serologic test at screening for infection with human immunodeficiency virus; hepatitis C virus; or hepatitis B virus, with the exception of hepatitis B s-antibody positive, which is a marker of immunity.
18. Prior treatment with cardiotoxic agents, such as doxorubicin or similar.
19. Unable to comply with the study requirements, including the number of required visits to the study site.

Schedule of Study Assessments

TABLE 6.1

Schedule of Study Assessments (Screening through Week 32)

| | Screen | Placebo-Controlled Dosing Day 1 to Week 16 | | | | | Active-Controlled Dosing Weeks 16 to 32 | | | |
|---|---|---|---|---|---|---|---|---|---|---|
| Assessment[a, b] | Days −14 to −1 | Day 1 | Week 4 (+7 d) | Week 8 (+7 d) | Week 12 (+7 d) | Week 16 (+7 d) | Week 20 (+7 d) | Week 24 (+7 d) | Week 28 (+7 d) | Week 32 (+7 d) |
| Informed consent | X | | | | | | | | | |
| Medical, surgical and HCM history | X | | | | | | | | | |
| Randomization | | X | | | | | | | | |
| Vital signs[c] | X | X | X | X | X | X | X | X | X | X |
| Body weight | X | | | | | X | | | | X |
| NYHA functional class[d] | X | | | | | X | | | | X |

TABLE 6.1-continued

Schedule of Study Assessments (Screening through Week 32)

| | Screen | Placebo-Controlled Dosing Day 1 to Week 16 | | | | | Active-Controlled Dosing Weeks 16 to 32 | | | |
|---|---|---|---|---|---|---|---|---|---|---|
| Assessment[a, b] | Days −14 to −1 | Day 1 | Week 4 (+7 d) | Week 8 (+7 d) | Week 12 (+7 d) | Week 16 (+7 d) | Week 20 (+7 d) | Week 24 (+7 d) | Week 28 (+7 d) | Week 32 (+7 d) |
| AEs | X | X | X | X | X | X | X | X | X | X |
| Concomitant medications | X | X | X | X | X | X | X | X | X | X |
| Physical examination[e] | X | | | X | | X | | X | | X |
| KCCQ, EQ-5D-5L[f] | X | | | | | X | | | | X |
| Resting and Valsalva TTE | X | | X | X | X | X | X | X | X | X |
| Postexercise stress TTE[g] | X | | | | | X | | | | X |
| Single 12-lead ECG[h] | X | | X | X | X | X | X | X | X | X |
| Holter monitor application [i] | X | | | | X | | | | X | |
| Accelerometer provided[j] | X | | | | X | | | | X | |
| ICD download | X[k] | | | | | X | | | | X |
| PK sample | | | X | X | X | X | X | X | X | X |
| Hepatitis/ HIV panel | X | | | | | | | | | |
| Optional HCM genotyping [l] | X | | | | | | | | | |
| Optional pharmacogenetics[m] | X | | | | | | | | | |
| Blood chemistry and coagulation | X | | | X | | X | | X | | X |
| Hematology | X | | | | | X | | | | X |
| Cardiac biomarkers [n] | X | | | X | | X | | X | | X |
| Exploratory biomarkers | X | | | X | | X | | | | X |
| Serum pregnancy test or FSH[o] | X | | | | | | | | | |
| Urinalysis | X | | | | | X | | | | X |
| Pregnancy test urine (β-hCG)[p] | | X | X | X | X | X | X | X | X | X |
| Study drug dispensed[q] | | X | X | X | X | X | X | X | X | X |
| Once-daily study drug | | X | X | X | X | X | X | X | X | X |
| Dose adjustment based on TTE | | | X | X | X | | X | X | X | |
| SRT evaluation[r] | X | | | | | X | | | | X |
| Study drug compliance | | | X | X | X | X | X | X | X | X |

AE = adverse event;
β-hCG = beta human chorionic gonadotropin;
ECG = electrocardiogram;
EQ-5D-5L = EuroQol 5-dimension 5-level questionnaire;
FSH = follicle-stimulating hormone;
FU = follow-up;
HCM = hypertrophic cardiomyopathy;
HIV = human immunodeficiency virus;
ICD = implantable cardioverter-defibrillator;
KCCQ-23 = Kansas City Cardiomyopathy Questionnaire (23-item version);
NYHA = New York Heart Association;
PK = pharmacokinetics;

TABLE 6.1-continued

Schedule of Study Assessments (Screening through Week 32)

| | Screen | Placebo-Controlled Dosing Day 1 to Week 16 | | | | | Active-Controlled Dosing Weeks 16 to 32 | | | |
|---|---|---|---|---|---|---|---|---|---|---|
| Assessment[a, b] | Days −14 to −1 | Day 1 | Week 4 (+7 d) | Week 8 (+7 d) | Week 12 (+7 d) | Week 16 (+7 d) | Week 20 (+7 d) | Week 24 (+7 d) | Week 28 (+7 d) | Week 32 (+7 d) |

SRT = septal reduction therapy;

TTE = transthoracic echocardiogram

[a]Beginning at Week 4, each study visit has a window of +7 days. Regardless of the day within a window that the study visit occurs, the next visit should adhere to the visit schedule based on the Day 1 visit date. Study visits may occur over multiple days.

[b]On study visit days, study drug dosing should be delayed until after study assessments are complete and the study staff instruct the subject to take their daily dose.

[c]Vital signs, including temperature, heart rate (HR), respiratory rate (RR), and blood pressure (BP), will be obtained at screening, Day 1, Week 16, and Week 32 visits. At all other visits, vital signs will include only HR, RR, and BP.

[d]Every effort should be made to have the same investigator evaluate NYHA functional class at screening, Week 16, and Week 32.

[e]At screening, a complete physical examination will be performed, including a neurological examination (gross motor and deep tendon reflexes), height and weight, and assessment of the following: general appearance, skin, head and neck, mouth, lymph nodes, thyroid, abdomen, musculoskeletal, cardiovascular, neurological, and respiratory systems. At all other onsite visits, an abbreviated cardiopulmonary physical examination will be conducted.

[f]At study visits that KCCQ-23 and EQ-5D-5L assessments are collected, they should be completed prior to any other procedure.

[g]Subjects should abstain from food for ≥4 hours prior to postexercise stress TTEs at screening, Week 16, and Week 32.

[h]Single 12-lead ECGs will be performed prior to dosing and after 10 minutes of rest at screening and all study visits from Week 4 to Week 32. Each time an ECG is completed, a 10-second paper ECG will be obtained and maintained in the subject's source documentation.

[i] A Holter monitor will be applied at screening, Week 12, and Week 28 visits and retrieved at the Day 1, Week 16, and Week 32 visits, respectively. If a subject has an adverse reaction to the adhesive used for the Holter monitor, the requirement for monitoring may be waived.

[j]A wrist-worn accelerometer will be applied at screening, Week 12, and Week 28 visits and retrieved at the Day 1, Week 16, and Week 32 visits, respectively.

[k]ICD download may be performed at screening or prior to dosing on Day 1.

[l] A separate, optional consent form is required for HCM genotyping. If a subject has already been genotyped for HCM, they may consent to provide their results, which will be captured in the electronic case report form.

[m]A separate, optional consent form is required for collection of a blood sample for possible pharmacogenetics analysis.

[n] Blood samples for NT-proBNP and cardiac troponin will be collected prior to the postexercise stress TTE at screening, Week 16, and Week 32.

[o]FSH testing at screening is for postmenopausal female subjects to confirm postmenopausal status.

[p]Only females of child-bearing potential will be assessed for pregnancy. If a positive result occurs at any time, a serum pregnancy test should be performed.

[q]Study drug dispensing may occur up to 7 days after TTE assessments for dose titration.

[r]Evaluation for SRT may include a cardiopulmonary exercise test (CPET) if CPET is used as standard of care for SRT evaluation by the study site, but it is not required.

TABLE 6.2

Schedule of Study Assessments (Week 44 through Week 136)

| | LTE Dosing (Week 32 through 128) | | | | | | | | | |
|---|---|---|---|---|---|---|---|---|---|---|
| Assessment[a, b] | Week 44 (+7 d) | Week 56 (+7 d) | Week 68 (+7 d) | Week 80 (+7 d) | Week 92 (+7 d) | Week 104 (+7 d) | Week 116 (+7 d) | Week 128/EOT[c, d] (+7 d) | Week 136/EOS (+7 d) | UV [e] |
| Vital signs[f] | X | X | X | X | X | X | X | X | X | X |
| Body weight | | X | | X | | X | | X | X | X |
| NYHA functional class[g] | | X | | X | | X | | X | X | X |
| AEs | X | X | X | X | X | X | X | X | X | X |
| Concomitant medications | X | X | X | X | X | X | X | X | X | X |
| Physical examination [h] | X | | X | | X | | X | X | X | X |
| KCCQ, EQ-5D-5L[i] | | X | | X | | X | | X | X | |
| Resting and Valsalva TTE | X | X | | X | | X | | X | X | X |
| Postexercise stress TTE· [j] | | | | X | | | | X | | |
| Single 12-lead ECG[k] | X | X | | X | | X | | X | X | X |
| ICD download | | X | | X | | X | | X | | X |
| PK sample | X | X | | X | | X | | X | X | X |
| Blood chemistry and coagulation | X | X | | X | | X | | X | X | X |
| Hematology | | X | | X | | X | | X | X | X |
| Cardiac biomarkers | X | X | | X | | X | | X | X | X |
| Exploratory biomarkers | | X | | X | | X | | X | | |

TABLE 6.2-continued

Schedule of Study Assessments (Week 44 through Week 136)

| Assessment[a, b] | LTE Dosing (Week 32 through 128) Week 44 (+7 d) | Week 56 (+7 d) | Week 68 (+7 d) | Week 80 (+7 d) | Week 92 (+7 d) | Week 104 (+7 d) | Week 116 (+7 d) | Week 128/EOT[c, d] (+7 d) | Week 136/EOS (+7 d) | UV [e] |
|---|---|---|---|---|---|---|---|---|---|---|
| Urinalysis | | X | | X | | X | | X | | X |
| Pregnancy test urine (β-hCG)[l] | X | X | X | X | X | X | X | X | X | X |
| Study drug dispensed | X | X | X | X | X | X | X | | | X[m] |
| Once-daily study drug | | X | X | X | X | X | X | X | | |
| Dose adjustment based on site read TTE[n] | X | X | X | X | X | X | X | | | |
| SRT evaluation[o] | | | | X | | | | X | | |
| Study drug compliance | X | X | X | X | X | X | X | X | | X |

AE = adverse event;

β-hCG = beta human chorionic gonadotropin;

d = day;

ECG = electrocardiogram;

EOS = end of study;

EOT = end of treatment;

ICD = implantable cardioverter-defibrillator;

NYHA = New York Heart Association;

PK = pharmacokinetics;

TTE = transthoracic echocardiogram;

UV = unscheduled visit

[a]Beginning at Week 4, each study visit has a window of +7 days. Regardless of the day within a window that the study visit occurs, the next visit should adhere to the visit schedule based on the Day 1 visit date. Study visits may occur over multiple days.

[b]On study visit days, study drug dosing should be delayed until after study assessments are complete and the study staff instruct the subject to take their daily dose.

[c]Subjects who permanently discontinue study drug prior to Week 128 and are unwilling to remain on study to be evaluated for concomitant medications and clinical assessments will undergo EOT assessments within 14 days of study drug discontinuation and EOS assessments 8 weeks later.

[d]If a subject prematurely discontinues from the study (eg, withdrawal of consent), the medical monitor should be contacted, and EOT assessments should be conducted.

[e] Unscheduled visits may be conducted for assessment of AEs, new or worsening symptoms, physical examinations, vital signs, laboratory tests, ECGs, and TTEs and upon discontinuation of study drug prior to an SRT procedure. All information collected from unscheduled visits will be recorded in the eCRF and included in the clinical database.

[f]Blood pressure, heart rate, and respiratory rate will be assessed.

[g]Every effort should be made to have the same investigator who evaluated NYHA functional class at screening, Week 16, and Week 32 also evaluate NYHA functional class at Week 80 and Week 128.

[h]An abbreviated cardiopulmonary physical examination will be conducted.

[i]At study visits that KCCQ-23 and EQ-5D-5L assessments are collected, they should be completed prior to any other procedure.

[j]Subjects should abstain from food for ≥4 hours prior to postexercise stress TTEs.

[k]Single 12-lead ECGs will be performed prior to dosing and after 10 minutes of rest from Week 44 to Week 56, Weeks 80, 104, 128, and 136, and unscheduled visits, as applicable. Each time an ECG is completed, a 10-second paper ECG will be obtained and maintained in the subject's source documentation.

[l]Only females of child-bearing potential will be assessed for pregnancy. If a positive result occurs at any time, a serum pregnancy test should be performed.

[m]Study drug may be dispensed if unscheduled visit is to follow-up on a temporary discontinuation, and study drug is reintroduced.

[n]Mavacamten dose may be up-titrated at any scheduled visit after Week 32 if the site-read LVOT gradient with Valsalva maneuver is ≥30 mmHg and LVEF is ≥50%. All dose increases during LTE dosing must be approved by the MyoKardia medical monitor before they are implemented. Subjects who have their mavacamten dose increased during the LTE period will attend an unscheduled study visit 4 weeks after the dose increase and then resume the regular study visit schedule.

[o]Evaluation for SRT may include a cardiopulmonary exercise test (CPET) if CPET is used as standard of care for SRT evaluation by the study site, but it is not required.

TABLE 6.3

Schedule of Assessments Following Septal Reduction Therapy

| Assessments[a] | Weeks After SRT 24 (±7 Days) | 48 (±7 Days) | 72 (±7 Days) | 96 (±7 Days) |
|---|---|---|---|---|
| Postoperative follow-up[b] | X | | | |
| Vital signs[c] | X | X | X | X |
| AEs | X | X | X | X |
| Concomitant medications | X | X | X | X |
| Physical examination[d] | X | X | X | X |
| Resting and Valsalva TTE | X | X | X | X |
| NYHA functional class | X | X | X | X |
| KCCQ-23[e] | X | X | X | X |
| EQ-5D-5L[e] | X | X | X | X |

AE = adverse event;
EQ-5D-5L = EuroQol 5-dimension 5-level questionnaire;
KCCQ-23 = Kansas City Cardiomyopathy Questionnaire (23-item version);
NYHA = New York Heart Association;
SRT = septal reduction therapy;
TTE = transthoracic echocardiogram
[a]Subjects who discontinue study drug to undergo SRT will undergo end-of-treatment assessments within 14 days and will have a telephone follow-up with the study site to assess adverse events 8 weeks after treatment discontinuation (or prior to SRT, whichever is earlier). Subjects will be followed every 24 weeks from the date of SRT to Week 128.
[b]At the first follow-up visit after SRT, the following information should be collected: date of SRT, procedure type (myectomy or alcohol septal ablation), dates of hospitalization, any complications, need for pacemaker, periprocedure adverse events
[c]Blood pressure, heart rate, and respiratory rate will be assessed.
[d]An abbreviated cardiopulmonary physical examination will be conducted.
[e]KCCQ-23 and EQ-5D-5L should be completed prior to any other procedure.

TABLE 6.4

Schedule of Assessments Following Discontinuation of Study Drug

| Assessments[a] | Weeks After Discontinuation of Study Drug 24 (±7 Days) | 48 (±7 Days) | 72 (±7 Days) | 96 (±7 Days) |
|---|---|---|---|---|
| AEs | X | X | X | X |
| Concomitant medications | X | X | X | X |
| Vital signs[b] | X | X | X | X |
| Physical examination[c] | X | X | X | X |
| Single 12-lead ECG | X | X | X | X |
| ICD download | | | | |
| Resting and Valsalva TTE | X | X | X | X |
| NYHA functional class | X | X | X | X |

TABLE 6.4-continued

Schedule of Assessments Following Discontinuation of Study Drug

| Assessments[a] | Weeks After Discontinuation of Study Drug 24 (±7 Days) | 48 (±7 Days) | 72 (±7 Days) | 96 (±7 Days) |
|---|---|---|---|---|
| KCCQ-23[d] | X | X | X | X |
| EQ-5D-5L[d] | X | X | X | X |
| SRT evaluation[e] | X | X | X | X |

AE = adverse event;
ECG = electrocardiogram;
EQ-5D-5L = EuroQol 5-dimension 5-level questionnaire;
ICD = implantable cardioverter-defibrillator;
KCCQ-23 = Kansas City Cardiomyopathy Questionnaire (23-item version);
NYHA = New York Heart Association;
SRT = septal reduction therapy;
TTE = transthoracic echocardiogram
[a]Subjects who permanently discontinue treatment prior to Week 128 will undergo end-of-treatment assessments within 14 days of study drug discontinuation and will be followed every 24 weeks thereafter until Week 128.
[b]Blood pressure, heart rate, and respiratory rate will be assessed.
[c]An abbreviated cardiopulmonary physical examination will be conducted.
[d]KCCQ-23 and EQ-5D-5L should be completed prior to any other procedure.
[e]Evaluation for SRT after discontinuation of study drug should be based on NYHA functional class, maximal medical therapy, and resting and Valsalva TTE. A postexercise TTE is not required.

Example 7. Explorer-HCM Trial: A Phase 3, Double Blind, Randomized, Placebo Controlled, Multicenter, International, Parallel Group Study to Evaluate the Safety, Tolerability, and Efficacy of Mavacamten Compared with Placebo (1:1) in Participants with Symptomatic oHCM A Phase 3, double blind, randomized, placebo controlled, multicenter, international, parallel group study to evaluate the safety, tolerability, and efficacy of mavacamten compared with placebo (1:1) in participants with symptomatic oHCM was conducted. 251 participants were enrolled (123 on mavacamten, 128 on placebo). A subset of participants consented to participate in a CMR substudy at selected sites. Randomization was stratified according to NYHA functional classification (II or III), current treatment with β-blocker (yes or no), planned type of ergometer used during the study (treadmill or exercise bicycle), and consent for the CMR substudy (yes or no).

Study Objective:

The study objectives were as follows

| | |
|---|---|
| Primary Objective | To compare the effect of a 30-week course of mavacamten with placebo on clinical response comprising of exercise capacity and clinical symptoms in participants with symptomatic obstructive hypertrophic cardiomyopathy (oHCM) |
| Secondary Objectives | To compare the effect of a 30-week course of mavacamten with placebo on symptoms and left ventricular outflow tract (LVOT) obstruction as determined by Doppler echocardiography |
| | To compare the effect of a 30-week course of mavacamten with placebo on exercise capacity, clinical symptoms and Patient Reported Outcomes individually |
| | To assess the safety and tolerability of mavacamten |
| | To assess the pharmacokinetic (PK) characteristics of mavacamten |
| Exploratory Objectives | To assess the effect of a 30-week course of mavacamten on LVOT obstruction; disease biomarkers; symptoms, health-related quality of life, and work activity as assessed by patient-reported outcomes (PRO); cardiac rhythm patterns as assessed by continuous cardiac rhythm monitoring; functional capacity as assessed by accelerometer; and risk for sudden cardiac death as assessed by the HCM risk prediction model |

-continued

| | |
|---|---|
| Cardiac Magnetic Resonance Imaging Substudy Objective | To assess the effect of mavacamten on cardiac mass and structure as evaluated by cardiac magnetic resonance imaging (CMR) |

Study Design:

The study included 3 periods carried out according to the following design:

1) Screening period (Day −35 to Day −1): Participants will undergo a variety of general, cardiopulmonary, laboratory, symptom, and PRO assessments over 1 to 2 days in order to assess eligibility. Key Screening tests include electrocardiogram (ECG); transthoracic echocardiography (TTE) conducted at rest, with Valsalva maneuver, and post-exercise; as well as cardiopulmonary exercise testing (CPET). The following screening assessments may be repeated, as long as within the 35-days screening window: blood tests, ECG, and/or TTE. Repeat assessments are allowed if central core labs require a repeat submission due to quality and in order to better assess inclusion/exclusion values. Participants who screen fail may be considered for rescreening based on the investigator's discretion, taking into consideration the reason(s) for screen fail. One attempt at rescreening will be allowed, and all procedures must be repeated.

2) Double-blind treatment period (Day 1 [randomization] to Week 30/end of treatment [EOT]): The double-blind treatment period will include a two-step dose titration scheme designed to achieve safe and effective dosing for each participant based on their own response parameters. Participants who meet all eligibility criteria at Screening will first be randomized via an interactive response system in a 1:1 ratio to receive treatment with mavacamten 5 mg starting dose or matching placebo once daily (QD). Subsequently, assessments including ECG, PK (trough plasma concentrations), and TTE will be performed at each of 7 study visits, beginning at Week 4, and read by core laboratories. At Week 8 and Week 14, the dose may be increased, decreased, or remain unchanged based upon results of Week 6 and Week 12 assessments, respectively, and based primarily on measurements of provoked left ventricular outflow tract (LVOT) gradient and bounded by a target plasma concentration (PK) range and clinical tolerability (LVEF). At Week 8, the dose may be increased to a maximum daily dose of 10 mg (ie, increase from 5 mg QD to 10 mg QD), and at Week 14 to a maximum daily dose of 15 mg (ie, increase from 10 mg QD to 15 mg QD). Dose increases are designed to be step wise and are not allowed to skip doses (eg, from 5 mg to 15 mg).

At Week 30/EOT, participants will complete CPET and post-exercise TTE. For any participants permanently discontinuing treatment prior to Week 30, an early termination (ET) visit should be conducted as soon as possible, including CPET and post-exercise TTE. Participants with ET will also be encouraged to complete all remaining study visits and assessments, including the Week 30 visit.

Figure 16:
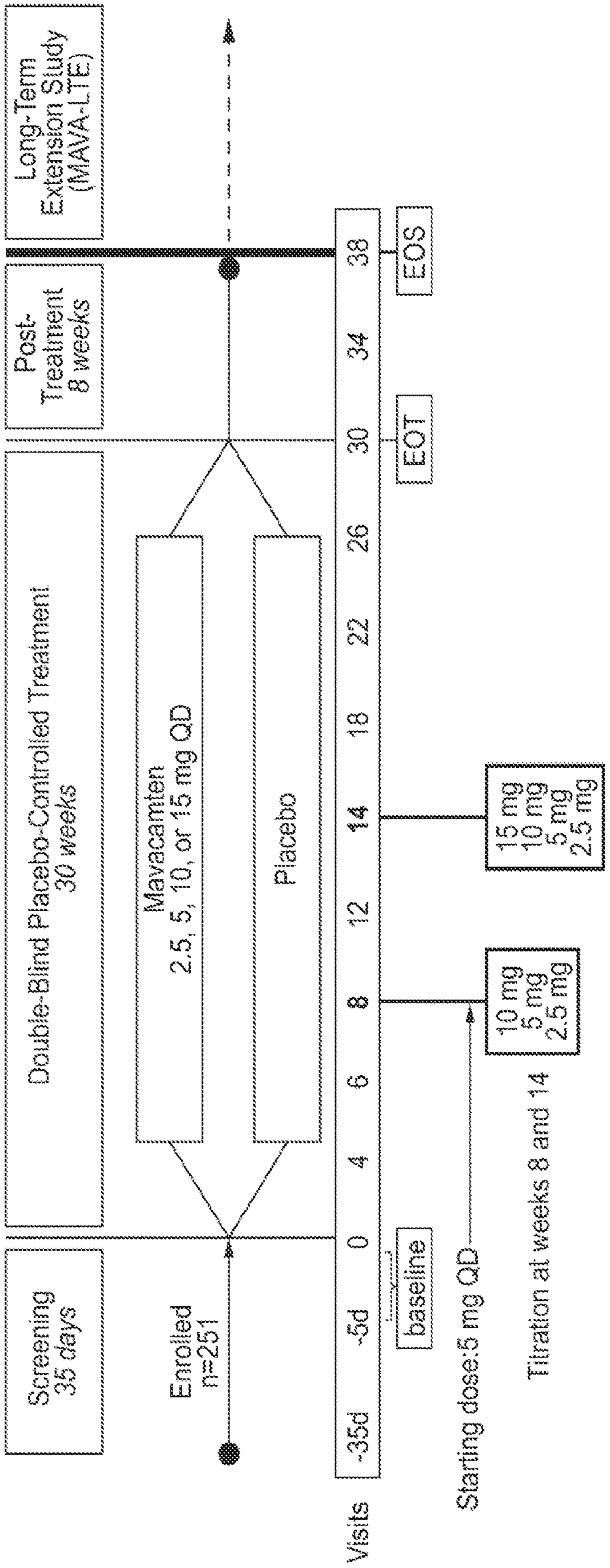
FIG. 16 is a scheme for the study of Example 7.

3) Posttreatment follow-up period (Week 30/EOT to Week 38/end of study [EOS]): When double-blind treatment ends at Week 30, participants will be contacted by phone at Week 34 and return to the site at Week 38 for an EOS visit. At the EOS visit, specified assessments will be repeated. This posttreatment follow-up period applies only to participants who are receiving study drug after Week 22. Study design is shown in FIG. 16.

Safety Monitoring:

Safety monitoring was carried out as follows:

To maintain safety throughout the double-blind treatment period, a clinic visit will occur every 2 to 4 weeks, beginning at Week 4 for an initial evaluation of clinical tolerability and safety. Clinic visits will include but are not limited to clinical evaluation (symptoms, PRO evaluations, adverse event [AE]/serious adverse event [SAE] assessment), ECGs, PK sample, TTEs, and laboratory assessments. Results of TTE performed by study site sonographers at each scheduled visit following randomization should be kept blinded to the investigator and other study site personnel. An exception may occur if left ventricular ejection fraction (LVEF)≤30% is measured at the site, then the investigator will be immediately notified and study drug will be permanently discontinued as described within the protocol.

Assessments at Weeks 4, 6, 8, 12, 18, 22, and 26 will be used to guide dose reduction or temporary discontinuation if indicated, based on predefined criteria detailed within the protocol. If at any time during the double blind treatment period the mavacamten dose is decreased from the previous dose, the participant will continue on the reduced dose to the EOT (Week 30) unless further safety concerns or intolerability arise.

At selected sites, participants will have the option to participate in the CMR substudy. Approximately 80 participants will be enrolled (~40 per treatment group). In addition to the main study schedule of procedures, participants will undergo CMR at Day 1 and Week 30 (or up to 5 days before each visit).

Study Treatment:

Participants received mavacamten immediate release capsules 5 mg or matching placebo QD for the first 8 weeks of the dosing period with trough PK samples drawn at Week 4, Week 6, and Week 8. If at Week 4 the trough PK was between 700 ng/mL and 1000 ng/mL, the dose was decreased to 2.5 mg at Week 6.

Otherwise, the dose was adjusted (increase, decrease, or remain unchanged) at Week 8 based on Week 6 assessments and Week 14 based on Week 12 assessments. The permissible doses after dose adjustment at Week 8 was 2.5 mg, 5 mg, 10 mg, or placebo. The permissible doses after dose adjustment at Week 14 was 2.5 mg, 5 mg, 10 mg, 15 mg, or placebo.

For added safety, if 700 ng/mL<Week 8 PK<1000 ng/mL then an unscheduled visit was arranged 2 weeks later (Week 10) to reduce dose. After Week 14, assessments continued every 4 weeks to Week 30/EOT for safety monitoring.

At any time if PK plasma concentration ≥1000 ng/mL, then study drug was temporarily discontinued.

Each participant was in the study for up to 43 weeks: for Screening, up to 5 weeks; for study conduct, 38 weeks (±7 days).

Inclusion and Exclusion Criteria:

The following inclusion and exclusion criteria were used.

TABLE 7.0

| | |
|---|---|
| Inclusion Criteria | Each participant must meet the following criteria to be included in this study:<br>1. Able to understand and comply with the study procedures, understand the risks involved in the study, and provide written informed consent according to federal, local, and institutional guidelines before the first study-specific procedure<br>2. Is at least 18 years old at Screening<br>3. Body weight is greater than 45 kg at Screening<br>4. Has adequate acoustic windows to enable accurate TTEs (refer to Echocardiography Site Instruction Manual)<br>5. Diagnosed with oHCM consistent with current American College of Cardiology Foundation/American Heart Association and European Society of Cardiology guidelines, ie, satisfy both criteria below (criteria to be documented by the echocardiography core laboratory):<br>A. Has unexplained left ventricular (LV) hypertrophy with nondilated ventricular chambers in the absence of other cardiac (eg, hypertension, aortic stenosis) or systemic disease and with maximal LV wall thickness ≥15 mm (or ≥13 mm with positive family history of hypertrophic cardiomyopathy [HCM]) as determined by core laboratory interpretation, and<br>B. Has LVOT peak gradient ≥50 mmHg during Screening as assessed by echocardiography at rest, after Valsalva maneuver, or post-exercise (confirmed by echocardiography core laboratory interpretation)<br>6. Has documented LVEF ≥55% by echocardiography core laboratory read of Screening TTE at rest<br>7. Has LVOT gradient with Valsalva maneuver at Screening TTE of ≥30 mmHg, determined by echocardiography core laboratory<br>8. Has NYHA Functional Class II or III symptoms at Screening<br>9. Has documented oxygen saturation at rest ≥90% at Screening<br>10. Is able to perform an upright CPET and has a respiratory exchange ratio (RER) ≥1.0 at Screening per central reading; if the RER is between 0.91 and 1.0, the participant may be enrolled only if it is determined by the central CPET laboratory that peak exercise has been achieved in the subject (the only permitted reasons for subpeak performance are [1] a decrease in systolic blood pressure or [2] severe angina as described in the CPET Laboratory Manual)<br>11. Female participants must not be pregnant or lactating and, if sexually active, must use one of the following highly effective birth control methods from the Screening visit through 3 months after the last dose of investigational medicinal product (IMP).<br>combined (estrogen- and progestogen-containing) hormonal contraception associated with inhibition of ovulation or progestogen-only hormonal contraception associated with inhibition of ovulation by oral, implantable, or injectable route of administration<br>intrauterine device (IUD)<br>intrauterine hormone-releasing system (IUS)<br>bilateral tubal occlusion<br>Female is surgically sterile for 6 months or postmenopausal for 1 year. Permanent sterilization includes hysterectomy, bilateral oophorectomy, bilateral salpingectomy, and/or documented bilateral tubal occlusion at least 6 months prior to Screening. Females are considered postmenopausal if they have had amenorrhea for at least 1 year or more following cessation of all exogenous hormonal treatments and follicle stimulating hormone (FSH) levels are in the postmenopausal range.<br>Male partners must also use a contraceptive (eg, barrier, condom or vasectomy) |
| Exclusion Criteria | A participant who meets any of the following exclusion criteria may not participate in this study:<br>1. Previously participated in a clinical study with mavacamten<br>2. Hypersensitivity to any of the components of the mavacamten formulation<br>3. Participated in a clinical trial in which the participant received any investigational drug (or is currently using an investigational device) within 30 days prior to Screening, or at least 5 times the respective elimination half-life (whichever is longer)<br>4. Known infiltrative or storage disorder causing cardiac hypertrophy that mimics oHCM, such as Fabry disease, amyloidosis, or Noonan syndrome with LV hypertrophy<br>5. Has any medical condition that precludes upright exercise stress testing |

TABLE 7.0-continued

| |
|---|
| 6. Has a history of syncope within 6 months prior to screening or history of sustained ventricular tachyarrhythmia with exercise within 6 months prior to Screening |
| 7. Has a history of resuscitated sudden cardiac arrest (at any time) or known history of appropriate implantable cardioverter-defibrillator (ICD) discharge/shock for life-threatening ventricular arrhythmia within 6 months prior to Screening (Note: history of anti-tachycardia pacing (ATP) within 6 months or ever is allowed) |
| 8. Has paroxysmal, intermittent atrial fibrillation with atrial fibrillation present per the investigator's evaluation of the participant's ECG at the time of Screening |
| 9. Has persistent or permanent atrial fibrillation not on anticoagulation for at least 4 weeks prior to Screening and/or not adequately rate-controlled within 6 months prior to Screening (Note - patients with persistent or permanent atrial fibrillation who are anticoagulated and adequately rate-controlled are allowed) |
| 10. Current treatment (within 14 days prior to Screening) or planned treatment during the study with disopyramide or ranolazine |
| 11. Current treatment (within 14 days prior to Screening) or planned treatment during the study with a combination of β-blockers and verapamil or a combination of β-blockers and diltiazem |
| 12. For individuals on β-blockers, verapamil, or diltiazem, any dose adjustment of that medication <14 days prior to Screening or any anticipated change in treatment regimen using these medications during the study |
| 13. Has been successfully treated with invasive septal reduction (surgical myectomy or percutaneous alcohol septal ablation [ASA]) within 6 months prior to Screening or plans to have either of these treatments during the study (note: individuals with myectomy or percutaneous ASA procedure performed >6 months prior to Screening may be enrolled if study eligibility criteria for LVOT gradient criteria are met) |
| 14. ICD placement or pulse generator change within 2 months prior to Screening or planned new ICD placement during the study (pulse generator changes, if needed during the study, are allowed) |
| 15. Has QT interval with Fridericia correction (QTcF) >500 ms at Screening or any other ECG abnormality considered by the investigator to pose a risk to participant safety (eg, second-degree atrioventricular block type II) |
| 16. Has documented obstructive coronary artery disease (>70% stenosis in one or more epicardial coronary arteries) or history of myocardial infarction |
| 17. Has known moderate or severe (as per investigator's judgment) aortic valve stenosis at Screening |
| 18. Has any acute or serious comorbid condition (eg, major infection or hematologic, renal, metabolic, gastrointestinal, or endocrine dysfunction) that, in the judgment of the investigator, could lead to premature termination of study participation or interfere with the measurement or interpretation of the efficacy and safety assessments in the study |
| 19. Has pulmonary disease that limits exercise capacity or systemic arterial oxygen saturation |
| 20. History of malignant disease within 10 years of Screening:<br>Participants who have been successfully treated for nonmetastatic cutaneous squamous cell or basal cell carcinoma or have been adequately treated for cervical carcinoma in situ or breast ductal carcinoma in situ (DCIS) can be included in the study<br>Participants with other malignancies who are cancer-free for more than 10 years before Screening can be included in the study |
| 21. Has safety laboratory parameters (chemistry, hematology, coagulation, and urinalysis) outside normal limits (according to the central laboratory reference range) at Screening as assessed by the central laboratory; however, a participant with safety laboratory parameters outside normal limits may be included if he or she meets all of the following criteria:<br>The safety laboratory parameter outside normal limits is considered by the investigator to be clinically not significant<br>If there is an alanine aminotransferase or aspartate aminotransferase result, the value must be <3 × the upper limit of the laboratory reference range<br>The body size-adjusted estimated glomerular filtration rate is ≥30 mL/min/1.73 $m^2$ |

TABLE 7.0-continued

| | |
|---|---|
| | 22. Has a positive serologic test at Screening for infection with human immunodeficiency virus, hepatitis C virus, or hepatitis B virus<br>23. Has a history or evidence of any other clinically significant disorder, condition, or disease that, in the opinion of the investigator, would pose a risk to participant safety or interfere with the study evaluation, procedures, or completion<br>24. Is currently taking, or has taken within 14 days prior to Screening, a prohibited medication, such as a cytochrome P450 (CYP) 2C19 inhibitor (eg, omeprazole or esomeprazole), a strong CYP 3A4 inhibitor, or St. John's Wort. Alternatives, such as pantoprazole, are allowed and may be discussed with the medical monitor<br>25. Prior treatment with cardiotoxic agents such as doxorubicin or similar<br>26. Unable to comply with the study requirements, including the number of required visits to the clinical site<br>27. Is a first degree relative of personnel directly affiliated with the study at the clinical study site, any study vendor, or the study Sponsor |
| CMR Substudy Inclusion/Exclusion Criteria | Each participant must meet the inclusion/exclusion criteria and be enrolled in the full EXPLORER-HCM clinical trial. In addition, to be included in this substudy, participants must not have:<br>An ICD or pacemaker<br>Atrial fibrillation at the time of Screening (participants who are in atrial fibrillation at the time of imaging will be asked to return at a later time within 1 month, and if the participant is still in atrial fibrillation, the participant will be disqualified from enrolling in the CMR substudy) |

Study Endpoints:

The following endpoints were used for the study:

| | |
|---|---|
| Primary Efficacy Endpoint | Clinical response defined as achieving: 1) An improvement of at least 1.5 mL/kg/min in peak oxygen consumption ($pVO_2$) as determined by CPET and a reduction of one or more class in NYHA Functional Classification or 2) an improvement of 3.0 mL/kg/min or more in $pVO_2$ with no worsening in NYHA Functional Class. |
| Secondary Efficacy Endpoints | Change from baseline to Week 30 in post-exercise LVOT peak gradient<br>Proportion of participants with at least 1 class improvement in NYHA functional class from baseline to Week 30<br>Change from baseline to Week 30 in ($pVO_2$) as determined by CPET<br>Change from baseline to Week 30 in participant-reported health-related quality of life as assessed by the KCCQ score<br>Change from baseline to Week 30 in patient-reported severity of HCM symptoms as assessed by the HCM Symptom Questionnaire score (HCMSQ score) |
| Exploratory Efficacy Endpoints | Proportion of participants achieving a post-exercise LVOT peak gradient <50 mmHg at Week 30<br>Proportion of participants achieving a post-exercise LVOT peak gradient <30 mmHg at Week 30<br>Change from baseline to Week 30 in echocardiographic indices of cardiac structure (LV wall thickness) and function (systolic and diastolic parameters)<br>Change from baseline to Week 30 in N-terminal pro b-type natriuretic peptide (NT-proBNP) concentration over time<br>Change from baseline to Week 30 in the following patient-reported endpoints:<br>Perceived health status/health-related quality of life as assessed by the EuroQol five dimensions 5-level questionnaire scores<br>Work productivity and activity impairment as assessed by the Work Productivity and Activity Impairment questionnaire scores<br>Perceived severity of symptoms assessed by the Patient Global Impression of Change and Patient Global Impression of Severity scores<br>Change from baseline to Week 30 in cardiac rhythm patterns<br>Change from baseline to Week 30 in daily step count and other accelerometer parameters<br>Change from baseline to Week 30 in the HCM risk prediction model<br>Change from baseline to Week 30 in hs-cardiac troponin-I |

-continued

| | |
|---|---|
| Safety Endpoints | Incidence of major adverse cardiac events (death, stroke, acute myocardial infarction)<br>Incidence of hospitalizations (both cardiovascular (CV) and non-CV)<br>Incidence of heart failure (HF) events, (includes HF hospitalizations and urgent emergency room (ER)/outpatient (OP) visits for HF)<br>Incidence of atrial fibrillation/flutter (new from screening)<br>Incidence of ICD therapy and resuscitated cardiac arrest<br>Incidence of Ventricular tachyarrhythmias (includes ventricular tachycardia (VT), ventricular fibrillation (VF), and Torsades de Pointe)<br>Incidence of syncope and seizures<br>Frequency and severity of treatment-emergent adverse events (TEAEs), treatment-emergent SAEs, and laboratory abnormalities (including trends in NT-proBNP) |
| Pharmacokinetic Endpoints | Mavacamten plasma concentration over time<br>PK parameters using a population PK approach |
| CMR Substudy Endpoints | Primary Endpoint<br>Change from baseline to Week 30 in LV mass index<br>Exploratory Endpoints<br>Change from baseline to Week 30 in myocardial fibrosis as measured by late gadolinium enhancement<br>Change from baseline to Week 30 in cellular hypertrophy, left atrial volume and function, and LV function |

Results

Efficacy:

45 of the 123 patients in the intent-to-treat population (36.6%) met the primary efficacy endpoint of a clinical response defined as achieving: 1) An improvement of at least 1.5 mL/kg/min in peak oxygen consumption ($pVO_2$) as determined by CPET and a reduction of one or more class in NYHA Functional Classification or 2) an improvement of 3.0 mL/kg/min or more in $pVO_2$ with no worsening in NYHA Functional Class (referred to as "composite functional response"). Only 22 of 128 patients in the placebo group (17.2%) met the primary efficacy endpoint. Mavacamten provided a statistically significant benefit for the primary efficacy endpoint. The data for the primary efficacy endpoint is shown in Table 7.1

TABLE 7.1

Primary Efficacy Endpoint Results

| Primary Endpoint | Mavacamten (n = 123) | Placebo (n = 128) | Mavacamten vs Placebo |
|---|---|---|---|
| Met Composite Functional Response*, either type, n (%) | 45 (36.6) | 22 (17.2) | 19.4 |
| 95% CI | | | (8.67, 30.13) |
| p-value | | | 0.0005 |
| Response Type 1, n (%) | 41 (33.3) | 18 (14.1) | 19.3 |
| 95% CI | | | (8.99, 29.55) |
| Response Type 2, n (%) | 29 (23.6) | 14 (10.9) | 12.6 |
| 95% CI | | | (3.39, 21.89) |
| pVO2 ≥3.0 and NYHA ≥1 | 25 (20.3) | 10 (7.8) | 12.5 |
| 95% CI | | | (4.02, 21.01) |

*Response Definitions:

Type 1 - pVO2 ≥1.5 ml/kg/min and NYHA improved ≥1

Type 2 - pVO2 ≥3.0 ml/kg/min and no worsening NYHA

Data for the secondary efficacy endpoints are shown in Table 7.2. Mavacamten provided a statistically significant benefit for all secondary efficacy endpoints.

TABLE 7.2

Secondary Efficacy Endpoints Results

| Secondary Endpoint (Change from baseline) | Mavacamten (n = 123) | Placebo (n = 128) | Mavacamten vs Placebo Difference (95% CI) p-value |
|---|---|---|---|
| Post-exercise LVOT peak gradient, mmHg, mean (SD) | −47.2 (40.3) | −10.7 (29.6) | −35.5 (−43.1, −27.9) <0.0001 |
| pVO2, mL/kg/min, mean (SD) | 1.4 (3.1) | −0.05 (3.0) | 1.35 (0.580, 2.116) 0.0006 |
| NYHA improved ≥1 Class, n (%) | 80 (65) | 40 (31.3) | 33.8 (22.1, 45.4) <0.0001 |
| KCCQ-CSS, mean (SD) | 13.6 (14.4) | 4.2 (13.7) | 9.1 (5.46, 12.66) <0.0001 |
| KCCQ-OSS, mean (SD) | 14.87 (15.8) | 5.45 (13.7) | 9.12 (5.46, 12.80) <0.0001 |
| KCCQ-total symptom score, mean (SD) | 12.44 (15.0) | 4.79 (15.9) | 7.60 (3.68, 11.52) 0.0002 |
| HCMSQ-SoB score, mean (SD) | −2.82 (2.7) | −0.85 (2.4) | −1.8 (−2.402, −1.196) <0.0001 |

The Kansas City Cardiomyopathy Questionnaire (23-item version) (KCCQ-23) is a patient reported questionnaire that measures the impact of patients' cardiovascular disease or its treatment on 6 distinct domains using a 2-week recall: symptoms/signs, physical limitations, quality of life, social limitations, self-efficacy, and symptom stability (Green et al, 2000). In addition to the individual domains, 2 summary scores can be calculated from the KCCQ-23: the overall summary score (OSS) (includes the total symptom, physical limitation, social limitations and quality of life scores) and the clinical summary score (CSS) (combines the total symptom and physical limitation scales). Scores range from 0 to 100, with higher scores reflecting better health status.

HCMSQ score is a patient-reported outcome instrument (questionnaire) applied to evaluate HCM symptoms in clinical practice to inform diagnosis to specifically capture symptoms of HCM and to assess therapeutic response longitudinally. HCMSQ-SoB score is a sub-score for questions 1-6 of the HCMSQ. Study participants received a handheld electronic device and training at Screening. During Screening they completed the HCMSQ daily for a minimum of 7 days and every day for the first 6 weeks after treatment initiation. Participants completed the HCMSQ on the handheld electronic device daily for a consecutive 7-day (1-week) period prior to the Week 10, 14, 18, 22, 26, 30 (EOT), and 38 (EOS) time points.

The HCMSQ Questionnaire:

| Core Symptom | Item | Question | Response Options |
|---|---|---|---|
| Shortness of breath | 1 | Were you short of breath during the past 24 hours? | 0 = Not at all<br>1 = Mildly<br>2 = Moderately<br>3 = Severely<br>4 = Very Severely |
| | 2 | Were you short of breath during light physical activity such as walking slowly or cooking during the past 24 hours? | . = I did not attempt to do the activity<br>0 = Not at all<br>1 = Mildly<br>2 = Moderately<br>3 = Severely<br>4 = Very Severely<br>5 = Too short of breath to do the activity |
| | 3 | Were you short of breath during moderate physical activity such as cleaning house or lifting heavy objects? | . = I did not attempt to do the activity<br>0 = Not at all<br>1 = Mildly<br>2 = Moderately<br>3 = Severely<br>4 = Very Severely<br>5 = Too short of breath to do the activity |
| | 4 (removed) | Were you short of breath during heavy physical activity such as jogging or playing sports during the past 24 hours? | . = I did not attempt to do the activity<br>0 = Not at all<br>1 = Mildly<br>2 = Moderately<br>3 = Severely<br>4 = Very Severely<br>5 = Too short of breath to do the activity |
| | 5 (removed) | Describe your shortness of breath at its worst during the past 24 hours. | 0 = No shortness of breath<br>1 = Short of breath during heavy physical activity<br>2 = Short of breath during moderate physical activity<br>3 = Short of breath during light physical activity<br>4 = Short of breath when resting |
| | 6 | How often did you have shortness of breath during past 24 hours? | 0 = Never<br>1 = Seldom<br>2 = Sometimes<br>3 = Often<br>4 = Almost Always |
| Tiredness/ fatigue | 7 | Were you tired during past 24 hours? | 0 = Not at all<br>1 = Mildly<br>2 = Moderately<br>3 = Severely<br>4 = Very Severely |
| Heart palpitations | 8 | Did your heart beat rapidly or flutter (palpitations) during past 24 hours? | 0 = Not at all<br>1 = Mildly<br>2 = Moderately<br>3 = Severely<br>4 = Very Severely |
| Chest pain | 9 | Did you have chest pain during the past 24 hours? | 0 = Not at all<br>1 = Mildly<br>2 = Moderately<br>3 = Severely<br>4 = Very Severely |
| Dizziness | 10 | Were you dizzy or light-headed during the past 24 hours? | 0 = Not at all<br>1 = Mildly<br>2 = Moderately<br>3 = Severely<br>4 = Very Severely |
| Syncope | 11 | Did you faint or lose consciousness during the past 24 hours? | 1 = Yes<br>0 = No |

65% of patients on mavacamten achieved NYHA class I status compared to 21% on placebo. 57% of patients on mavacamten achieved a post-exercise LVOT peak gradient below 30 mmHg compared to 700 on placebo. 27% of patients on mavacamten achieved a complete response (NYHA 1 and all LVOT gradients below 30 mmHg) compared to 100 on placebo.

Data for key exploratory efficacy endpoints are shown in Table 7.3. Mavacamten showed a statistically significant improvement over placebo for each key exploratory efficacy endpoint.

TABLE 7.3

Key Exploratory Efficacy Endpoints Results

| Exploratory Endpoints | Mavacamten n/assessible (%) | Placebo n/assessible (%) | Mava vs Placebo Difference (95% CI) p-value |
|---|---|---|---|
| Post-exercise LVOT peak gradient < 50 mmHg | 75/101 (74.3) | 22/106 (20.8) | 53.5 (42.0. 65.0) <0.0001 |
| Post-exercise LVOT peak gradient < 30 mmHg | 64/113 (56.6) | 8/113 (7.1) | 49.6 (39.3, 59.8) <0.0001 |
| Complete Response* | 32/117 (27.4) | 1/126 (0.8) | 26.6 (18.3, 34.8) <0.0001 |
| Absence of SAM (systolic anterior motion of mitral valve) | 76/94 (80.9) | 33/97 (34.0) | 46.9 (34.5, 59.2) <0.0001 |
| Absence of MR (mitral regurgitation) | 10/111 (9.0) | 0/120 (0.0) | 9.0 (3.7, 14.3) 0.0006 |

*Complete Response defined as NYHA Class I and all LVOT gradients < 30 mmHg

Data for key biomarker results are shown in Table 7.4. Mavacamten showed a statistically significant decrease in NT-proBNP levels and in hs-cTnI levels compared to placebo.

TABLE 7.4

| Biomarker | Mavacamten Geometric mean (CV %) Baseline | Placebo Geometric mean (CV %) Baseline | Mavacamten Week 30 ratio to BL (CV %) | Placebo Week 30 ratio to BL (CV %) | Mava vs Placebo Model Est RR (95% CI) p-value |
|---|---|---|---|---|---|
| NT-proBNP (ng/L) | 777.4 (136) | 615.7 (108) | N = 116 0.204 (266.9) | N = 121 1.024 (55.8) | 0.202 (0.169, 0.241) <0.0001 |
| hs-cTnI (ng/L) | 12.51 (208) | 12.45 (373) | N = 114 0.584 (49.2) | N = 111 0.993 (143.3) | 0.589 (0.500, 0.693) <0.0001 |

Baseline characteristics for the study population are shown in Table 7.5. Baseline characteristics are measured prior to treatment. Improvements are defined relative to baseline.

TABLE 7.5

Baseline Characteristics

| | Mavacamten (n = 123) | Placebo (n = 128) |
|---|---|---|
| Age, mean, years (SD) | 58.5 (12.2) | 58.5 (11.8) |
| Female sex, n (%) | 57 (46.3) | 45 (35.2) |
| White race, n (%) | 115 (93.5) | 114 (89.1) |
| US | 53 (43.1) | 55 (43.0) |
| ex-US | 70 (56.9) | 73 (57.0) |
| NYHA class, n (%) | | |
| Class II | 88 (71.5) | 95 (74.2) |
| Class III | 35 (28.5) | 33 (25.8) |

TABLE 7.5-continued

Baseline Characteristics

| | Mavacamten (n = 123) | Placebo (n = 128) |
|---|---|---|
| Peak $VO_2$, mL/kg/min, mean (SD) | 18.93 (4.86) | 19.90 (4.91) |
| NT-proBNP, pg/mL, median, (Q1, Q3) | 783.5 (373, 1759) | 648 (354, 1360) |
| Background therapy, n (%) | | |
| Beta blocker | 94 (76) | 95 (74) |
| Calcium channel blocker | 25 (20) | 17 (13) |
| LVEF, % (SD) | 74.1 (5.8) | 74.2 (5.9) |
| Resting LVOT gradient, mmHg, mean (SD) | 51.7 (29.4) | 51.1 (31.9) |
| Valsalva LVOT gradient, mmHg, mean (SD) | 72.3 (31.7) | 73.9 (32.0) |
| Post-exercise LVOT gradient, mmHg, mean (SD) | 85.7 (34.3) | 84.7 (35.6) |

TABLE 7.5-continued

| Baseline Characteristics | | |
|---|---|---|
| | Mavacamten (n = 123) | Placebo (n = 128) |
| Interventricular septum thickness, mm, mean (SD) | 16.8 (2.5) | 16.7 (2.8) |
| Posterior wall thickness, mm, mean (SD) | 11.7 (2.4) | 11.4 (2.4) |
| Lateral e', cm/s, mean (SD) | 6.3 (2.0) | 6.6 (2.4) |
| Septal e', cm/s, mean (SD) | 4.6 (1.2) | 4.8 (1.5) |
| E/e' average, mean (SD) | 19.1 (6.5) | 19.3 (8.3) |
| LA volume index, mL/$m^2$, mean (SD) | 40.3 (12.1) | 40.6 (13.8) |

The data was also examined for subgroups of patients receiving versus not receiving background β blocker(s). Most patients who were not receiving β blocker(s) were receiving calcium channel blocker(s) and a few patients received neither β blocker(s) nor calcium channel blocker(s). In patients without concomitant R blockade, the effect of mavacamten treatment on the primary endpoint was greater, as compared to patients on β blocker(s).

For patients not receiving β blocker(s), the percent of patients on mavacamten (n=29) that met the primary endpoint was greater by a 52.6% difference compared to corresponding patients on placebo (n=33). For patients receiving β blocker(s), the percent of patients on mavacamten (n=94) that met the primary endpoint was greater by a 8.7% difference compared to corresponding patients on placebo (n=95). The mean peak heart rate with exercise tended to be lower for the subgroup of patients using β blocker(s) (119 beats per min at baseline) compared to those not using β blocker(s) (138 beats per min at baseline). Also, mean $pVO_2$, a component of the primary endpoint, was lower for the β blocker subgroup at baseline, and the mean change at week 30 in $pVO_2$ was also lower for the β blocker subgroup (1.1 mL/kg/min) compared to those not using β blocker(s) (2.2 mL/kg/min).

Heart rate independent parameters of CPET, including $VE/VCO_2$ slope, showed improvement for mavacamten compared to placebo irrespective of β blocker use. The $VE/CO_2$ slope change from baseline at week 30 was −2.5 in the β blocker subgroup and −2.5 in the non-β blocker subgroup. Rates of improvement by at least one NYHA class with mavacamten treatment were also similar among patients receiving β blocker(s) and those who were not (both 65%). All secondary endpoints, including change in LVOT gradient showed consistent benefit for mavacamten across all subgroups, irrespective of β blocker use.

Figure 17:
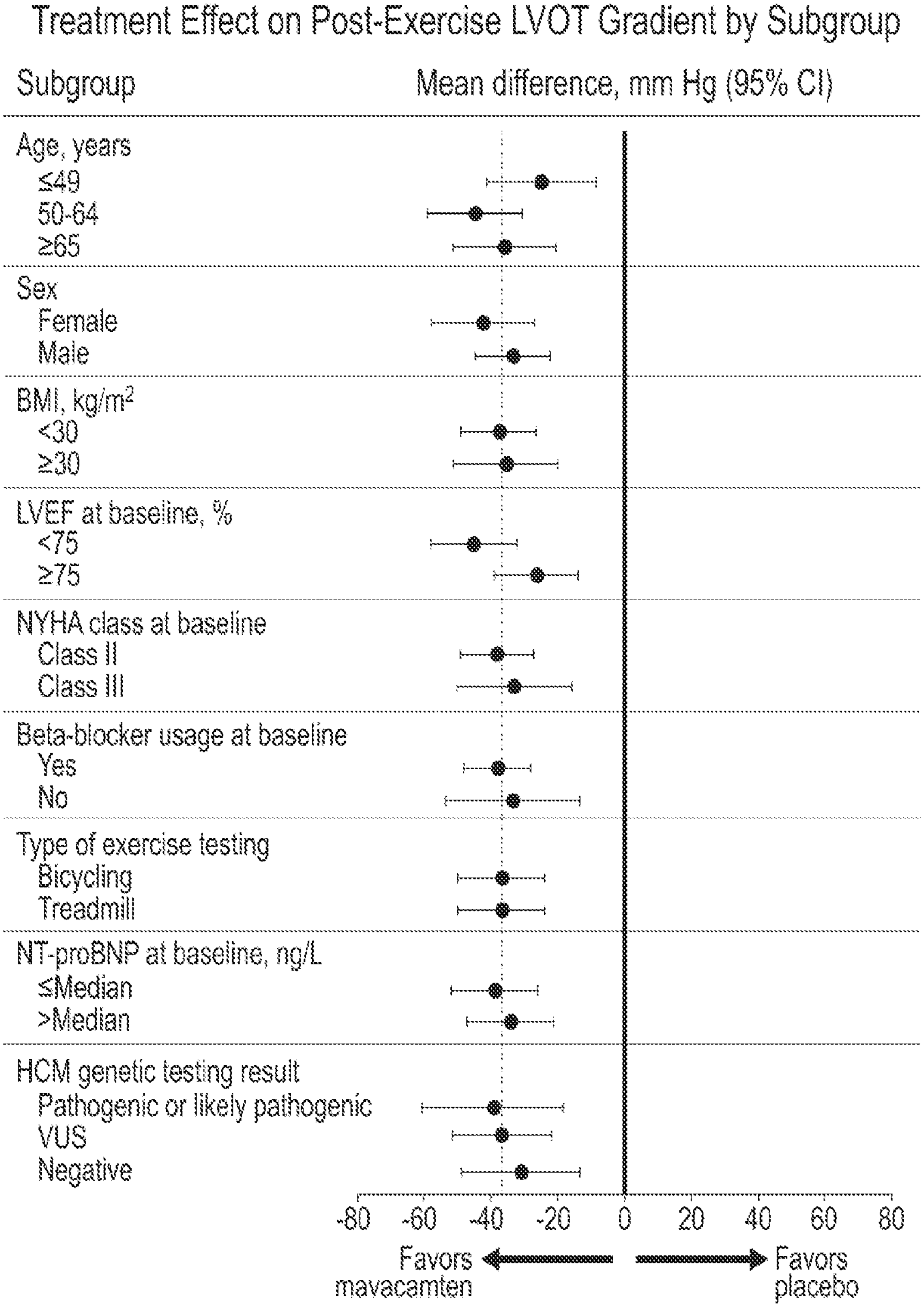
FIG. 17 is a Forest Plot of treatment effect on post-exercise LVOT gradient by subgroup from the study of Example 7.
Figure 18:
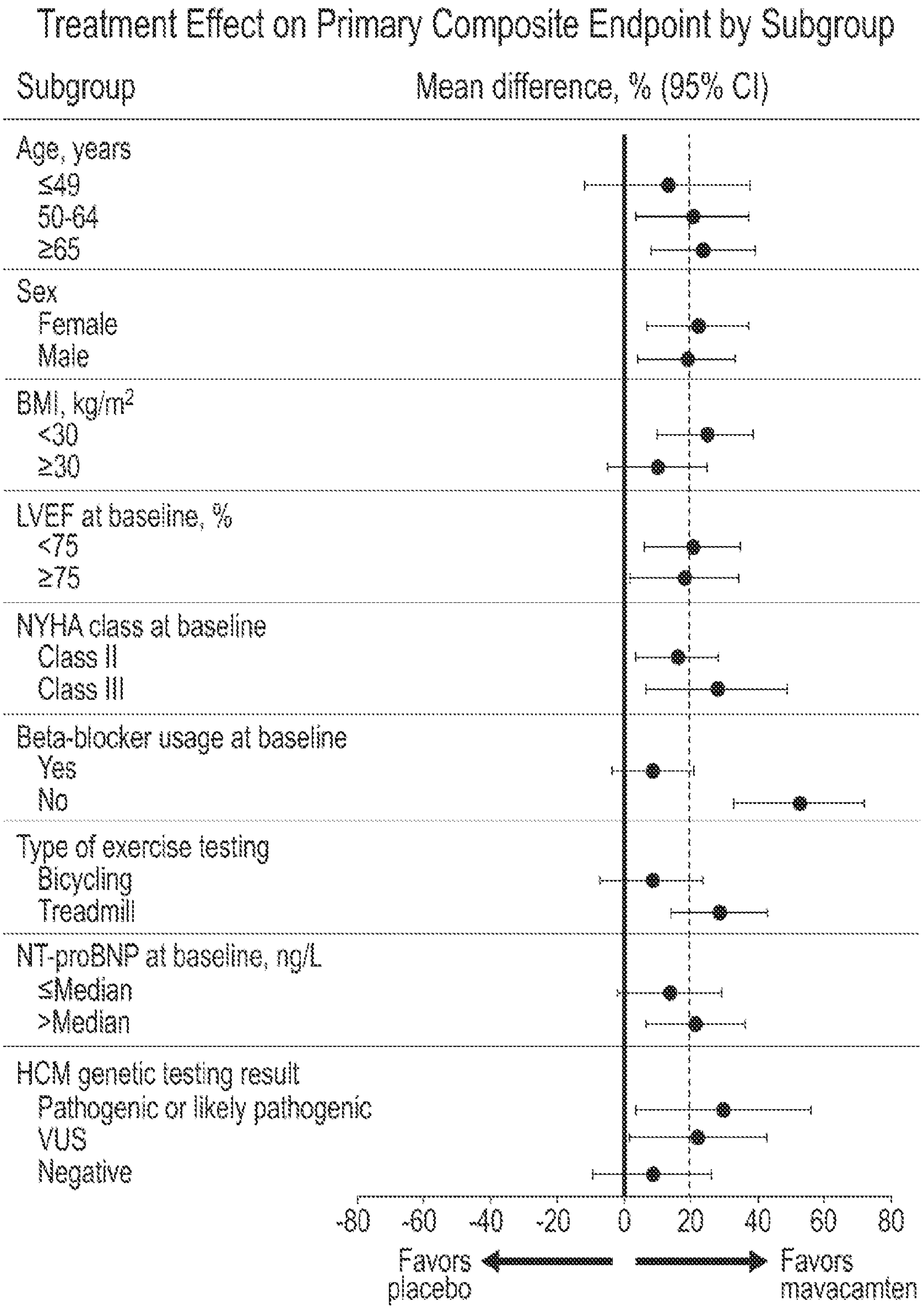
FIG. 18 is a Forest Plot of treatment effect on Primary Composite Endpoint by subgroup from the study of Example 7.

Consistent benefit of mavacamten therapy was observed across all patient subgroups. FIGS. 17 and 18 show Forest Plots of treatment effect on post-exercise LVOT gradient and Primary Composite Endpoint by subgroup.

Safety:

Few discontinuations were reported. 8 temporary discontinuations were reported in patients on mavacamten (all patients were at a 5 mg dose) and 7 temporary discontinuations were reported in patients on placebo. One disease related sudden death occurred on placebo. No other disease-related SAEs were reported. Five permanent treatment discontinuations were reported: 3 were due to adverse events of which 2 were on mavacamten (atrial fibrillation, syncope) and 1 on placebo (sudden death); and 2 were due to subject self-withdrawal (1 mavacamten, 1 placebo) of which one was due to the patient moving away from site, and the other was due to the patient deciding to stop study drug.

Mavacamten was well tolerated and demonstrated a safety profile in line with placebo at doses ranging from 2.5 to 15 mg. 10 (8.1%) subjects experienced SAEs on mavacamten through week 30. 11 (8.6%) subjects on placebo experienced AEs. The number of SAEs was 12 on mavacamten vs. 20 on placebo. Severe TEAEs occurred in 7 (5.7%) of subjects on mavacamten, vs. 13 (10.2%) on placebo. Cardiac SAEs occurred in 4 patients on mavacamten and 4 patients on placebo.

The dosing approach based on standard echocardiographic measures worked well and consistently. 5 of 251 participants experienced a temporary discontinuation associated with reduced ejection fraction (3 mavacamten, 2 placebo). Following a dose modification, all of the mavacamten patients returned to and completed the study.

CONCLUSION

Mavacamten demonstrated a robust treatment effect on the primary and all secondary endpoints of the Phase 3 EXPLORER pivotal study with statistical significance ($p<0.0006$ for all endpoints). For the vast majority of patients on mavacamten treatment, symptoms were diminished, exercise capacity increased and obstruction of the left ventricle—a defining characteristic of their condition—was reduced or eliminated.

The data from the EXPLORER pivotal trial confirm mavacamten's ability to be dosed safely to achieve statistically significant, clinically meaningful results. Treatment with mavacamten resulted in a statistically significant benefit relative to placebo ($p=0.0005$) for the primary endpoint for EXPLORER-HCM, a composite functional analysis designed to capture mavacamten's effect on both symptoms and cardiac function. Secondary endpoints also demonstrated statistically significant improvements as compared to placebo.

Mavacamten was well tolerated and demonstrated a safety profile consistent with prior mavacamten clinical studies and comparable with placebo. A greater number of serious adverse events (SAEs) occurred among patients in the placebo arm vs. the treatment arm (20 vs. 12). Overall rates of cardiac AEs were similar in the active and placebo cohorts, and not directly attributable to use of mavacamten.

Long-Term Extension:

Participants may receive mavacamten as part of a long-term extension study following completion of the Explorer study. Background cardiomyopathy therapy (e.g., beta blocker, verapamil, or diltiazem) is allowed during the extension study, provided a participant has been on a stable dose for at least 14 days prior to screening. Background therapy, including beta blocker, may be adjusted or stopped after a participant has received 24 weeks of mavacamten treatment in the extension study.

We claim:

1. A method of treating a patient having cardiac hypercontractility, impaired cardiac relaxation and/or left ventricular hypertrophy, wherein the patient is undergoing β blocker therapy, the method comprising:

discontinuing the β blocker therapy or reducing the amount of β blocker therapy; and administering to the patient a therapeutically effective amount of a myosin inhibitor;

wherein the patient achieves an improvement in $pVO_2$ of at least about 2.2 mL/kg/min.

2. A method of treating a patient having cardiac hypercontractility, impaired cardiac relaxation and/or left ventricular hypertrophy, wherein the patient is undergoing β blocker therapy, the method comprising:

discontinuing the β blocker therapy or reducing the amount of β blocker therapy; and administering to the patient a therapeutically effective amount of a myosin inhibitor;

wherein the patient achieves (i) an improvement of at least 1.5 mL/kg/min in $pVO_2$ and a reduction of 1 or more NYHA Class, or (ii) an improvement of at least 3.0 mL/kg/min in $pVO_2$ with no worsening in NYHA Class.

3. A method of treating a patient having cardiac hypercontractility, impaired cardiac relaxation and/or left ventricular hypertrophy, wherein the patient is undergoing β blocker therapy, the method comprising:

discontinuing the β blocker therapy or reducing the amount of β blocker therapy; and administering to the patient a therapeutically effective amount of a myosin inhibitor;

wherein the patient has one or more of:

an ejection fraction >55% prior to administration of the myosin inhibitor;

an E/e'>14 prior to administration of the myosin inhibitor; and a left ventricular wall thickness ≥15 mm or ≥13 mm with family history of HCM prior to administration of the myosin inhibitor.

4. A method of treating a patient having cardiac hypercontractility, impaired cardiac relaxation and/or left ventricular hypertrophy, wherein the patient is undergoing β blocker therapy, the method comprising:

discontinuing the β blocker therapy or reducing the amount of β blocker therapy; and administering to the patient a therapeutically effective amount of a myosin inhibitor;

wherein the patient with cardiac hypercontractility has ejection fraction of >55% and evidence of oHCM, HCM and/or heart failure symptoms prior to beginning the first treatment phase.

5. The method of claim 1, wherein the patient is suffering from oHCM, and wherein the method comprises discontinuing the β blocker therapy.

6. The method of claim 5, wherein the myosin inhibitor is mavacamten or a pharmaceutically acceptable salt thereof.

7. The method of claim 5, wherein the myosin inhibitor is mavacamten.

8. The method of claim 5, wherein the myosin inhibitor is:

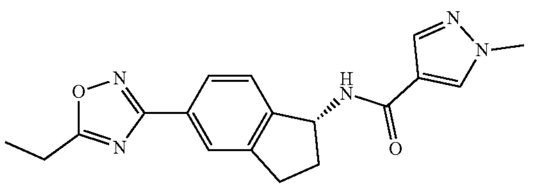 [SMILES: CCc1nc(-c2ccc3c(c2)CC[C@H]3NC(=O)c2cnn(C)c2)no1]

or a pharmaceutically acceptable salt thereof.

9. The method of claim 5, wherein the myosin inhibitor is:

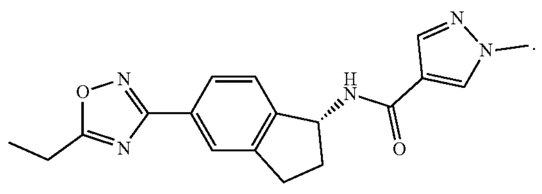 [SMILES: CCc1nc(-c2ccc3c(c2)CC[C@H]3NC(=O)c2cnn(C)c2)no1]

10. The method of claim 2, wherein the patient is suffering from oHCM, and wherein the method comprises discontinuing the β blocker therapy.

11. The method of claim 10, wherein the myosin inhibitor is mavacamten or a pharmaceutically acceptable salt thereof.

12. The method of claim 10, wherein the myosin inhibitor is mavacamten.

13. The method of claim 10, wherein the myosin inhibitor is:

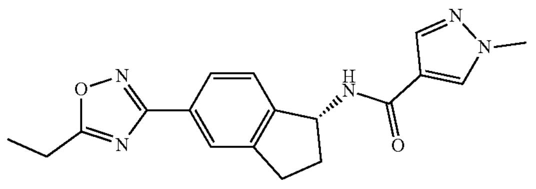 [SMILES: CCc1nc(-c2ccc3c(c2)CC[C@H]3NC(=O)c2cnn(C)c2)no1]

or a pharmaceutically acceptable salt thereof.

14. The method of claim 10, wherein the myosin inhibitor is:

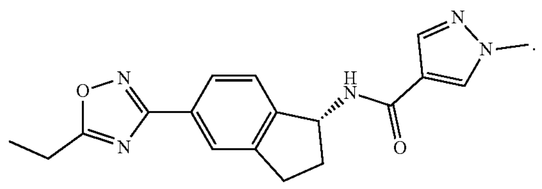 [SMILES: CCc1nc(-c2ccc3c(c2)CC[C@H]3NC(=O)c2cnn(C)c2)no1]

15. The method of claim 3, wherein the patient is suffering from oHCM, and wherein the method comprises discontinuing the β blocker therapy.

16. The method of claim 15, wherein the myosin inhibitor is mavacamten or a pharmaceutically acceptable salt thereof.

17. The method of claim 15, wherein the myosin inhibitor is mavacamten.

18. The method of claim 15, wherein the myosin inhibitor is:

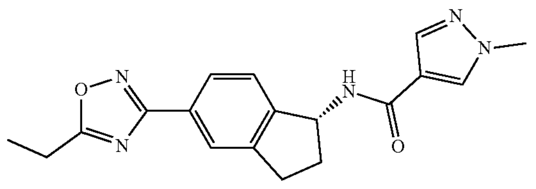

or a pharmaceutically acceptable salt thereof.

19. The method of claim 15, wherein the myosin inhibitor is:

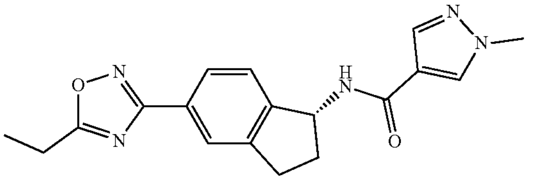

.

20. The method of claim 4, wherein the patient is suffering from oHCM, and wherein the method comprises discontinuing the β blocker therapy.

21. The method of claim 20, wherein the myosin inhibitor is mavacamten or a pharmaceutically acceptable salt thereof.

22. The method of claim 20, wherein the myosin inhibitor is mavacamten.

23. The method of claim 20, wherein the myosin inhibitor is:

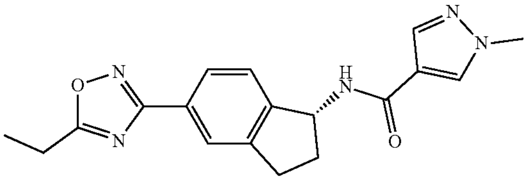

or a pharmaceutically acceptable salt thereof.

24. The method of claim 20, wherein the myosin inhibitor is:

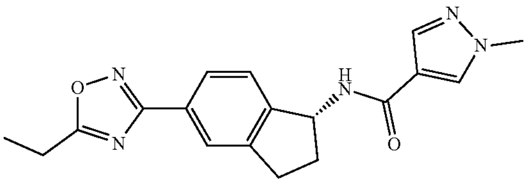 [SMILES: CCc1nc(-c2ccc3c(c2)CC[C@H]3NC(=O)c2cnn(C)c2)no1]

.

25. The method of claim 1, comprising discontinuing the β blocker therapy.

26. The method of claim 1, comprising reducing the amount of β blocker therapy.

27. The method of claim 25, wherein the myosin inhibitor is mavacamten or a pharmaceutically acceptable salt thereof.

28. The method of claim 25, wherein the myosin inhibitor is a compound selected from the group consisting of:

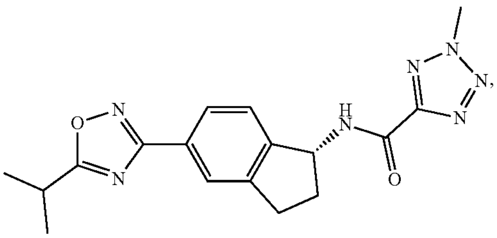

,

-continued

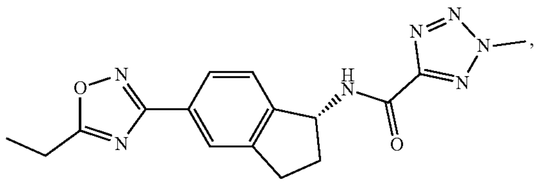

,

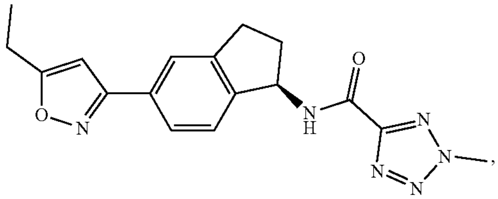

,

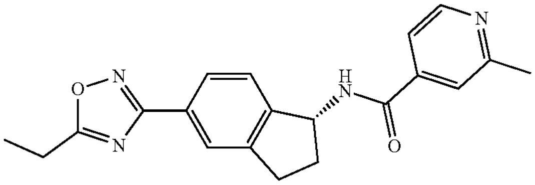

,

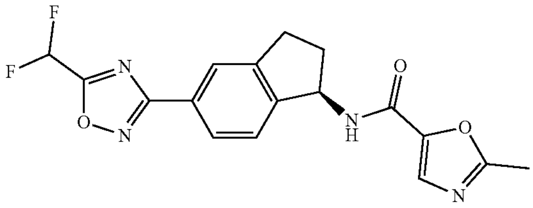

,

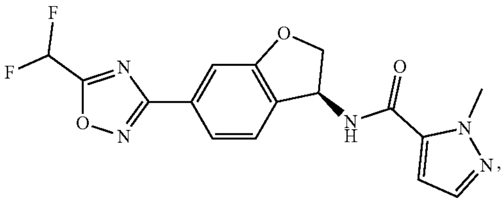

,

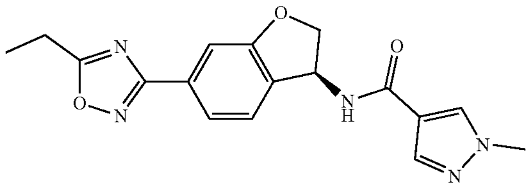

,

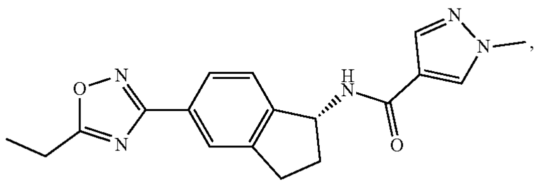 [SMILES: CCc1nc(-c2ccc3c(c2)CC[C@H]3NC(=O)c2cnn(C)c2)no1]

,

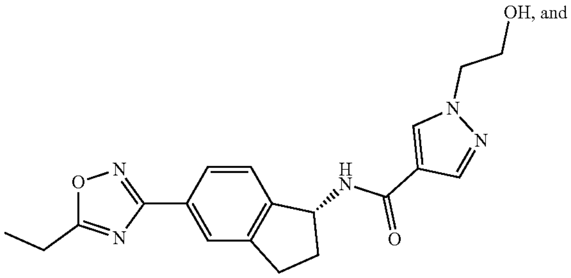

and

-continued

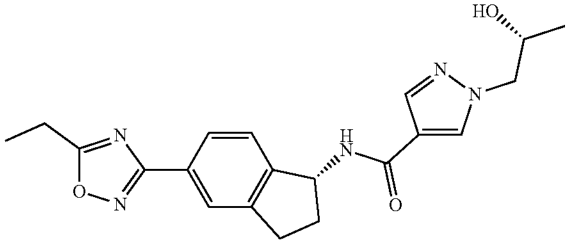

or a pharmaceutically acceptable salt thereof.

29. The method of claim 28, wherein the myosin inhibitor is:

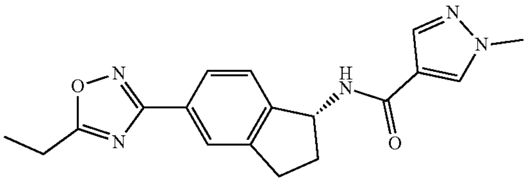 [SMILES: CCc1nc(-c2ccc3c(c2)CC[C@H]3NC(=O)c2cnn(C)c2)no1]

or a pharmaceutically acceptable salt thereof.

30. The method of claim 1, wherein the patient has obstructive hypertrophic cardiomyopathy (oHCM), non-obstructive hypertrophic cardiomyopathy (nHCM), or heart failure with preserved ejection fraction (HFpEF).

31. The method of claim 30, wherein the patient has obstructive hypertrophic cardiomyopathy (oHCM).

32. The method of claim 2, comprising discontinuing the β blocker therapy.

33. The method of claim 2, comprising reducing the amount of β blocker therapy.

34. The method of claim 32, wherein the myosin inhibitor is mavacamten or a pharmaceutically acceptable salt thereof.

35. The method of claim 32, wherein the myosin inhibitor is a compound selected from the group consisting of:

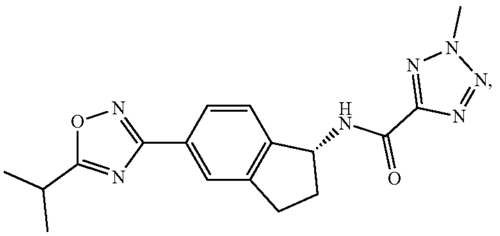

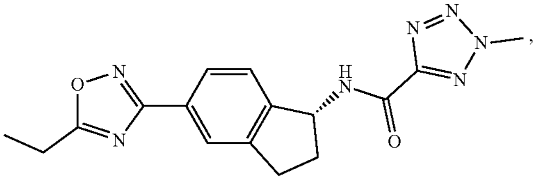 [SMILES: CCc1nc(-c2ccc3c(c2)CC[C@H]3NC(=O)c2cnn(C)c2)no1]

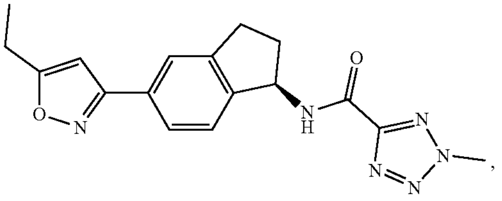

-continued

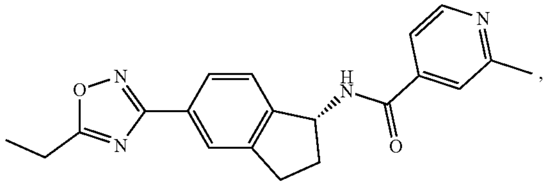

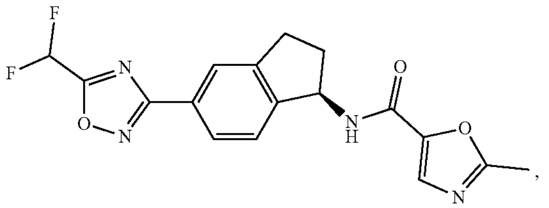

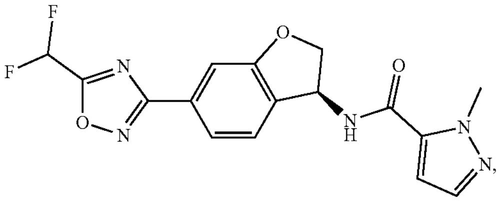

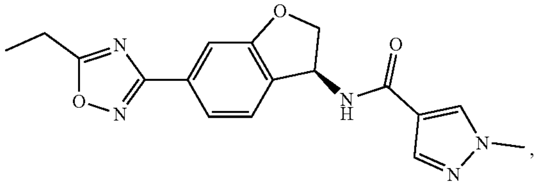

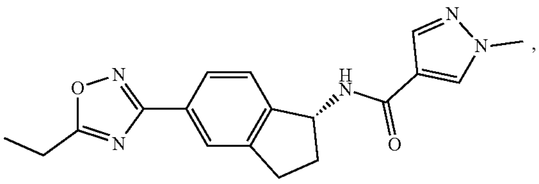

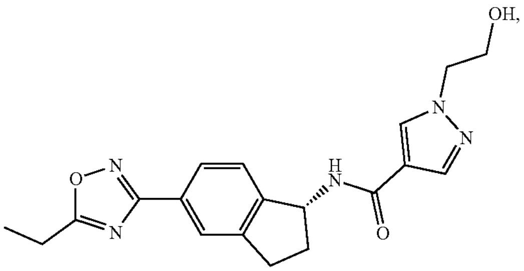

and

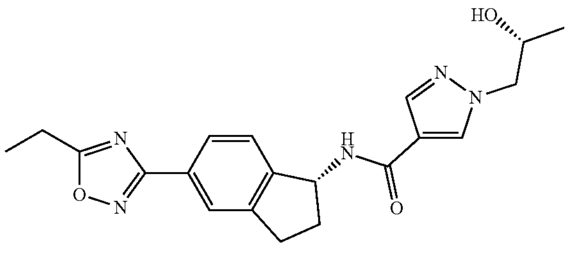

or a pharmaceutically acceptable salt thereof.

36. The method of claim 35, wherein the myosin inhibitor is the following compound:

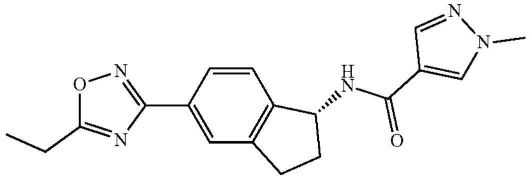 [SMILES: CCc1nc(-c2ccc3c(c2)CC[C@H]3NC(=O)c2cnn(C)c2)no1]

or a pharmaceutically acceptable salt thereof.

37. The method of claim 2, wherein the patient has obstructive hypertrophic cardiomyopathy (oHCM), non-obstructive hypertrophic cardiomyopathy (nHCM), or heart failure with preserved ejection fraction (HFpEF).

38. The method of claim 37, wherein the patient has obstructive hypertrophic cardiomyopathy (oHCM).

39. The method of claim 3, comprising discontinuing the β blocker therapy.

40. The method of claim 3, comprising reducing the amount of β blocker therapy.

41. The method of claim 39, wherein the myosin inhibitor is mavacamten or a pharmaceutically acceptable salt thereof.

42. The method of claim 39, wherein the myosin inhibitor is a compound selected from the group consisting of:

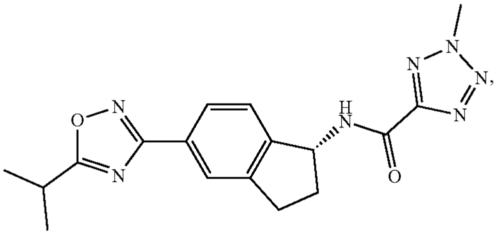

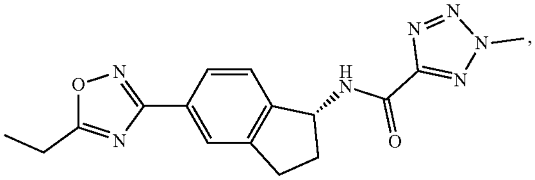

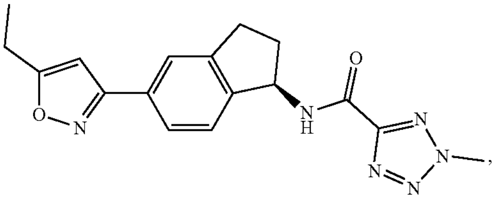

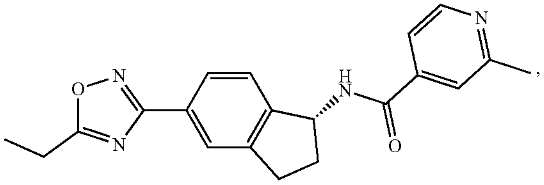

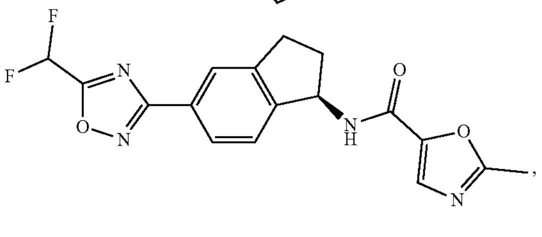

-continued

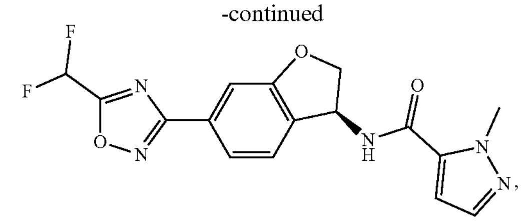

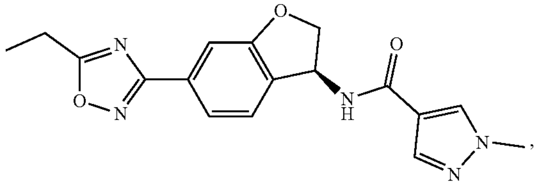

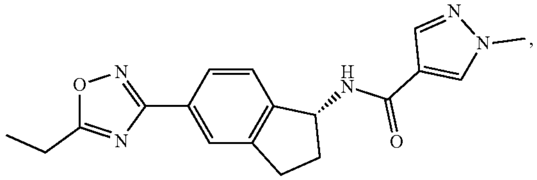

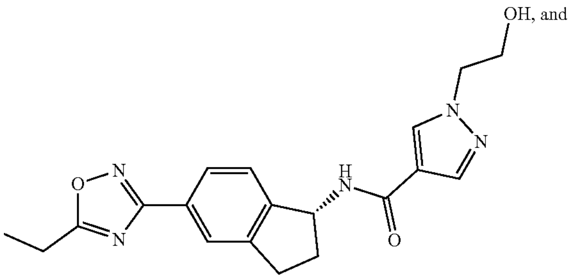

and

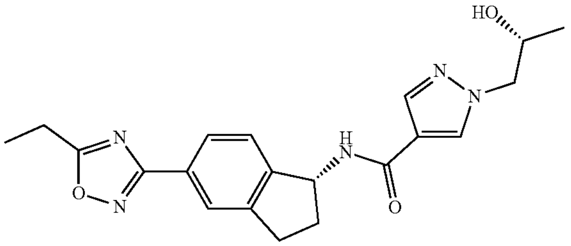

or a pharmaceutically acceptable salt thereof.

43. The method of claim 42, wherein the myosin inhibitor is:

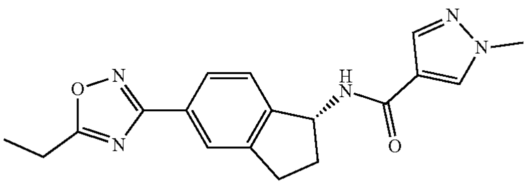 [SMILES: CCc1nc(-c2ccc3c(c2)CC[C@H]3NC(=O)c2cnn(C)c2)no1]

or a pharmaceutically acceptable salt thereof.

44. The method of claim 3, wherein the patient has obstructive hypertrophic cardiomyopathy (oHCM), non-obstructive hypertrophic cardiomyopathy (nHCM), or heart failure with preserved ejection fraction (HFpEF).

45. The method of claim 44, wherein the patient has obstructive hypertrophic cardiomyopathy (oHCM).

46. The method of claim 4, comprising discontinuing the β blocker therapy.

47. The method of claim 4, comprising reducing the amount of β blocker therapy.

48. The method of claim 46, wherein the myosin inhibitor is mavacamten or a pharmaceutically acceptable salt thereof.

49. The method of claim 46, wherein the myosin inhibitor is a compound selected from the group consisting of:

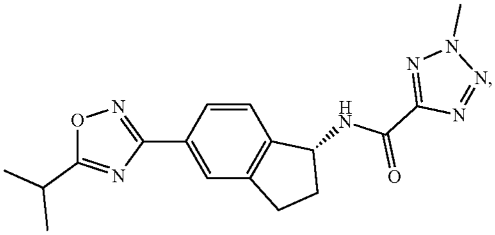

,

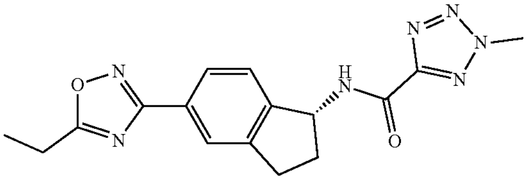

,

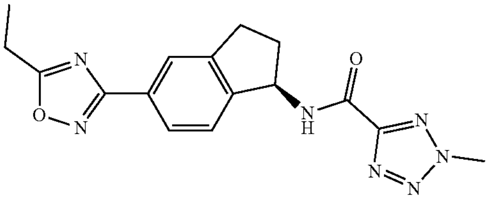

,

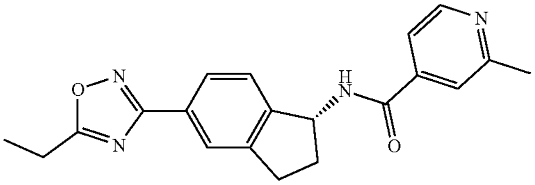

,

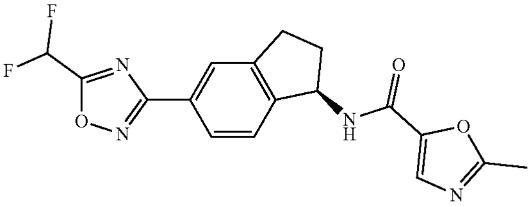

,

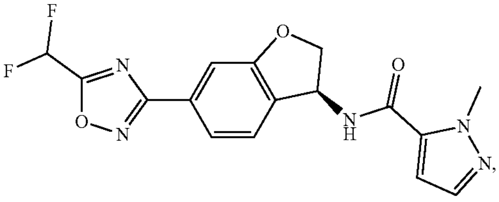

,

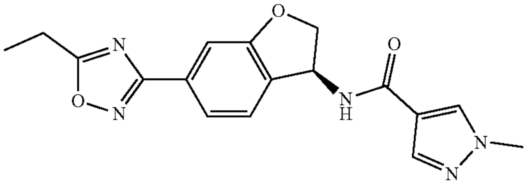

,

-continued

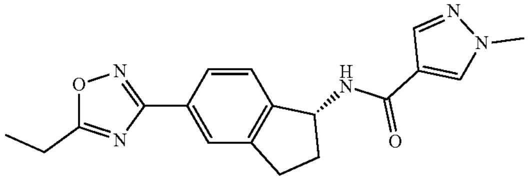 [SMILES: CCc1nc(-c2ccc3c(c2)CC[C@H]3NC(=O)c2cnn(C)c2)no1]

,

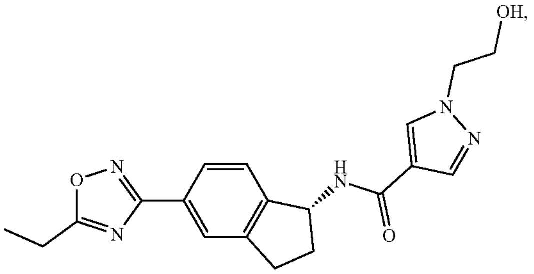

, and

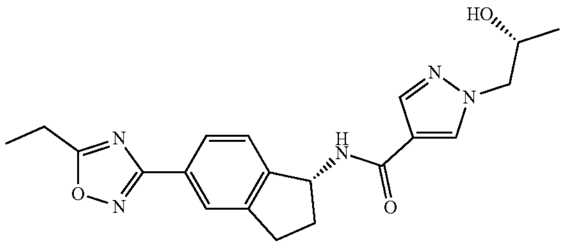

or a pharmaceutically acceptable salt thereof.

50. The method of claim 49, wherein the myosin inhibitor is the following compound:

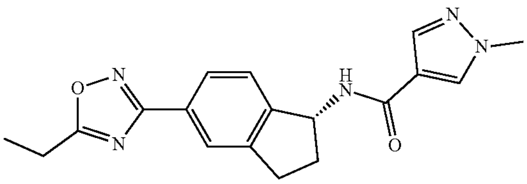 [SMILES: CCc1nc(-c2ccc3c(c2)CC[C@H]3NC(=O)c2cnn(C)c2)no1]

or a pharmaceutically acceptable salt thereof.

51. The method of claim 4, wherein the patient has obstructive hypertrophic cardiomyopathy (oHCM), non-obstructive hypertrophic cardiomyopathy (nHCM), or heart failure with preserved ejection fraction (HFpEF).

52. The method of claim 51, wherein the patient has obstructive hypertrophic cardiomyopathy (oHCM).

* * * * *